Figure 1:
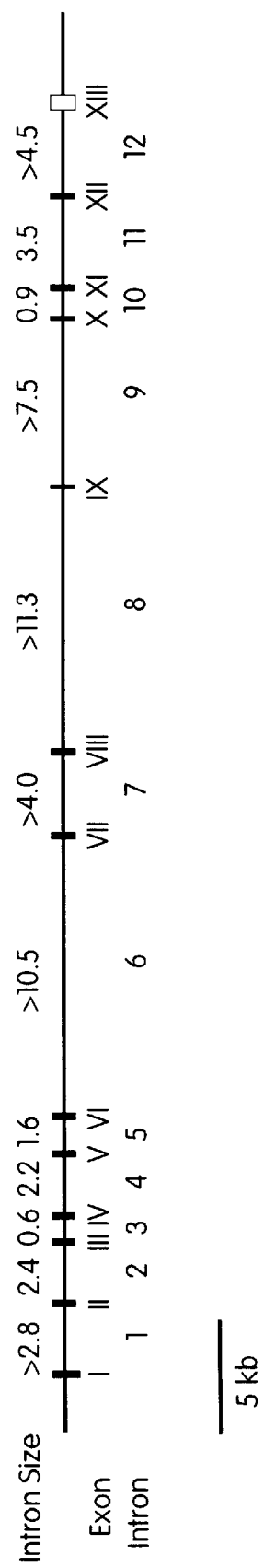
Figure 4:
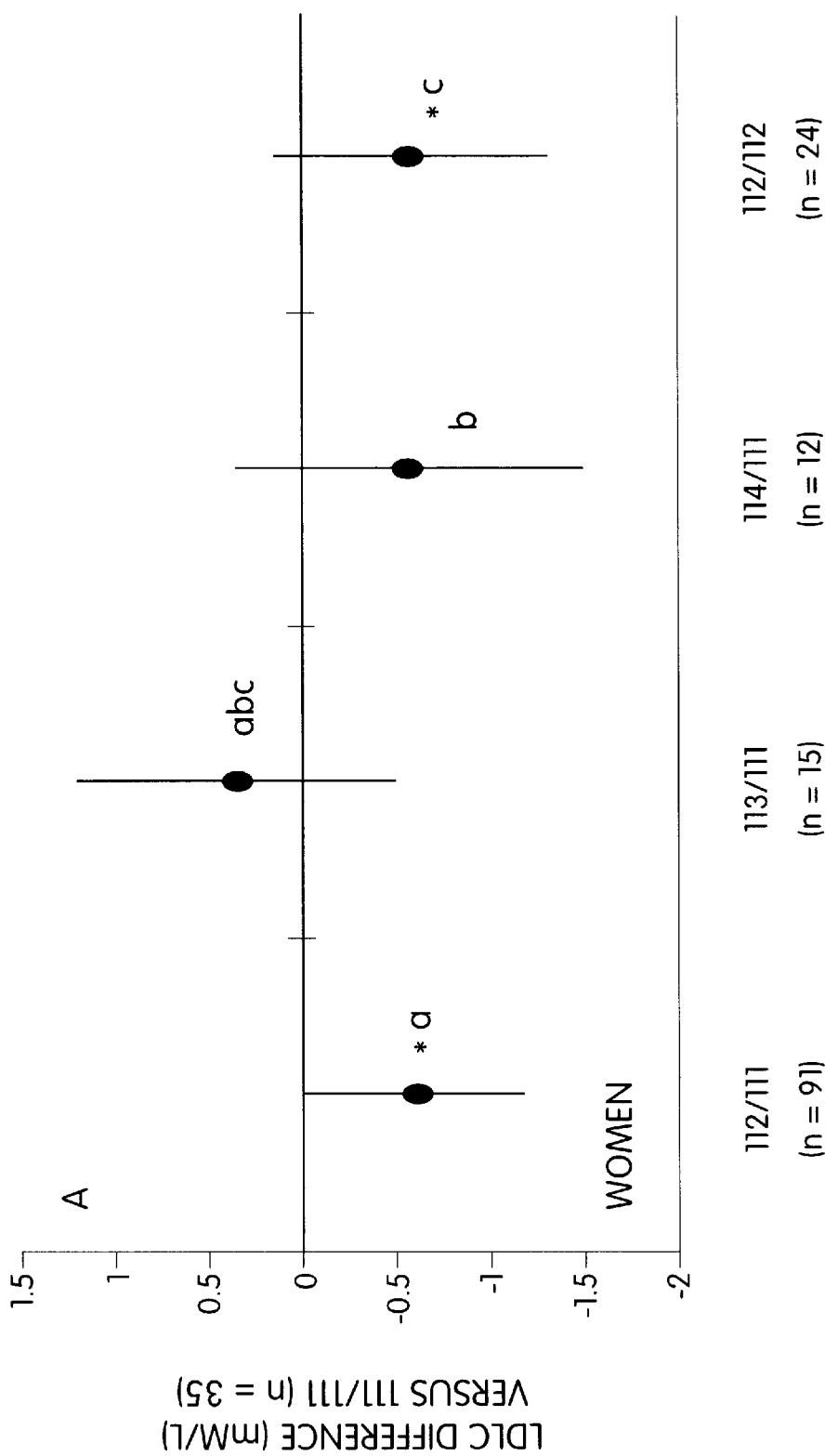
Figure 5:
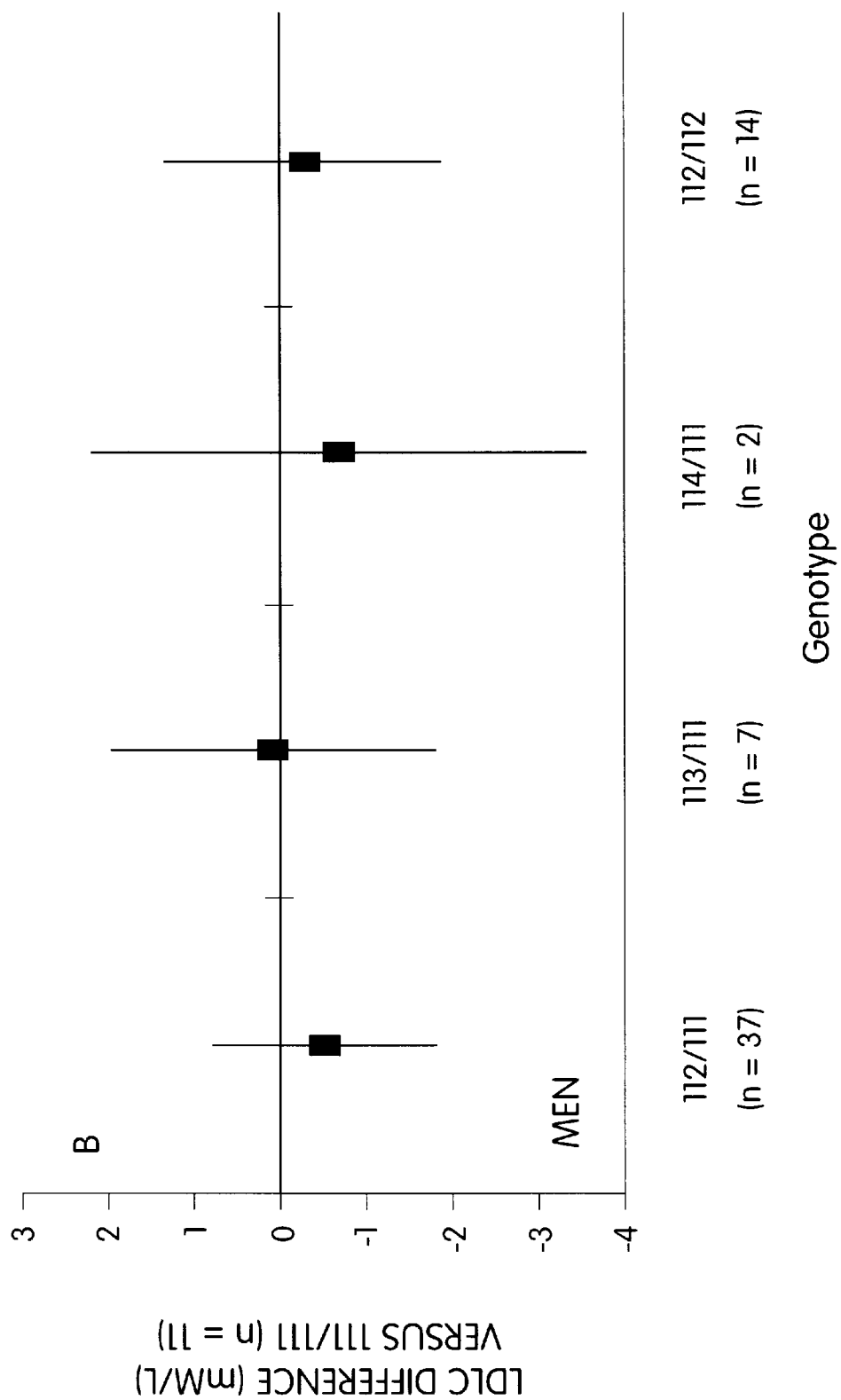
Figure 6:
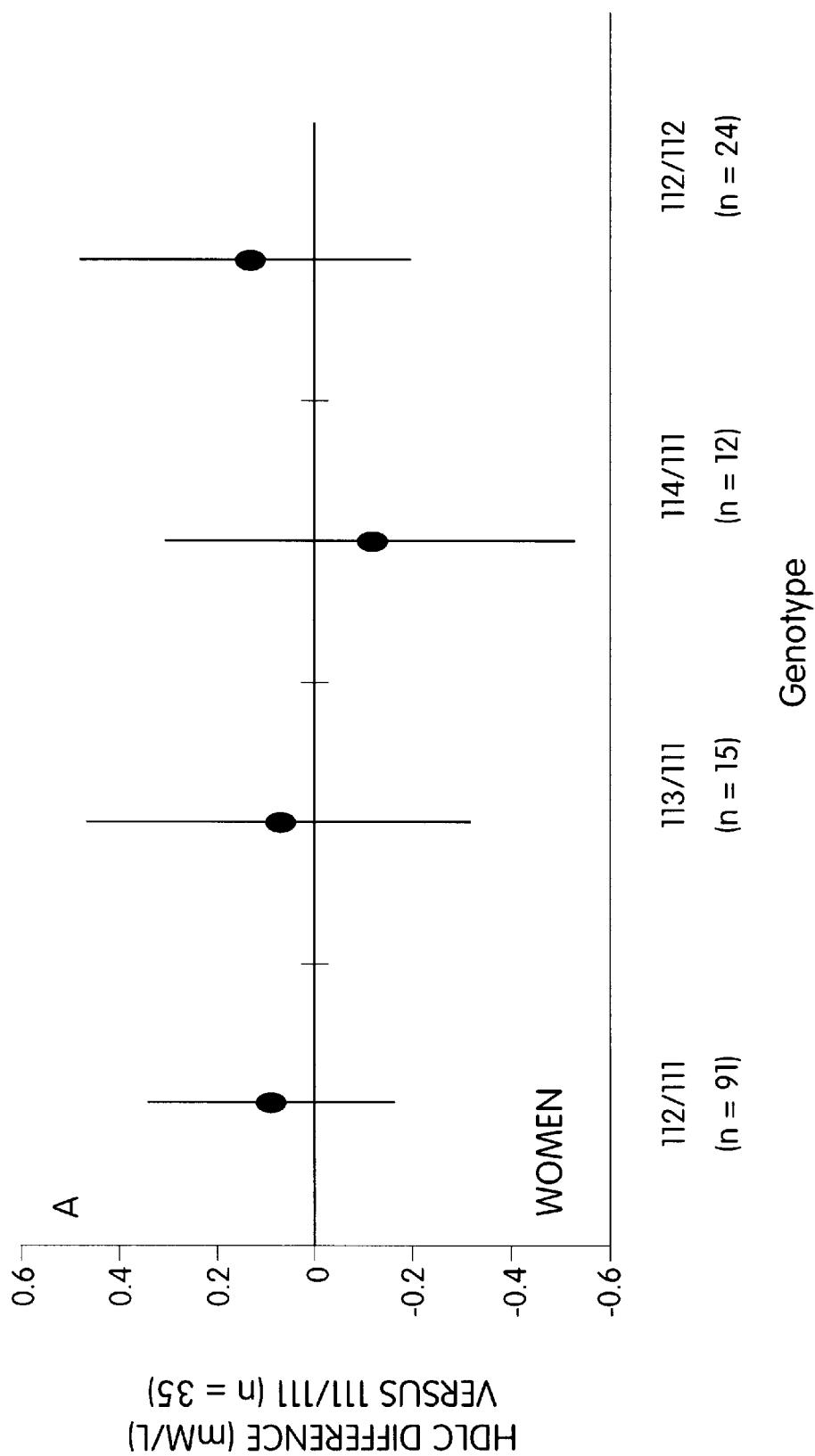
Figure 7:
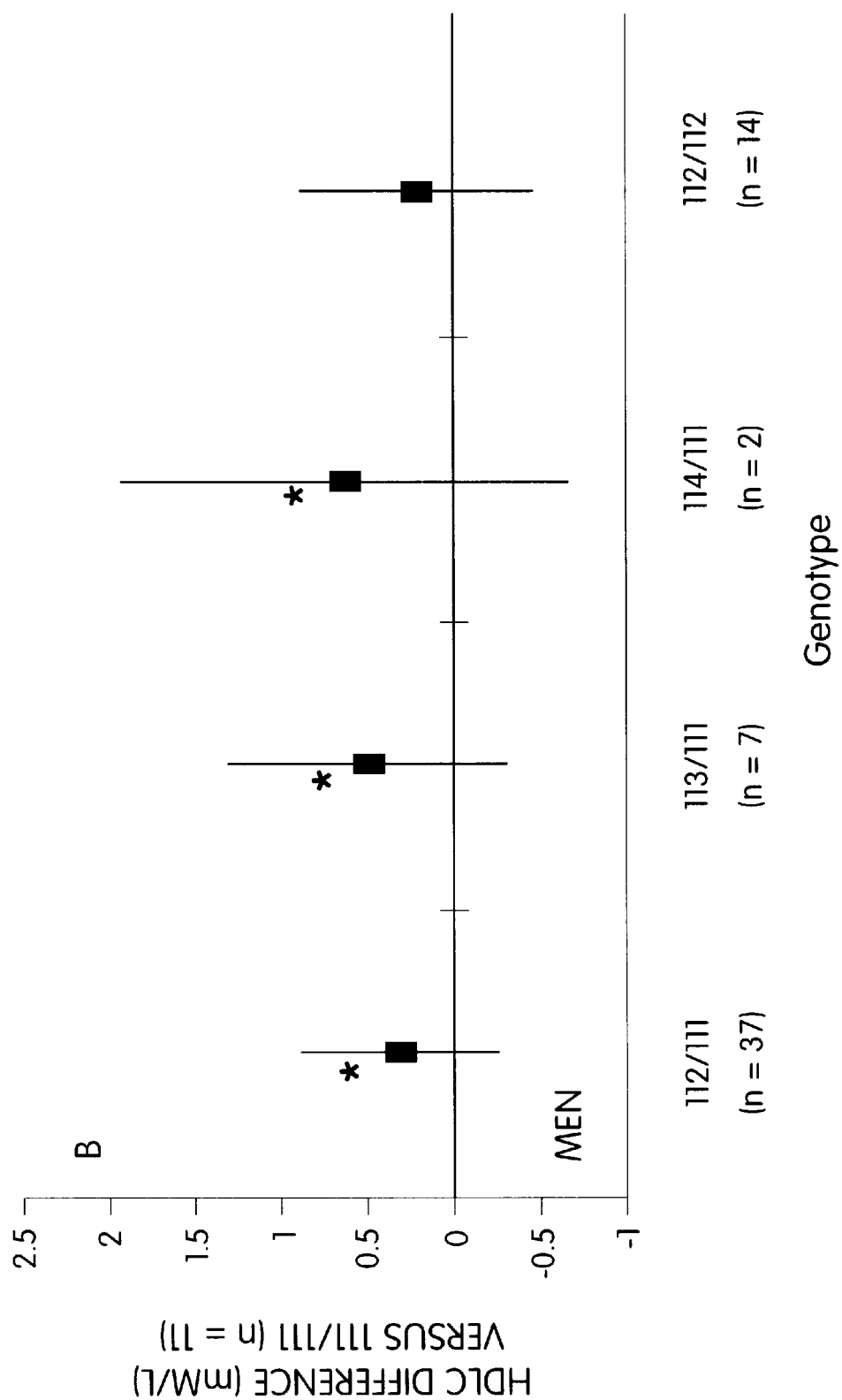
Figure 8:
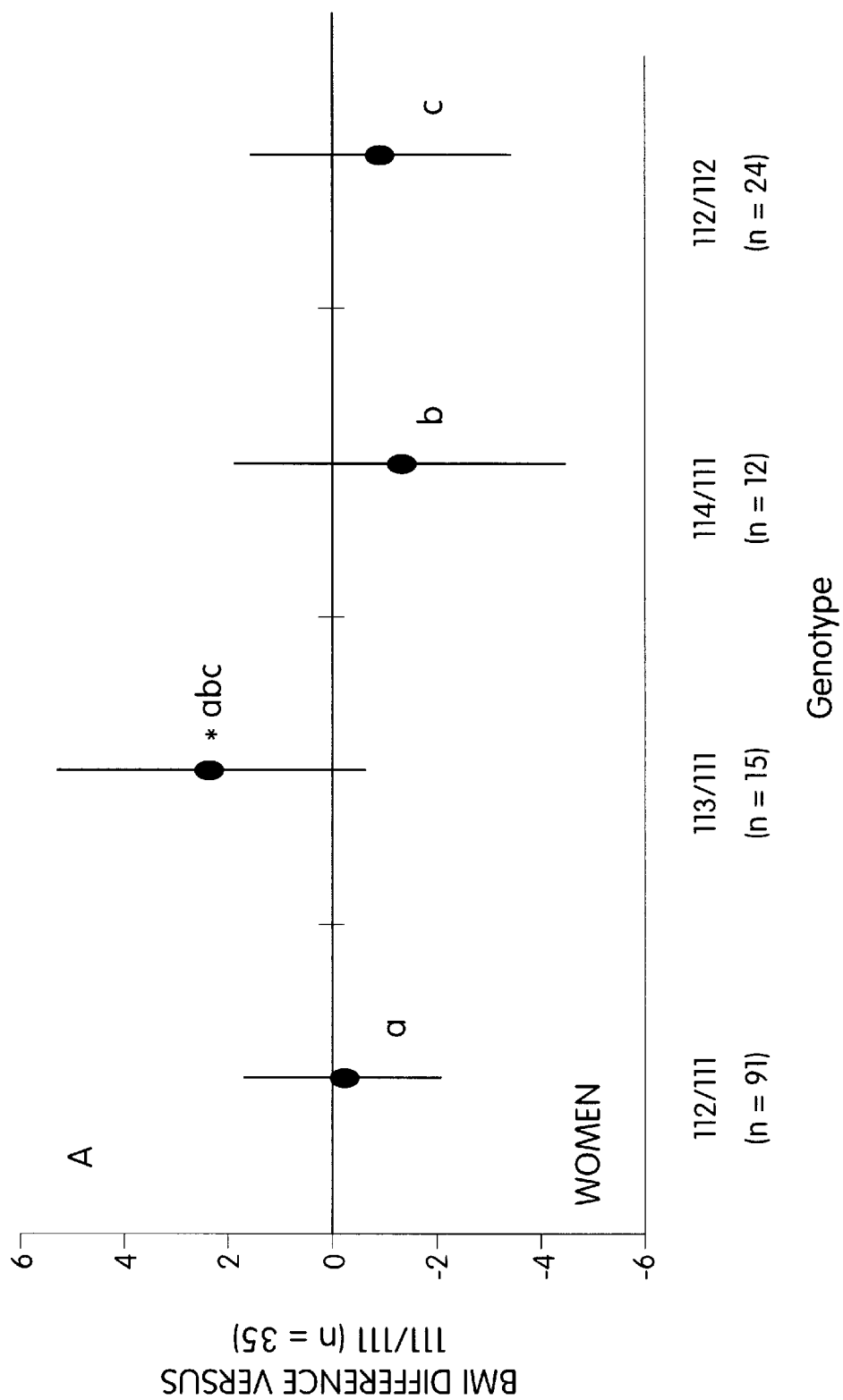
Figure 9:
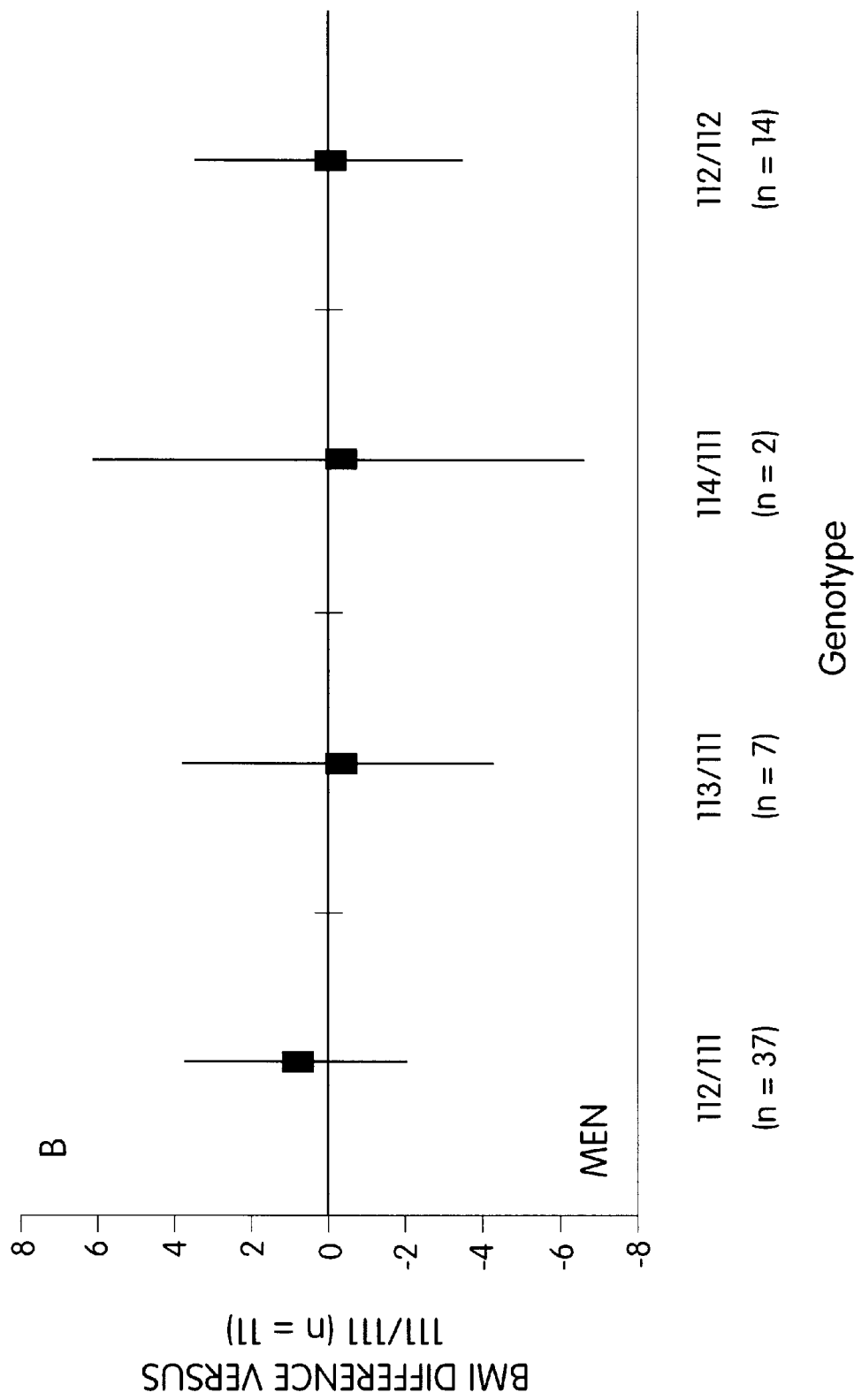

United States Patent [19]
Acton

[11] Patent Number: 5,998,141
[45] Date of Patent: Dec. 7, 1999

[54] INTRONIC AND POLYMORPHIC SR-BI NUCLEIC ACIDS AND USES THEREFOR

[75] Inventor: Susan Laurene Acton, Lexington, Mass.

[73] Assignee: Millennium Pharmaceuticals, Inc., Cambridge, Mass.

[21] Appl. No.: 08/890,980

[22] Filed: Jul. 10, 1997

[51] Int. Cl.[6] .............................. C12Q 1/68; C12P 19/34; C07H 21/04
[52] U.S. Cl. ........................... 435/6; 435/91.1; 435/91.2; 536/23.1; 536/24.31; 536/24.33
[58] Field of Search .............................. 435/6, 91.1, 91.2, 435/810; 536/23.1, 24.31, 24.33

[56] References Cited

FOREIGN PATENT DOCUMENTS

| | | |
|---|---|---|
| WO 96/00288 | 1/1996 | WIPO . |
| WO 97/02048 | 1/1997 | WIPO . |
| WO 97/18304 | 5/1997 | WIPO . |
| WO 98/39431 | 9/1998 | WIPO . |

OTHER PUBLICATIONS

Cao et al., J. Biol. Chem. 272(52), 33068–33076 (Dec. 1997).
Hillier, L. et al. "The WashU–Merck EST project (AC H22816)" EMEST13, 1995, XP002095407, Heidelberg.
Hillier, L. et al. "The WashU–Merck EST project (AC T39475)" EMEST13, 1995, XP002095408, Heidelberg.
Hillier, L. et al. "The WashU–Merck EST project (AC R59536)" EMEST13, 1995, XP002095409, Heidelberg.
Sanger, F. et al. "DNA Sequencing with Chain–Terminating Inhibitors" *PNAS*, 74(12):5463–5467, Dec. 1977, XP000604551.
Botstein, D. et al. "Construction of a Genetic Linkage Map in Man Using Restriction Fragment Length Polymorphisms" *Am. J. Hum. Gen.* 32(3):314–331, May 1980,. XP000610566.
Orita, M. et al. "Detection of Polymorphisms of Human DNA by Gel Electrophoresis as Single–Strand Conformation Polymorphisms" *PNAS* 86(8):2766–2770, Apr. 1989, XP000310584.
Saiki, R.K. et al. "Genetic Analysis of Amplified DNA with Immobilized Sequence–Specific Oligonucleotide Probes" *PNAS* 86(16):6230–6234, Aug. 1989, XP000268602.
Nickerson, D. et al. "Automated DNA Diagnostics Using an ELISA–Based Oligonucleotide Ligation Assay" *PNAS* 87(22):8923–8927, Nov. 1990, XP000209335.
Ganguly, A. et al. "Detection of Single–Based Mutations by Reaction of DNA Heteroduplexes with a Water–Soluble Carbodiimide Followed by Primer Extension: Application to Products from the Polymerase Chain Reaction" *Nuc. Acids Res.* 18(13):3933–3939, 1990, XP002033171.
International Search Report for PCT/US98/14359, dated Mar. 16, 1999.
Frossard, P.M. et al. "ApaI RFLP 5.4 kn 5' to the human apolipoprotien AI (APO A1)gene" *Nuc. Acids Res.* 14(4), 1986, XP002090828.

(List continued on next page.)

*Primary Examiner*—Kenneth R. Horlick
*Attorney, Agent, or Firm*—Foley, Hoag & Eliot LLP; Beth E. Arnold, Esq.; Isabelle M. Clauss, Ph.D

[57] ABSTRACT

The present invention is based at least in part on the discovery of the genomic structure of the human SR-BI gene and on the identification of polymorphic regions within the gene. Accordingly, the invention provides nucleic acids having a nucleotide sequence of an allelic variant of an SR-BI gene and nucleic acids having an SR-BI intronic sequence. The invention also provides methods for identifying specific alleles of polymorphic regions of an SR-BI gene, methods for determining whether a subject has or is at risk of developing a disease which is associated with a specific allele of a polymorphic region of an SR-BI gene, and kits for performing such methods.

52 Claims, 18 Drawing Sheets

OTHER PUBLICATIONS

Varban, M.L. et al. "Targeted mutation reveals a central role for SR–B1 on hepatic selective uptake of high density lipoprotein cholesterol" *PNAS* 95:4619–4624, Apr. 1998, XP002090830.

Rigotti, A. et al. "Targeted mutation of the gene encoding SR–B1 establishes that it plays a key role in HDL metabolism" *FASEB Journal* 1(9):A1292, 1997, XP002090831.

Acton, S.L. et al. "Expression Cloning of SR–BI, a CD36–related Class B Scavenger Receptor" *J. Biol. Chem.* 269(33):21003–21009, 1994.

Acton, S. et al. "Identification of Scavenger Receptor SR–BI as a High Density Lipoprotein Receptor" *Science* 271:518–520, 1996.

Calvo, D. and Vega, M.A. "Identification, primary structure, and distribution of CLA–1, a novel member of the CD36/LIMPH gene family" *J. Biol. Chem.* 268(25):18929–18935, 1993.

Calvo, D. et al. "The CD36, CLA–1 (CD36L1), and LIMPII (CD36L2) Gene Family: Cellular Distribution, Chromosomal Location, and Genetic Evolution" *Genomics* 25:100–106, 1995.

Fukasawa, M. et al. "SBR1, a Class B scavenger receptor, recognizes both negatively charged liposomes and apoptotic cells" *Exper. Cell Research* 222:246–250, 1996.

Rigotti, A. et al. "The Class B Scavenger Receptors SR–BI and CD36 are Receptors for Anionic Phospholipids" *J. Biol. Chem.* 270 (27):16221–16224, 1995.

Tang, Y. et al. "Identification of a Human CD36 Isoform Produced by Exon Skipping" *J. Biol. Chem* 269 (8):6011–6015, 1994.

Wang, N. et al. "Scavenger Receptor BI (SR–BI) is up–regaulated in adrenal gland in apolipoprotein A–I and hepatic lipase knock–out mice as a response to depletion of cholesterol stores" *J. Biol. Chem* 271 (35):21001–21004, 1996.

promoter and exon 1

ACTGCGGAGATGAGGGTCTAGAAGGTGGTGGCGGGGCAT
GTGGACCGTTGTAAGGGCTCTGGGG**TTCCTGGGTGGGCT
GGCGAAGTCCTACTCACAGTGACCAACCATGATGATGGT
CCCGATAGAGGAGGAGAGGGAGGAGGAGGGAAAAGGAAG
GGTGAGGGGCTCAGAGGGGAGAGCTGGGAGGAGGGGAGA
CATAGGTGGGGAAGGGGTAGGAGAAAGGGGAAGGGAGC
AAGAGGGTGAGGGGCACCAGGCCCATAGACGTTTTGGC
TCAGCGGCCACGAGGCTTCATCAGCTCCCGCCCGAAAAC
GGAAGCGAGGCCGTGGGGCAGCGGCAGCATGGCGGGGC
TTGTCTTGGCGGCCATGGCCCCGCCCCTGCCCGTCCGA
TCAGCGCCCCGCCCCGTCCCCGCCCCGACCCCGCCCGG
GCCCGCTCAGGCCCCGCCCCTGCCGCCGGAATCCTGAAG
CCCAAGCTGCCCGGGGCGGTCCGGCGGCGCCGGCGAT
GGGGCATAAAACCACTGGCCACCTGCCGGGCTGCTCC

<u>TGCGTGCGCTGCCGTCCCGGATCCACCGTGCCTCTGCGG
CCTGCGTGCCCGGAGTCCCCGCCTGTGTCGTCTCTGTCG
CCGTCCCCGTCTCCTGCCAGGCGCGGAGCCCTGCGAGCC
GCGGGTGGGCCCCAGGCGCGCA**GACATGAGCTGCTCCGC
CAAAGCGCG**CTGGGCTGCCGGGGCGCTGGGCGTCGCGGG
GCTACTGTGCGCTGTGCTGGGCGCTGTCATGATCGTGAT
GGTGCCGTCGCTCATCAAGCAGCAGGTCCTTAAG</u>

GTGGGTGAGGGAGACCCAGGGGGTCCGCGCACGGACCC
GGGCTGTTGGGCGCTGGGCGCCGGGAGGACCCGCGCGTT
GCGGTGGGTGGGCGACCGCAGCGGAATCGGCGCCCGGGC
CTGGCGCCGCAGAACACGAGGGAGGCCAGGCGCTTCGGG
AGGGGCTGCTGCCGCCTCCCCACCACCCTCACC

Fig. 2A exon 2

AGCCTCATGTGCGAAGGGCTTTCCCACCACCTCCTATCC
CAAGCTCCCGCCGAGGAGCCCCTTCCCTGGCCGGGCTCG
GGCAGCTGTTCCGGAGCCTTGTGGTGGGGCG**TGGGGCC
CTCATCACTCTCCTCA**CAAGCGTACTTGTCCCTTCCC
CTGCAG

<u>AACGTGCGCATCGACCCCAGTAGCCTGTCCTTCAACATG</u>
<u>TGGAAGGAGATCCCTATCCCCTTCTATCTCTCCGTCTAC</u>
<u>TTCTTTGACGTCATGAACCCCAGCGAGATCCTGAAGGGC</u>
<u>GAGAAGCCGCAGGTGCGGGAGCGCGGGCCCTACGTGTAC</u>
<u>AG</u>

GTGAGGCTGTGTCCACGTGATGGTGGACGGGCCGGCTGA
CGCTGGGCATGGGACGGGTCTCAN**AGTGGACGGGATG
GGGAGGCTGC**TGACTGACCCCAAACATTGTTCCGGAA
GCACGCAACTCATAGTCGGGGTAAGTGCTACTCCCAAAA
AAGTTTGCGT exon 3

CATGTCCTGCAGTGGGCAGGCAGCGGGAGGGACAGACTT
GGCGAAGGGGCCGAGCTCAGCTTTGGCTGTGGGGCCGGA
GGTGTGCACAGACGTCCAGGGCCCCTGGTTCCCAGGCAG
GCATTGCAGGCGAGTAGAAGGGAAACGTCCCATGCAG
CGGGGCGGGGCGTCTGACCCACTGGCTTCCCCCACAG

<u>GGAGTTCAGGCACAAAAGCAACATCACCTTCAACAACAA</u>
<u>CGACACCGTGTCCTTCCTcGAGTACCGCACCTTCCAGTT</u>
<u>CCAGCCCTCCAAGTCCCACGGCTCGGAGAGCGACTACAT</u>
<u>CATCATGCCCAACATCCTGGTCTTG</u>

GTGAGGCTGCCCTGTGGCCCACGCCGCCTCGCACCCTGA
CCTCGTCCCCTGTCTCTCCTCCCGCCTGCCCTTGTG
CAGAGAGCAGTCCCTGAGGTGGTCGGAGCGTGGGGACTC
ACGCCTGGTGGGTGGCTTTCGGCCCTGTGCTGTCTCCAC
CACCCCCA

Fig. 2B exon 4

GGTGGTTCTGGTGTCCCAGATGCCCACGTGGCCACTCC
AGGGGCCTCCTGCACCCCAGCATTTCCCTTCA**TGGGCT
CTTTGCTGTGAGGC**CCAGCTGGGGCCAAGGGAGGATG
GGCCAGCCACGTCCAGCCTCTGACACTAGTGTCCCTTCG
CCTTGCAG

<u>GGTGCGGCGGTGATGATGGAGAATAAGCCCATGACCCTG</u>
<u>AAGCTCATCATGACCTTGGCATTCACCACCCTCGGCGAA</u>
<u>CGTGCCTTCATGAACCGCACTGTGGGTGAGATCATGTGG</u>
<u>GGCTACAAGGACCCCTTGTGAATCTCATCAACAAGTACT</u>
<u>TTCCAGGCATGTTCCCCTTCAAGGACAAGTTCGGATTAT</u>
<u>TTGCTGAG</u>

GTACGTGTGGCCTGGTGAGAAGCCAAAGATTCAGGCCTG
TGTCCTGTCTTCCCCTCACACAGCCTGGACACTGGTC
ACCAGCTTGCTTTGTAGCTGGCTGGGGATCTAGTGGCTG
TGGGTTGTAAGTGACTGAGAACCTGACTCAAACCGGCTT
GAGTGAAA exon 5

CCTCTCGGTCCCCAGACACTGGGCATTTGGCAGTGAACC
AGATGCTGGGGGCCCTGTCCTTCTGGTGGAGGGGGAGGA
GGGCTCAGCCCAGAATGTTCAGACCAGGCCGGCTCAA
TGGCAGGCCTAAGCCTTACGATGCTGTTCCCTGCTGTGT
CTGTAG

<u>CTCAACAACTCCGACTCTGGGCTCTTCACGGTGTTCACG</u>
<u>GGGGTCCAGAACATCAGCAGGATCCACCTCGTGGACAAG</u>
<u>TGGAACGGGCTGAGCAAG</u>

GTGAGGGGCGAGAGGCGAGGGCCCCTGTCGCCAGGGAGA
GGGGAGGGTGGGCCTGGCCATGGCTGCTCGGGAGTGGCA
GGGACCAGAGAGCTCCTTCTTC**CTTTGTCGTGAAGAG
GGTGC**TGGGAGGATGAACACTCTTGAAGTTGGAGGAGGG
ATTTTA

Fig. 2C exon 6

TCTCTGTGTGTCTACATAGCCTGCCCTCTTCCCACCGTG
CCAGTATTGGGAATTGAGTGGCCGTGCGTGCACCAGGGT
GAGTTAGGTGTGCAGCACCTGAGAGGGCTTATTAAGG
GGCCTTGGCCCTACTGAGGGGTCTAGTCTGGATGCTTCC
CCCCAG

GTTGACTTCTGGCATTCCGATCAGTGCAACATGATCAAT
GGAACTTCTGGGCAAATGTGGCCGCCCTTCATGACTCCT
GAGTCCTCGCTGGAGTTCTACAGCCCGGAGGCCTGCCG

GTAATCACTGGGACTCGGGGCCTCCTGGGTTTCCTGGGT
AGCTCATGGCCAAATTCTGTGGTGTTGGCTGT**GCACTT
GGAAAGCATTTTG**ACTCATCGTGGATTTGACTCAGTAG
CCCTTGGCACCAGCTTGAATTCTCTTTGGTCACACCACC
AAAAGC exon 7

GGAGGTCGCTGCAGCTCCGCGGGTGAGAGATGGGGGCGG
TTTGGACCCGGGAGGTGGTAGCGCCCGTGGGGAGAAGTG
GCTGGATCTGGGCAGCCTTTGGCAGGGCCTGGCTCTG**GC
CGCCGGGTCTGGGTGTCC**CCTCTCATCCTGTCTGTCC
CCTGCAG

ATCCATGAAGCTAATGTACAAGGAGTCAGGGGTGTTTGA
AGGCATCCCCACCTATCGCTTCGTGGCTCCCAAAACCCT
GTTTGCCAACGGGTCCATCTACCCACCCAACGAAGGCTT
CTGCCCGTGCCTGGAGTCTGGAATTCAGAACGTCAGCAC
CTGCAGGTTCA

GTACGTGCCGTCCCTGTTCTGGGATNGCCGGAGGGTGT
TAGGTNTNGGGCACCTNAGGTTTATCTGCCCAATGCT**G
TCTGCTTAATCTCTGGCCTCTG**TACTCTTGATAACC
CATTAAGCCAAAAATATGATGCCTCTGGGACGATATCTG

Fig. 2D exon 8

TGGGGCTTTTTACAGAATGGAGGAAGGGATCCTCTCT
GTCGGGTATTATGGTCATCGCCACGGGGGTGCCGTGCAG
ACCACAGCTCTGTGCAGACTTCCGGAGTGGCAGGACGTG
CCAATATACTGTCGTTGTATGATGTCCCCTCCCTGCCCT
TGTTGTAG

<u>GTGCCCCCTTGTTTCTCTCCATCCTCACTTCCTCAACG</u>
<u>CCGACCCGGTTCTGGCAGAAGCGGTGACTGGCCTGCACC</u>
<u>CTAACCAGGAGGCACACTCCTTGTTCCTGGACATCCACC</u>
<u>CG</u>

GTGAGCCCCTGCCATCCTCTGTGGGGGGTGGGTGATTCC
TGGTTGGAGCACACCTGGCTGCCTCCTCTCTCCCCAG
GCAGAGAGCTGCTGTGGGCTGGGGTGGTGGGAAGCCTGG
CTTCTAGAATCTCGAGCCACCAAAGTTCCTTACT exon 9

CCCCAGCCTGTGGCTTGTTTTAGGTAAGATACAAGCAAG
CTCCACTGGGCAGTTAGCTGGGACGCCCACCCTCTTGAC
TGGGACCAGGGAAAAGAAGGTTGACTGTGTCCCTGGA
GCTTGGGGGTGGCCAGTCTCCTCACTGTGTTTGTTGCCG
CAG

<u>GTCACGGGAATCCCCATGAACTGCTCTGTGAAACTGCAG</u>
<u>CTGAGCCTCTACATGAAATCTGTCGCAGGCATTGG</u>

GTGAGTGGGGACTGGGAACTGGGGCTGCATTGCTCATTG
AGAGATTANGTGCTCAGTGCTCCAGTGTTCCCAGAC
TCCCCTGACATACCCCAGGAACAGGGCATGGGGAAGGG
AGAGGGTCCTATTGGGGGTGGAATCCAGTCCCTGCTGAT
CTTCTC

Fig. 2E exon 10

ATGGCTCCTAAAGTGTTTCAGCTCATTGTTTATATTT**GG
TGGTGAGGGTTTAGTGTG**TGCAAAATTATACTAAACC
TGTTTAGATGTTGTATTCAAGCAGAATTAGATCAAGTTT
GGGTGTAAGACTTTGTTCCACACCTATGTCTTGCTTAT
TTCCAG

<u>ACAAACTGGGAAGATTGAGCCTGTGGTCCTGCCGCTGCT
CTGGTTTGCAGAG</u>

GTAAGGGTGCGTTGGGCACAGCGTCGGGGGCTTTTGTTA
ATAGCCAATGTGGGCATTT**GAGGCAGGAGGCGGGGGG
AG**CACCTTGTAGAAGGGAGAGGGCTGAGCCAGGGTAAC
CGGACTGTTACATGGACCAGCGTATCATACACTTCACCC
TGTC exon 11

CCTGGAGGGAGGAGGTCCCTGGCAGGCTCCAACACATGC
TTTAGCCGGGAAGCTTGAGGTGGGGAAAAGCTGAGGCGG
GCACAGAGGAAGGTGTTGGGTGGCATCTGCGCTGTAG
CCCGCAGCGTGCGGCCCCAGCTCATGTGTTTGTCATTCT
GTCTCCTCAG

<u>AGCGGGGCCATGGAGGGGGAGACTCTTCACACATTCTAC
ACTCAGCTGGTGTTGATGCCCAAGGTGATGCACTATGCC
CAGTACGTCCTCCTGGCGCTGGGCTGCGTCCTGCTGCTG
GTCCTGTCATCTGCCAAATCCGGAGCCAA</u>

GTAGGTGCTGGCCAGAGGGCAGCCCGGGCTGACAGCCAT
TCGCTTGCCTGCTGGGGAAAGGGGCCTCAGATCGGACC
CTCTGGCCAACCGCAGCCTGGAGCCCACCTCCAGCAG
CAGTCCTGCGTCTCTGCCGGAGTGGGAGCGGTCACTGCT
GGGGG

Fig. 2F exon 12

CCCCACATCTCAGCCACCTGCAATCGTTGAGGGTTGTTG
GACTCTAAACTTATGTGCCTTTCCTGTTTCCTCTTTGCC
TTTTGCAAATTGAAGAACCGTGTAAAACCATTTTTAT
GTGGCTTCAACGTCAACTATAAATTAGCTTGGTTATCTT
CTAG

<u>GAGAAATGCTATTTATTTTGGAGTAGTAGTAAAAGGGC</u>
<u>TCAAAGGATAAGGAGGCCATTCAGGCCTATTCTGAATCC</u>
<u>CTGATGACATCAGCTCCCAAGGGCTCTGTGCTGCAGGAA</u>
<u>GCAAAACTGTAG</u>

GTGGGTACCAGGTAATGCCGTGCGCCTCCCGCCCCCTC
CCATATCAAGTAGAATGCTGGCGGCTTAAAACATTTGGG
GTCCTGCTCATTCCTTCAGCCTCAACTTCACCTGGAG
TGTCTACAGACTGAAGATGCATATTTGTGTATTTTGCTT
TTGGAGAAA

Fig. 2G

```
                                                                                                   79
ACCGTGCCTCTGCGGCCTGCGGTGCCCGGAGTCCCCGCCTCTCCTGTCGCCCGTCCTCCTGCCAGGCGCG

M   G   C   S   A   K   A   R   W   A        10
GAGCCCTGCGAGCCGCGGGTGGGCGCCCCAGGCGCGCAGAC ATG GGC TGC TCC GCC AAA GCG CGC TGG GCT   148
                       exon 1
L   A   G   V   L   C   A   V   L   G   A   V   M   I   V        30
CTA CTG TGC GCT GTG CTG GGC GCT GTC ATG ATC GTG                                      208
                                 exon 2
V   P   V   R   I   P   F   Y   S            50
Q   Q   V   N   K   P   I   D   P   S         
CAG CAG GTC AAC AAG CTT AAG CCC ATC GAC CCC AGT AGC                                   268

L   S   L   I   K   E   F   Y   E   R   G        70
CTC TCG CTC ATC AAG GAG TGG AAG GAG ATC CTC TCC TAT TCC GAG CCC GGG                   328
                       exon 3

D   V   M   N   P   S   E   K   Q   I   T   F   N   N   D   T       110
GAC GTC ATG AAC CCC AGC GAG ATC CTG AGG TTC CAG ACC TTC AAC AAC GAC ACC               448

P   Y   V   Y   R   E   F   Y   R   T   F   Q   P   S   K   A   G   S   E       130
CCC TAC GTG TAC AGG GAG TTC TAC CGC ACC TTC CAG CCC TCC AAG GCG TCG GAG               508
                                                           exon 4
V   S   F   L   M   I   M   P   N   L   V   L   G   A   A   V   M       150
GTG TCC TTC CTC ATG ATC ATG CCC AAC CTC GTC TTG GGT GCG GCG GTG ATG                   568

S   D   Y   I   V   T   L   A   F   T   L   T   G   E   R   A       170
AGC GAC TAC ATC GTC ACC CTG AAG CTT GCA TTC ACC CTC GGC GAA CGT GCC                   628

K   P   M   T   L   K   T   M       
AAG CCC ATG ACC CTG AAG ACC ATG

Fig. 3A-1
```

Fig. 3A-2

```
F   L   D   I   H   P   M   P   I   G   T   G   M   N   C   S   V   K   L   Q   L    390
TTC CTG GAC ATC CAC CCG ATC GGA ACG GGA ATG AAC TGC TCT GTG AAA CTG CAG CTG        1288
                                              →exon 9                              →exon 10

S   L   Y   M   K   S   V   A   G   I   Q   T   G   K   I   E   P   V   V   T   F    410
AGC CTC TAC ATG AAA TCT GTC GCA GGC ATT GGA CAA ACT GGG AAG ATT GAG CCT GTG ACA TTC 1348
                                              →exon 11

L   P   L   W   P   A   E   S   G   A   M   E   G   E   T   L   M   H   T   F        430
CTG CCG CTC TGG CCA TTT GCA GAG AGC GGG GCC ATG GAG GGG GAG ACT CTT CAC ACA TTC    1408

Y   T   Q   L   V   L   M   P   K   V   M   H   Y   A   Q   Y   V   L   L   A        450
TAC ACT CAG CTG GTG TTG ATG CCC AAG GTG ATG CAC TAT GCC CAG TAC GTC CTC CTG GCG    1468

L   G   C   V   L   L   L   V   P   V   I   C   Q   R   S   E   A   I   R   C        470
CTG GGC TGC GTC CTG CTG CTG GTC CCT GTC ATC TGC CAA CGG AGC GAG GCC ATC CGG TGC    1528
                                                          →exon 12

Y   L   F   W   S   S   S   K   K   G   P   K   A   D   K   E   S   V   L   Q        490
TAT TTA TTT TGG AGT AGT AGT AAA AAG GGC CCC AAG GCT GAT AAG GAG TCA GTG CTG CAG    1588
                                                                              →exon 12

S   E   S   L   M   T   S   A   P   P   K   G   S   V   E   A   K   L   A   Y   *    510
TCT GAA TCC CTG ATG ACA TCA GCT CCC AAG GGC TCT GTG GAA GCA AAA CTG GCC TAT TAG    1648

GCTCCTGAGGACACCGTGAGCCAGGCCTGGCCGCTGGGCCCCCCAGCCGGACCCGCCCCTACACCCGCTTCTCC         1727

CGGACTCTCCCAGCAGACAGCCCCCAGCCCTCCCCAGCCTGAGCCTCCCCAGTGCCCATGTCCCCTGTTGCACACCTGCACA 1806

CACGCCCTGGCACACATACACACATGCGTGCAGGCTTGTGCAGACACTCAGGGATGGAGCTGCTGCTGAAGGGACTTGT    1885
```

Fig. 3B-1

```
AGGGAGAGGCTCGTCAACAACCACTGTTCTGGAACCTTCTCTCCACGTGGCCCACAGGCCTGACCACAGGGGCTGTGGG    1964
TCCTGCGTCCCCTTCCTCGGGTGAGCCTGGCCTGTCCCGTTCAGCCGTTGGGCCCAGGCTTCCTCCCCTCCAACGTGAA    2043
ACACTGCAGTCCCGGTGTGGCTCCCCATGCAGGACGGCCAGGCTGGGAGTGCCGCCTTCCTGTGCCAAATTCAGT        2122
GGGGACTCAGTGCCCAGGCCCCTGGCCCACGAGCTTTGGCCTTGGTCTACCTGCCAGGCCAAAGCGCCTTTACACAG      2201
GCCTCGGAAAACAATGGAGTGAGCACAGATGCCCTGTGCAGCTGCCCGAGGGTCTCCGCCCACCCCGGCCGACTTTG      2280
ATCCCCCGAAGTCTTCACAGGCACTCCATCGGGTTGTCTGGCGTTTTCCTCCAGCCTAAACTGACATCATCCTAT        2359
GGACTGAGCCGGCCACTYTYTGGCCGAAGTGGCCCAGGCTGTGCCCCCGAGCTGCCCCACCCCCTCACAGGGTCCCT      2438
CAGATTATAGGTGCCCAGGCTGAGGTGAAGAGGCCTGGGGGCCCTGCCTTCCGGCCGCTCCTGGACCCTGGGGCAAACC    2517
TGTGACCCTTTTCTACTGGAATAGAAATGAGTTTATCATCTTTGAAAAATAATTCACTCTTGAAGTAATAAACGTTTA     2596
AAAAAATGGGAAAAAAAAAAAAAAAAAAAAAA                                                    2630
```

Fig. 3B-2

SEQUENCE LISTING (1) GENERAL INFORMATION:

(iii) NUMBER OF SEQUENCES: 86

(2) INFORMATION FOR SEQ ID NO:1:

(i) SEQUENCE CHARACTERISTICS:
      (A) LENGTH: 2630 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 119..1645

(xi) SEQUENCE DESCRIPTION: SEQ ID NO:1:

```
ACCGTGCCTC TGCGGCCTGC GTGCCCGGAG TCCCCGCCTG TGTCGTCTCT GTCGCCGTCC        60

CCGTCTCCTG CCAGGCGCGG AGCCCTGCGA GCCGCGGGTG GGCCCCAGGC GCGCAGAC         118

ATG GGC TGC TCC GCC AAA GCG CGC TGG GCT GCC GGG GCG CTG GGC GTC        166
Met Gly Cys Ser Ala Lys Ala Arg Trp Ala Ala Gly Ala Leu Gly Val
```

```
          1               5               10              15
GCG GGG CTA CTG TGC GCT GTG CTG GGC GCT GTC ATG ATC GTG ATG GTG     214
Ala Gly Leu Leu Cys Ala Val Leu Gly Ala Val Met Ile Val Met Val
             20                  25                  30

CCG TCG CTC ATC AAG CAG CAG GTC CTT AAG AAC GTG CGC ATC GAC CCC     262
Pro Ser Leu Ile Lys Gln Gln Val Leu Lys Asn Val Arg Ile Asp Pro
         35                  40                  45

AGT AGC CTG TCC TTC AAC ATG TGG AAG GAG ATC CCT ATC CCC TTC TAT     310
Ser Ser Leu Ser Phe Asn Met Trp Lys Glu Ile Pro Ile Pro Phe Tyr
     50                  55                  60

CTC TCC GTC TAC TTC TTT GAC GTC ATG AAC CCC AGC GAG ATC CTG AAG     358
Leu Ser Val Tyr Phe Phe Asp Val Met Asn Pro Ser Glu Ile Leu Lys
 65                  70                  75                  80

GGC GAG AAG CCG CAG GTG CGG GAG CGC GGG CCC TAC GTG TAC AGG GAG     406
Gly Glu Lys Pro Gln Val Arg Glu Arg Gly Pro Tyr Val Tyr Arg Glu
                 85                  90                  95

TTC AGG CAC AAA AGC AAC ATC ACC TTC AAC AAC AAC GAC ACC GTG TCC     454
Phe Arg His Lys Ser Asn Ile Thr Phe Asn Asn Asn Asp Thr Val Ser
             100                 105                 110

TTC CTC GAG TAC CGC ACC TTC CAG TTC CAG CCC TCC AAG TCC CAC GGC     502
Phe Leu Glu Tyr Arg Thr Phe Gln Phe Gln Pro Ser Lys Ser His Gly
         115                 120                 125

TCG GAG AGC GAC TAC ATC GTC ATG CCC AAC ATC CTG GTC TTG GGT GCG     550
Ser Glu Ser Asp Tyr Ile Val Met Pro Asn Ile Leu Val Leu Gly Ala
     130                 135                 140

GCG GTG ATG ATG GAG AAT AAG CCC ATG ACC CTG AAG CTC ATC ATG ACC     598
Ala Val Met Met Glu Asn Lys Pro Met Thr Leu Lys Leu Ile Met Thr
145                 150                 155                 160

TTG GCA TTC ACC ACC CTC GGC GAA CGT GCC TTC ATG AAC CGC ACT GTG     646
Leu Ala Phe Thr Thr Leu Gly Glu Arg Ala Phe Met Asn Arg Thr Val
                 165                 170                 175

GGT GAG ATC ATG TGG GGC TAC AAG GAC CCC CTT GTG AAT CTC ATC AAC     694
Gly Glu Ile Met Trp Gly Tyr Lys Asp Pro Leu Val Asn Leu Ile Asn
             180                 185                 190

AAG TAC TTT CCA GGC ATG TTC CCC TTC AAG GAC AAG TTC GGA TTA TTT     742
Lys Tyr Phe Pro Gly Met Phe Pro Phe Lys Asp Lys Phe Gly Leu Phe
         195                 200                 205

GCT GAG CTC AAC AAC TCC GAC TCT GGG CTC TTC ACG GTG TTC ACG GGG     790
Ala Glu Leu Asn Asn Ser Asp Ser Gly Leu Phe Thr Val Phe Thr Gly
     210                 215                 220

GTC CAG AAC ATC AGC AGG ATC CAC CTC GTG GAC AAG TGG AAC GGG CTG     838
Val Gln Asn Ile Ser Arg Ile His Leu Val Asp Lys Trp Asn Gly Leu
225                 230                 235                 240

AGC AAG GTT GAC TTC TGG CAT TCC GAT CAG TGC AAC ATG ATC AAT GGA     886
Ser Lys Val Asp Phe Trp His Ser Asp Gln Cys Asn Met Ile Asn Gly
                 245                 250                 255

ACT TCT GGG CAA ATG TGG CCG CCC TTC ATG ACT CCT GAG TCC TCG CTG     934
Thr Ser Gly Gln Met Trp Pro Pro Phe Met Thr Pro Glu Ser Ser Leu
             260                 265                 270

GAG TTC TAC AGC CCG GAG GCC TGC CGA TCC ATG AAG CTA ATG TAC AAG     982
Glu Phe Tyr Ser Pro Glu Ala Cys Arg Ser Met Lys Leu Met Tyr Lys
         275                 280                 285

GAG TCA GGG GTG TTT GAA GGC ATC CCC ACC TAT CGC TTC GTG GCT CCC    1030
Glu Ser Gly Val Phe Glu Gly Ile Pro Thr Tyr Arg Phe Val Ala Pro
     290                 295                 300

AAA ACC CTG TTT GCC AAC GGG TCC ATC TAC CCA CCC AAC GAA GGC TTC    1078
Lys Thr Leu Phe Ala Asn Gly Ser Ile Tyr Pro Pro Asn Glu Gly Phe
305                 310                 315                 320

TGC CCG TGC CTG GAG TCT GGA ATT CAG AAC GTC AGC ACC TGC AGG TTC    1126
Cys Pro Cys Leu Glu Ser Gly Ile Gln Asn Val Ser Thr Cys Arg Phe
```

```
                    325                 330                 335
AGT GCC CCC TTG TTT CTC TCC CAT CCT CAC TTC CTC AAC GCC GAC CCG     1174
Ser Ala Pro Leu Phe Leu Ser His Pro His Phe Leu Asn Ala Asp Pro
            340                 345                 350

GTT CTG GCA GAA GCG GTG ACT GGC CTG CAC CCT AAC CAG GAG GCA CAC     1222
Val Leu Ala Glu Ala Val Thr Gly Leu His Pro Asn Gln Glu Ala His
            355                 360                 365

TCC TTG TTC CTG GAC ATC CAC CCG GTC ACG GGA ATC CCC ATG AAC TGC     1270
Ser Leu Phe Leu Asp Ile His Pro Val Thr Gly Ile Pro Met Asn Cys
            370                 375                 380

TCT GTG AAA CTG CAG CTG AGC CTC TAC ATG AAA TCT GTC GCA GGC ATT     1318
Ser Val Lys Leu Gln Leu Ser Leu Tyr Met Lys Ser Val Ala Gly Ile
385                 390                 395                 400

GGA CAA ACT GGG AAG ATT GAG CCT GTG GTC CTG CCG CTG CTC TGG TTT     1366
Gly Gln Thr Gly Lys Ile Glu Pro Val Val Leu Pro Leu Leu Trp Phe
            405                 410                 415

GCA GAG AGC GGG GCC ATG GAG GGG GAG ACT CTT CAC ACA TTC TAC ACT     1414
Ala Glu Ser Gly Ala Met Glu Gly Glu Thr Leu His Thr Phe Tyr Thr
            420                 425                 430

CAG CTG GTG TTG ATG CCC AAG GTG ATG CAC TAT GCC CAG TAC GTC CTC     1462
Gln Leu Val Leu Met Pro Lys Val Met His Tyr Ala Gln Tyr Val Leu
            435                 440                 445

CTG GCG CTG GGC TGC GTC CTG CTG CTG GTC CCT GTC ATC TGC CAA ATC     1510
Leu Ala Leu Gly Cys Val Leu Leu Leu Val Pro Val Ile Cys Gln Ile
450                 455                 460

CGG AGC CAA GAG AAA TGC TAT TTA TTT TGG AGT AGT AGT AAA AAG GGC     1558
Arg Ser Gln Glu Lys Cys Tyr Leu Phe Trp Ser Ser Ser Lys Lys Gly
465                 470                 475                 480

TCA AAG GAT AAG GAG GCC ATT CAG GCC TAT TCT GAA TCC CTG ATG ACA     1606
Ser Lys Asp Lys Glu Ala Ile Gln Ala Tyr Ser Glu Ser Leu Met Thr
            485                 490                 495

TCA GCT CCC AAG GGC TCT GTG CTG CAG GAA GCA AAA CTG TAGGGTCCTG     1655
Ser Ala Pro Lys Gly Ser Val Leu Gln Glu Ala Lys Leu
            500                 505

AGGACACCGT GAGCCAGCCA GGCCTGGCCG CTGGGCCTGA CCGGCCCCCC AGCCCCTACA  1715
CCCCGCTTCT CCCGGACTCT CCCAGCAGAC AGCCCCCCAG CCCCACAGCC TGAGCCTCCC  1775
AGCTGCCATG TGCCTGTTGC ACACCTGCAC ACACGCCCTG GCACACATAC ACACATGCGT  1835
GCAGGCTTGT GCAGACACTC AGGGATGGAG CTGCTGCTGA AGGGACTTGT AGGGAGAGGC  1895
TCGTCAACAA GCACTGTTCT GGAACCTTCT CTCCACGTGG CCCACAGGCC TGACCACAGG  1955
GGCTGTGGGT CCTGCGTCCC CTTCCTCGGG TGAGCCTGGC CTGTCCCGTT CAGCCGTTGG  2015
GCCCAGGCTT CCTCCCCTCC AAGGTGAAAC ACTGCAGTCC CGGTGTGGTG GCTCCCCATG  2075
CAGGACGGGC CAGGCTGGGA GTGCCGCCTT CCTGTGCCAA ATTCAGTGGG GACTCAGTGC  2135
CCAGGCCCTG GCCACGAGCT TTGGCCTTGG TCTACCTGCC AGGCCAGGCA AAGCGCCTTT  2195
ACACAGGCCT CGGAAAACAA TGGAGTGAGC ACAAGATGCC CTGTGCAGCT GCCCGAGGGT  2255
CTCCGCCCAC CCCGGCCGGA CTTTGATCCC CCCGAAGTCT TCACAGGCAC TGCATCGGGT  2315
TGTCTGGCGC CCTTTTCCTC CAGCCTAAAC TGACATCATC CTATGGACTG AGCCGGCCAC  2375
TYTYTGGCCG AAGTGGCCGC AGGCTGTGCC CCCGAGCTGC CCCCACCCCC TCACAGGGTC  2435
CCTCAGATTA TAGGTGCCCA GGCTGAGGTG AAGAGGCCTG GGGGCCCTGC CTTCCGGGCG  2495
CTCCTGGACC CTGGGGCAAA CCTGTGACCC TTTTCTACTG GAATAGAAAT GAGTTTTATC  2555
ATCTTTGAAA AATAATTCAC TCTTGAAGTA ATAAACGTTT AAAAAAATGG GAAAAAAAA   2615
AAAAAAAAAA AAAA                                                    2630
```

(2) INFORMATION FOR SEQ ID NO:2:

(i) SEQUENCE CHARACTERISTICS:
        (A) LENGTH: 509 amino acids
        (B) TYPE: amino acid
        (D) TOPOLOGY: linear (ii) MOLECULE TYPE: protein (xi) SEQUENCE DESCRIPTION: SEQ ID NO:2:

```
Met Gly Cys Ser Ala Lys Ala Arg Trp Ala Ala Gly Ala Leu Gly Val
 1               5                  10                  15

Ala Gly Leu Leu Cys Ala Val Leu Gly Ala Val Met Ile Val Met Val
             20                  25                  30

Pro Ser Leu Ile Lys Gln Gln Val Leu Lys Asn Val Arg Ile Asp Pro
         35                  40                  45

Ser Ser Leu Ser Phe Asn Met Trp Lys Glu Ile Pro Ile Pro Phe Tyr
     50                  55                  60

Leu Ser Val Tyr Phe Phe Asp Val Met Asn Pro Ser Glu Ile Leu Lys
 65                  70                  75                  80

Gly Glu Lys Pro Gln Val Arg Glu Arg Gly Pro Tyr Val Tyr Arg Glu
                 85                  90                  95

Phe Arg His Lys Ser Asn Ile Thr Phe Asn Asn Asn Asp Thr Val Ser
            100                 105                 110

Phe Leu Glu Tyr Arg Thr Phe Gln Phe Gln Pro Ser Lys Ser His Gly
        115                 120                 125

Ser Glu Ser Asp Tyr Ile Val Met Pro Asn Ile Leu Val Leu Gly Ala
    130                 135                 140

Ala Val Met Met Glu Asn Lys Pro Met Thr Leu Lys Leu Ile Met Thr
145                 150                 155                 160

Leu Ala Phe Thr Thr Leu Gly Glu Arg Ala Phe Met Asn Arg Thr Val
                165                 170                 175

Gly Glu Ile Met Trp Gly Tyr Lys Asp Pro Leu Val Asn Leu Ile Asn
            180                 185                 190

Lys Tyr Phe Pro Gly Met Phe Pro Phe Lys Asp Lys Phe Gly Leu Phe
        195                 200                 205

Ala Glu Leu Asn Asn Ser Asp Ser Gly Leu Phe Thr Val Phe Thr Gly
    210                 215                 220

Val Gln Asn Ile Ser Arg Ile His Leu Val Asp Lys Trp Asn Gly Leu
225                 230                 235                 240

Ser Lys Val Asp Phe Trp His Ser Asp Gln Cys Asn Met Ile Asn Gly
                245                 250                 255

Thr Ser Gly Gln Met Trp Pro Pro Phe Met Thr Pro Glu Ser Ser Leu
            260                 265                 270

Glu Phe Tyr Ser Pro Glu Ala Cys Arg Ser Met Lys Leu Met Tyr Lys
        275                 280                 285

Glu Ser Gly Val Phe Glu Gly Ile Pro Thr Tyr Arg Phe Val Ala Pro
    290                 295                 300

Lys Thr Leu Phe Ala Asn Gly Ser Ile Tyr Pro Pro Asn Glu Gly Phe
305                 310                 315                 320

Cys Pro Cys Leu Glu Ser Gly Ile Gln Asn Val Ser Thr Cys Arg Phe
                325                 330                 335

Ser Ala Pro Leu Phe Leu Ser His Pro His Phe Leu Asn Ala Asp Pro
            340                 345                 350

Val Leu Ala Glu Ala Val Thr Gly Leu His Pro Asn Gln Glu Ala His
        355                 360                 365
```

```
Ser Leu Phe Leu Asp Ile His Pro Val Thr Gly Ile Pro Met Asn Cys
    370                 375                 380

Ser Val Lys Leu Gln Leu Ser Leu Tyr Met Lys Ser Val Ala Gly Ile
385                 390                 395                 400

Gly Gln Thr Gly Lys Ile Glu Pro Val Leu Pro Leu Leu Trp Phe
                405                 410                 415

Ala Glu Ser Gly Ala Met Glu Gly Thr Leu His Thr Phe Tyr Thr
                420                 425                 430

Gln Leu Val Leu Met Pro Lys Val Met His Tyr Ala Gln Tyr Val Leu
                435                 440                 445

Leu Ala Leu Gly Cys Val Leu Leu Val Pro Val Ile Cys Gln Ile
    450                 455                 460

Arg Ser Gln Glu Lys Cys Tyr Leu Phe Trp Ser Ser Lys Lys Gly
465                 470                 475                 480

Ser Lys Asp Lys Glu Ala Ile Gln Ala Tyr Ser Glu Ser Leu Met Thr
                485                 490                 495

Ser Ala Pro Lys Gly Ser Val Leu Gln Glu Ala Lys Leu
                500                 505
```

(2) INFORMATION FOR SEQ ID NO:3:

(i) SEQUENCE CHARACTERISTICS:
        (A) LENGTH: 1825 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 156..1682

(xi) SEQUENCE DESCRIPTION: SEQ ID NO:3:

```
GCCACCTGCA GGGCTACTGC TGCTCCGGCC ACTGCCTGAG ACTCACCTTG CTGGAACGTG    60

AGCCTCGGCT TCTGTCATCT CTGTGGCCTC TGTCGCTTCT GTCGCTGTCC CCCTTCAGTC   120

CCTGAGCCCC GCGAGCCCGG GCCGCACACG CGGAC ATG GGC GGC AGC GCC AGG      173
                                        Met Gly Gly Ser Ala Arg
                                         1               5

GCG CGC TGG GTG GCG GTG GGG CTG GGC GTC GTG GGG CTG CTG TGC GCT    221
Ala Arg Trp Val Ala Val Gly Leu Gly Val Val Gly Leu Leu Cys Ala
            10                  15                  20

GTG CTC GGT GTG GTT ATG ATC CTC GTG ATG CCC TCG CTC ATC AAA CAG    269
Val Leu Gly Val Val Met Ile Leu Val Met Pro Ser Leu Ile Lys Gln
        25                  30                  35

CAG GTA CTG AAG AAT GTC CGC ATA GAC CCC AGC AGC CTG TCC TTT GCA    317
Gln Val Leu Lys Asn Val Arg Ile Asp Pro Ser Ser Leu Ser Phe Ala
    40                  45                  50

ATG TGG AAG GAG ATC CCT GTA CCC TTC TAC TTG TCC GTC TAC TTC TTC    365
Met Trp Lys Glu Ile Pro Val Pro Phe Tyr Leu Ser Val Tyr Phe Phe
55                  60                  65                  70

GAG GTG GTC AAT CCC AGC GAG ATC CTA AAG GGT GAG AAG CCA GTA GTG    413
Glu Val Val Asn Pro Ser Glu Ile Leu Lys Gly Glu Lys Pro Val Val
                75                  80                  85

CGG GAG CGT GGA CCC TAT GTC TAC AGG GAA TTC AGA CAT AAG GCC AAC    461
Arg Glu Arg Gly Pro Tyr Val Tyr Arg Glu Phe Arg His Lys Ala Asn
                90                  95                 100

ATC ACC TTC AAT GAC AAT GAT ACT GTG TCC TTT GTG GAG CAC CGC AGC    509
Ile Thr Phe Asn Asp Asn Asp Thr Val Ser Phe Val Glu His Arg Ser
            105                 110                 115
```

-continued

```
CTC CAT TTC CAG CCG GAC AGG TCC CAC GGC TCT GAG AGT GAC TAC ATT           557
Leu His Phe Gln Pro Asp Arg Ser His Gly Ser Glu Ser Asp Tyr Ile
    120                 125                 130

ATA CTG CCT AAC ATT CTG GTC TTG GGG GGC GCA GTA ATG ATG GAG AGC           605
Ile Leu Pro Asn Ile Leu Val Leu Gly Gly Ala Val Met Met Glu Ser
135                 140                 145                 150

AAG TCT GCA GGC CTG AAG CTG ATG ATG ACC TTG GGG CTG GCC ACC TTG           653
Lys Ser Ala Gly Leu Lys Leu Met Met Thr Leu Gly Leu Ala Thr Leu
                155                 160                 165

GGC CAG CGT GCC TTT ATG AAC CGA ACA GTT GGT GAG ATC CTG TGG GGC           701
Gly Gln Arg Ala Phe Met Asn Arg Thr Val Gly Glu Ile Leu Trp Gly
        170                 175                 180

TAT GAG GAT CCC TTC GTG AAT TTT ATC AAC AAA TAC TTA CCA GAC ATG           749
Tyr Glu Asp Pro Phe Val Asn Phe Ile Asn Lys Tyr Leu Pro Asp Met
            185                 190                 195

TTC CCC ATC AAG GGC AAG TTC GGC CTG TTT GTT GAG ATG AAC AAC TCA           797
Phe Pro Ile Lys Gly Lys Phe Gly Leu Phe Val Glu Met Asn Asn Ser
    200                 205                 210

GAC TCT GGG CTC TTC ACT GTG TTC ACG GGC GTC CAG AAC TTC AGC AAG           845
Asp Ser Gly Leu Phe Thr Val Phe Thr Gly Val Gln Asn Phe Ser Lys
215                 220                 225                 230

ATC CAC CTG GTG GAC AGA TGG AAT GGG CTC AGC AAG GTC AAC TAC TGG           893
Ile His Leu Val Asp Arg Trp Asn Gly Leu Ser Lys Val Asn Tyr Trp
                235                 240                 245

CAT TCA GAG CAG TGC AAC ATG ATC AAT GGC ACT TCC GGG CAG ATG TGG           941
His Ser Glu Gln Cys Asn Met Ile Asn Gly Thr Ser Gly Gln Met Trp
        250                 255                 260

GCA CCA TTC ATG ACA CCC CAG TCC TCG CTG GAA TTC TTC AGT CCG GAA           989
Ala Pro Phe Met Thr Pro Gln Ser Ser Leu Glu Phe Phe Ser Pro Glu
            265                 270                 275

GCC TGC AGG TCT ATG AAG CTC ACC TAC CAT GAT TCA GGG GTG TTT GAA          1037
Ala Cys Arg Ser Met Lys Leu Thr Tyr His Asp Ser Gly Val Phe Glu
    280                 285                 290

GGC ATC CCC ACC TAT CGC TTC ACA GCC CCT AAA ACT TTG TTT GCC AAT          1085
Gly Ile Pro Thr Tyr Arg Phe Thr Ala Pro Lys Thr Leu Phe Ala Asn
295                 300                 305                 310

GGG TCT GTT TAC CCA CCC AAT GAA GGT TTC TGC CCG TGC CTT GAA TCC          1133
Gly Ser Val Tyr Pro Pro Asn Glu Gly Phe Cys Pro Cys Leu Glu Ser
                315                 320                 325

GGC ATT CAA AAT GTC AGC ACT TGC AGG TTT GGT GCA CCC CTG TTT CTG          1181
Gly Ile Gln Asn Val Ser Thr Cys Arg Phe Gly Ala Pro Leu Phe Leu
        330                 335                 340

TCA CAC CCT CAC TTC TAC AAT GCA GAC CCT GTG CTA TCA GAA GCC GTT          1229
Ser His Pro His Phe Tyr Asn Ala Asp Pro Val Leu Ser Glu Ala Val
            345                 350                 355

CTG GGT CTG AAC CCT GAC CCA AGG GAG CAT TCT TTG TTC CTT GAC ATC          1277
Leu Gly Leu Asn Pro Asp Pro Arg Glu His Ser Leu Phe Leu Asp Ile
    360                 365                 370

CAT CCG GTC ACT GGG ATC CCC ATG AAC TGT TCT GTG AAG TTG CAG ATA          1325
His Pro Val Thr Gly Ile Pro Met Asn Cys Ser Val Lys Leu Gln Ile
375                 380                 385                 390

AGC CTC TAC ATC AAA GCT GTC AAG GGC ATT GGG CAA ACA GGG AAG ATC          1373
Ser Leu Tyr Ile Lys Ala Val Lys Gly Ile Gly Gln Thr Gly Lys Ile
                395                 400                 405

GAG CCC GTG GTC CTC CCA TTG CTG TGG TTT GAG CAG AGC GGT GCC ATG          1421
Glu Pro Val Val Leu Pro Leu Leu Trp Phe Glu Gln Ser Gly Ala Met
        410                 415                 420

GGC GGC GAG CCC CTG AAC ACG TTC TAC ACG CAG CTG GTG CTG ATG CCC          1469
Gly Gly Glu Pro Leu Asn Thr Phe Tyr Thr Gln Leu Val Leu Met Pro
            425                 430                 435
```

-continued

```
CAG GTA CTT CAG TAT GTG CAG TAT GTG CTG CTG GGG CTG GGC GGC CTC      1517
Gln Val Leu Gln Tyr Val Gln Tyr Val Leu Leu Gly Leu Gly Gly Leu
        440                 445                 450

CTG CTG CTG GTC CCC GTC ATC TAC CAG TTG CGC AGC CAG GAG AAA TGC      1565
Leu Leu Leu Val Pro Val Ile Tyr Gln Leu Arg Ser Gln Glu Lys Cys
455                 460                 465                 470

TTT TTA TTT TGG AGT GGT AGT AAA AAG GGC TCG CAG GAT AAG GAG GCC      1613
Phe Leu Phe Trp Ser Gly Ser Lys Lys Gly Ser Gln Asp Lys Glu Ala
                475                 480                 485

ATT CAG GCC TAC TCT GAG TCT CTG ATG TCA CCA GCT GCC AAG GGC ACG      1661
Ile Gln Ala Tyr Ser Glu Ser Leu Met Ser Pro Ala Ala Lys Gly Thr
        490                 495                 500

GTG CTG CAA GAA GCC AAG CTG TAGGGTCCCA AAGACACCAC GAGCCCCCCC         1712
Val Leu Gln Glu Ala Lys Leu
        505

AACCTGATAG CTTGGTCAGA CCAGCCATCC AGCCCCTACA CCCCGCTTCT TGAGGACTCT    1772

CTCAGCGGAC AGTCCGCCAG TGCCATGGCC TGAGCCCCAG ATGTCACACC TGT           1825

(2) INFORMATION FOR SEQ ID NO:4:

(i) SEQUENCE CHARACTERISTICS:
        (A) LENGTH: 509 amino acids
        (B) TYPE: amino acid
        (D) TOPOLOGY: linear (ii) MOLECULE TYPE: protein (xi) SEQUENCE DESCRIPTION: SEQ ID NO:4:

Met Gly Gly Ser Ala Arg Ala Arg Trp Val Ala Val Gly Leu Gly Val
 1               5                  10                  15

Val Gly Leu Leu Cys Ala Val Leu Gly Val Val Met Ile Leu Val Met
                20                  25                  30

Pro Ser Leu Ile Lys Gln Gln Val Leu Lys Asn Val Arg Ile Asp Pro
            35                  40                  45

Ser Ser Leu Ser Phe Ala Met Trp Lys Glu Ile Pro Val Pro Phe Tyr
        50                  55                  60

Leu Ser Val Tyr Phe Phe Glu Val Val Asn Pro Ser Glu Ile Leu Lys
65                  70                  75                  80

Gly Glu Lys Pro Val Val Arg Glu Arg Gly Pro Tyr Val Tyr Arg Glu
                85                  90                  95

Phe Arg His Lys Ala Asn Ile Thr Phe Asn Asp Asn Asp Thr Val Ser
                100                 105                 110

Phe Val Glu His Arg Ser Leu His Phe Gln Pro Asp Arg Ser His Gly
            115                 120                 125

Ser Glu Ser Asp Tyr Ile Ile Leu Pro Asn Ile Leu Val Leu Gly Gly
        130                 135                 140

Ala Val Met Met Glu Ser Lys Ser Ala Gly Leu Lys Leu Met Met Thr
145                 150                 155                 160

Leu Gly Leu Ala Thr Leu Gly Gln Arg Ala Phe Met Asn Arg Thr Val
                165                 170                 175

Gly Glu Ile Leu Trp Gly Tyr Glu Asp Pro Phe Val Asn Phe Ile Asn
            180                 185                 190

Lys Tyr Leu Pro Asp Met Phe Pro Ile Lys Gly Lys Phe Gly Leu Phe
        195                 200                 205

Val Glu Met Asn Asn Ser Asp Ser Gly Leu Phe Thr Val Phe Thr Gly
    210                 215                 220

Val Gln Asn Phe Ser Lys Ile His Leu Val Asp Arg Trp Asn Gly Leu
```

```
              225                 230                 235                 240
Ser Lys Val Asn Tyr Trp His Ser Glu Gln Cys Asn Met Ile Asn Gly
                    245                 250                 255

Thr Ser Gly Gln Met Trp Ala Pro Phe Met Thr Pro Gln Ser Ser Leu
            260                 265                 270

Glu Phe Phe Ser Pro Glu Ala Cys Arg Ser Met Lys Leu Thr Tyr His
            275                 280                 285

Asp Ser Gly Val Phe Glu Gly Ile Pro Thr Tyr Arg Phe Thr Ala Pro
            290                 295                 300

Lys Thr Leu Phe Ala Asn Gly Ser Val Tyr Pro Asn Glu Gly Phe
305                 310                 315                 320

Cys Pro Cys Leu Glu Ser Gly Ile Gln Asn Val Ser Thr Cys Arg Phe
                325                 330                 335

Gly Ala Pro Leu Phe Leu Ser His Pro His Phe Tyr Asn Ala Asp Pro
                340                 345                 350

Val Leu Ser Glu Ala Val Leu Gly Leu Asn Pro Asp Pro Arg Glu His
                355                 360                 365

Ser Leu Phe Leu Asp Ile His Pro Val Thr Gly Ile Pro Met Asn Cys
                370                 375                 380

Ser Val Lys Leu Gln Ile Ser Leu Tyr Ile Lys Ala Val Lys Gly Ile
385                 390                 395                 400

Gly Gln Thr Gly Lys Ile Glu Pro Val Val Leu Pro Leu Leu Trp Phe
                405                 410                 415

Glu Gln Ser Gly Ala Met Gly Gly Glu Pro Leu Asn Thr Phe Tyr Thr
                420                 425                 430

Gln Leu Val Leu Met Pro Gln Val Leu Gln Tyr Val Gln Tyr Val Leu
                435                 440                 445

Leu Gly Leu Gly Gly Leu Leu Leu Val Pro Val Ile Tyr Gln Leu
450                 455                 460

Arg Ser Gln Glu Lys Cys Phe Leu Phe Trp Ser Gly Ser Lys Gly
465                 470                 475                 480

Ser Gln Asp Lys Glu Ala Ile Gln Ala Tyr Ser Glu Ser Leu Met Ser
                485                 490                 495

Pro Ala Ala Lys Gly Thr Val Leu Gln Glu Ala Lys Leu
                500                 505
```

(2) INFORMATION FOR SEQ ID NO:5:

(i) SEQUENCE CHARACTERISTICS:
        (A) LENGTH: 1002 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
ACTGCGGAGA TGAGGGTCTA GAAGGTGGTG GCGGGGCATG TGGACCGTTG TAAGGGCTCT      60

GGGGTTCCTG GGTGGGCTGG CGAAGTCCTA CTCACAGTGA CCAACCATGA TGATGGTCCC     120

GATAGAGGAG GAGAGGGAGG AGGAGGGAAA AGGAAGGGTG AGGGGCTCAG AGGGGAGAGC     180

TGGGAGGAGG GGAGACATAG GTGGGGGAAG GGTAGGAGA AAGGGGAAGG GAGCAAGAGG     240

GTGAGGGGCA CCAGGCCCCA TAGACGTTTT GGCTCAGCGG CCACGAGGCT TCATCAGCTC     300

CCGCCCCAAA ACGGAAGCGA GGCCGTGGGG GCAGCGGCAG CATGGCGGGG CTTGTCTTGG     360

CGGCCATGGC CCCGCCCCCT GCCCGTCCGA TCAGCGCCCC GCCCCGTCCC CGCCCCGACC     420
```

```
CCGCCCCGGG CCCGCTCAGG CCCCGCCCCT GCCGCCGGAA TCCTGAAGCC CAAGGCTGCC      480

CGGGGGCGGT CCGGCGGCGC CGGCGATGGG GCATAAAACC ACTGGCCACC TGCCGGGCTG      540

CTCCTGCGTG CGCTGCCGTC CCGGATCCAC CGTGCCTCTG CGGCCTGCGT GCCCCGAGTC      600

CCCGCCTGTG TCGTCTCTGT CGCCGTCCCC GTCTCCTGCC AGGCGCGGAG CCCTGCGAGC      660

CGCGGGTGGG CCCCAGGCGC GCAGACATGG GCTGCTCCGC CAAAGCGCGC TGGGCTGCCG      720

GGGCGCTGGG CGTCGCGGGG CTACTGTGCG CTGTGCTGGG CGCTGTCATG ATCGTGATGG      780

TGCCGTCGCT CATCAAGCAG CAGGTCCTTA AGGTGGGTGA GGGAGACCCC AGGGGGTCCG      840

CGCACGGACC CGGGCTGTTG GGCGCTGGGC GCCGGGAGGA CCCGCGCGTT GCGGTGGGTG      900

GGCGACCGCA GCGGAATCGG CGCCCGGGCC TGGCGCCGCA GAACACGAGG GAGGCCAGGC      960

GCTTCGGGAG GGGCTGCTGC CCGCCTCCCC ACCACCCTCA CC                       1002

(2) INFORMATION FOR SEQ ID NO:6:

(i) SEQUENCE CHARACTERISTICS:
         (A) LENGTH: 479 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:6:

AGCCTCATGT GCGAAGGGCT TTCCCACCAC CTCCTATCCC AAGCTCCCGC CGAGGAGCCC       60

CTTCCCTGGC CGGGCTCGGG CAGCTGTTCC GGAGCCTTGT GGTGGGGCGT GGGGCCCTCA      120

TCACTCTCCT CACAAGCGTA CTTGTCCCTT CCCCTGCAGA ACGTGCGCAT CGACCCCAGT      180

AGCCTGTCCT TCAACATGTG GAAGGAGATC CCTATCCCCT TCTATCTCTC CGTCTACTTC      240

TTTGACGTCA TGAACCCCAG CGAGATCCTG AAGGGCGAGA AGCCGCAGGT GCGGGAGCGC      300

GGGCCCTACG TGTACAGGTG AGGCTGTGTC CACGTGATGG TGGACGGGCC GGCTGACGCT      360

GGGCATGGGA CGGGTCTCAA GTGGACGGGA TGGGGAGGCT GCTGACTGAC CCCCAAACAT      420

TGTTCCGGAA GCACGCAACT CATAGTCGGG GTAAGTGCTA CTCCCAAAAA AGTTTGCGT      479

(2) INFORMATION FOR SEQ ID NO:7:

(i) SEQUENCE CHARACTERISTICS:
         (A) LENGTH: 495 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:7:

CATGTCCTGC AGTGGGCAGG CAGCGGGAGG GACAGACTTG GCGAAGGGGC CGAGCTCAGC       60

TTTGGCTGTG GGGCCGGAGG TGTGCACAGA CGTCCAGGGC CCCTGGTTCC CAGGCAGGCA      120

TTGCAGGCGA GTAGAAGGGA AACGTCCCAT GCAGCGGGGC GGGGCGTCTG ACCCACTGGC      180

TTCCCCCACA GGGAGTTCAG GCACAAAAGC AACATCACCT TCAACAACAA CGACACCGTG      240

TCCTTCCTCG AGTACCGCAC CTTCCAGTTC CAGCCCTCCA AGTCCACGG CTCGGAGAGC      300

GACTACATCG TCATGCCCAA CATCCTGGTC TTGGTGAGGC TGCCCTGTGG CCCACGCCGC      360

CTCGCACCCT GACCTCGTCC CCTGTCTCTC CTCCCGCCTG CCCCTTGTGC AGAGAGCAGT      420

CCCTGAGGTG GTCGGAGCGT GGGGACTCAC GCCTGGTGGG TGGCTTTCGG CCCTGTGCTG      480

TCTCCACCAC CCCCA                                                      495
```

(2) INFORMATION FOR SEQ ID NO:8:

(i) SEQUENCE CHARACTERISTICS:
        (A) LENGTH: 526 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
GGTGGTTCTG GTGTCCCAGA TGCCCCACGT GGCCACTCCA GGGGCCTCCT GCACCCCAGC    60
ATTTCCCTTC ATGGGCTCTT TGCTGTGAGG CCCAGCTGGG GCCAAGGGAG GATGGGCCAG   120
CCACGTCCAG CCTCTGACAC TAGTGTCCCT TCGCCTTGCA GGGTGCGGCG GTGATGATGG   180
AGAATAAGCC CATGACCCTG AAGCTCATCA TGACCTTGGC ATTCACCACC CTCGGCGAAC   240
GTGCCTTCAT GAACCGCACT GTGGGTGAGA TCATGTGGGG CTACAAGGAC CCCTTGTGAA   300
TCTCATCAAC AAGTACTTTC CAGGCATGTT CCCCTTCAAG GACAAGTTCG GATTATTTGC   360
TGAGGTACGT GTGGCCTGGT GAGAAGCCAA AGATTCAGGC CTGTGTCCTG TCTTCCCCTC   420
ACACAGCCTG GACACTGGTC ACCAGCTTGC TTTGTAGCTG GCTGGGATC TAGTGGCTGT    480
GGGTTGTAAG TGACTGAGAA CCTGACTCAA ACCGGCTTGA GTGAAA                  526
```

(2) INFORMATION FOR SEQ ID NO:9:

(i) SEQUENCE CHARACTERISTICS:
        (A) LENGTH: 416 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
CCTCTCGGTC CCCAGACACT GGGCATTTGG CAGTGAACCA GATGCTGGGG GCCCTGTCCT    60
TCTGGTGGAG GGGGAGGAGG GCTCAGCCCA GAATGTTCAG ACCAGGCCGG CTCAATGGCA   120
GGCCTAAGCC TTACGATGCT GTTCCCTGCT GTGTCTGTAG CTCAACAACT CCGACTCTGG   180
GCTCTTCACG GTGTTCACGG GGGTCCAGAA CATCAGCAGG ATCCACCTCG TGGACAAGTG   240
GAACGGGCTG AGCAAGGTGA GGGGCGAGAG GCGAGGGCCC CTGTCGCCAG GGAGAGGGGA   300
GGGTGGGCCC GGCCATGGCT GCTCGGGAGT GGCAGGGACC AGAGAGCTCC TTCTTCCTTT   360
GTCGTGAAGA GGGTGCTGGG AGGATGAACA CTCTTGAAGT TGGAGGAGGG ATTTTA       416
```

(2) INFORMATION FOR SEQ ID NO:10:

(i) SEQUENCE CHARACTERISTICS:
        (A) LENGTH: 436 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
TCTCTGTGTG TCTACATAGC CTGCCCTCTT CCCACCGTGC CAGTATTGGG AATTGAGTGG    60
CCGTGCGTGC ACCAGGGTGA GTTAGGTGTG CAGCACCTGA GAGGGCTTAT TAAGGGGCCT   120
TGGCCCTACT GAGGGGTCTA GTCTGGATGC TTCCCCCCAG GTTGACTTCT GGCATTCCGA   180
TCAGTGCAAC ATGATCAATG GAACTTCTGG GCAAATGTGG CCGCCCTTCA TGACTCCTGA   240
GTCCTCGCTG GAGTTCTACA GCCCGGAGGC CTGCCGGTAA TCACTGGGAC TCGGGGCCTC   300
```

| | | |
|---|---|---|
| CTGGGTTTCC TGGGTAGCTC ATGGCCAAAT TCTGTGGTGT TGGCTGTGCA CTTGGAAAGC | 360 |
| ATTTTGACTC ATCGTGGATT TGACTCAGTA GCCCTTGGCA CCAGCTTGAA TTCTCTTTGG | 420 |
| TCACACCACC AAAAGC | 436 |

(2) INFORMATION FOR SEQ ID NO:11:

(i) SEQUENCE CHARACTERISTICS:
        (A) LENGTH: 481 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

| | |
|---|---|
| GGAGGTCGCT GCAGCTCCGC GGGTGAGAGA TGGGGGCGGT TTGGACCCGG GAGGTGGTAG | 60 |
| CGCCCGTGGG GAGAAGTGGC TGGATCTGGG CAGCCTTTGG CAGGGCCTGG CTCTGGCCGC | 120 |
| CGGGTCTGGG TGTCCCCTCT CATCCTGTCT GTCCCCTGCA GATCCATGAA GCTAATGTAC | 180 |
| AAGGAGTCAG GGGTGTTTGA AGGCATCCCC ACCTATCGCT TCGTGGCTCC CAAAACCCTG | 240 |
| TTTGCCAACG GGTCCATCTA CCCACCCAAC GAAGGCTTCT GCCCGTGCCT GGAGTCTGGA | 300 |
| ATTCAGAACG TCAGCAGCTG CAGGTTCAGT ACGTGCCGTC CCCTGTTCTG GGATNGCCGG | 360 |
| AGGGTGTTAG GTNTNGGGCA CCTNANGGTT TATCTGCCCA ATGCTGTCTG CTTAATCTCT | 420 |
| GGCCTCTGTA CTCTTGATAA CCCATTAAGC CAAAAATATG ATGCCTCTGG GACGATATCT | 480 |
| G | 481 |

(2) INFORMATION FOR SEQ ID NO:12:

(i) SEQUENCE CHARACTERISTICS:
        (A) LENGTH: 430 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

| | |
|---|---|
| TGGGGCTTTT TACAGAATGG AGGAAGGGAT CCTCTCTGTC GGGTATTATG GTCATCGCCA | 60 |
| CGGGGGTGCC GTGCAGACCA CAGCTCTGTG CAGACTTCCG GAGTGGCAGG ACGTGCCAAT | 120 |
| ATACTGTCGT TGTATGATGT CCCCTCCCTG CCCTTGTTGT AGGTGCCCCC TTGTTTCTCT | 180 |
| CCCATCCTCA CTTCATCAAC GCCGACCCGG TTCTGGCAGA AGCGGTGACT GGCCTGCACC | 240 |
| CTAACCAGGA GGCACACTCC TTGTTCGTGG ACATCCACCC GGTGAGCCCC TGCCATCCTC | 300 |
| TGTGGGGGGT GGGTGATTCC TGGTTGGAGC ACACCTGGCT GCCTCCTCTC TCCCCAGGCA | 360 |
| GAGAGCTGCT GTGGGCTGGG GTGGTGGGAA GCCTGGCTTC TAGAATCTCG AGCCACCAAA | 420 |
| GTTCCTTACT | 430 |

(2) INFORMATION FOR SEQ ID NO:13:

(i) SEQUENCE CHARACTERISTICS:
        (A) LENGTH: 390 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

```
CCCCAGCCTG TGGCTTGTTT TAGGTAAGAT ACAAGCAAGC TCCACTGGGC AGTTAGCTGG        60

GACGCCCACC CTCTTGACTG GGACCAGGGA AAAGAAGGTT GACTGTGTCC CTGGAGCTTG       120

GGGGTGGCCA GTCTCCTCAC TGTGTTTGTT GCCGCAGGTC ACGGGAATCC CCATGAACTG       180

CTCTGTGAAA CTGCAGCTGA GCCTCTACAT GAAATCTGTC GCAGGCATTG GGTGAGTGGG       240

GACTGGGAAC TGGGGCTGCA TTGCTCATTG AGAGATTANG TGCTCAGTGC TCCAGTGTTC       300

CCAGACTCCC CTGACATACC CCAGGAAACA GGGCATGGGG AAGGGAGAGG GTCCTATTGG       360

GGGTGGAATC CAGTCCCTGC TGATCTTCTC                                       390
```

(2) INFORMATION FOR SEQ ID NO:14:

(i) SEQUENCE CHARACTERISTICS:
        (A) LENGTH: 370 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

```
ATGGCTCCTA AAGTGTTTCA GCTCATTGTT TATATTTGGT GGTGAGGGTT TAGTGTGTGC        60

AAAATTATAC TAAACCTGTT TAGATGTTGT ATTCAAGCAG AATTAGATCA AGTTTGGGTG       120

TAAGACTTTG TTCCAACACC TATGTCTTGC TTATTTCCAG ACAAACTGGG AAGATTGAGC       180

CTGTGGTCCT GCCGCTGCTC TGGTTTGCAG AGGTAAGGGT GCGTTGGGCA CAGCGTCGGG       240

GGCTTTTGTT AATAGCCAAT GTGGGCATTT GAGGCAGGAG GCGGGGGAG CACCTTGTAG        300

AAAGGGAGAG GGCTGAGCCA GGGTAACCGG ACTGTTACAT GGACCAGCGT ATCATACACT       360

TCACCCTGTC                                                             370
```

(2) INFORMATION FOR SEQ ID NO:15:

(i) SEQUENCE CHARACTERISTICS:
        (A) LENGTH: 470 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

```
CCTGGAGGGA GGAGGTCCCT GGCAGGCTCC AACACATGCT TTAGCCGGGA AGCTTGAGGT        60

GGGGAAAAGC TGAGGCGGGC ACAGAGGAAG GTGTTGGGTG GCATCTGCGC TGTAGCCCGC       120

AGCCTGCGGC CCCAGCTCAT GTGTTTGTCA TTCTGTCTCC TCAGAGCGGG GCCATGGAGG       180

GGGAGACTCT TCACACATTC TACACTCAGC TGGTGTTGAT GCCCAAGGTG ATGCACTATG       240

CCCAGTACGT CCTCCTGGCG CTGGGCTGCG TCCTGCTGCT GGTCCCTGTC ATCTGCCAAA       300

TCCGGAGCCA AGTAGGTGCT GGCCAGAGGG CAGCCCGGGC TGACAGCCAT TCGCTTGCCT       360

GCTGGGGGAA AGGGGCCTCA GATCGGACCC TCTGGCCAAC CGCAGCCTGG AGCCCACCTC       420

CAGCAGCAGT CCTGCGTCTC TGCCGGAGTG GGAGCGGTCA CTGCTGGGGG                  470
```

(2) INFORMATION FOR SEQ ID NO:16:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

```
CCCCACATCT CAGCCACCTG CAATCGTTGA GGGTTGTTGG ACTCTAAACT TATGTGCCTT        60

TCCTGTTTCC TCTTTGCCTT TTGCAAATTG AAGAACCGTG TAAAACCATT TTTATGTGGC       120

TTCAACGTCA ACTATAAATT AGCTTGGTTA TCTTCTAGGA GAAATGCTAT TTATTTTGGA       180

GTAGTAGTAA AAAGGGCTCA AAGGATAAGG AGGCCATTCA GGCCTATTCT GAATCCCTGA       240

TGACATCAGC TCCCAAGGGC TCTGTGCTGC AGGAAGCAAA ACTGTAGGTG GGTACCAGGT       300

AATGCCGTGC GCCTCCCCGC CCCCTCCCAT ATCAAGTAGA ATGCTGGCGG CTTAAAACAT       360

TTGGGGTCCT GCTCATTCCT TCAGCCTCAA CTTCACCTGG AGTGTCTACA GACTGAAGAT       420

GCATATTTGT GTATTTTGCT TTTGGAGAAA                                        450
```

(2) INFORMATION FOR SEQ ID NO:17:

(i) SEQUENCE CHARACTERISTICS:
        (A) LENGTH: 544 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

```
ACTGCGGAGA TGAGGGTCTA GAAGGTGGTG GCGGGGCATG TGGACCGTTG TAAGGGCTCT        60

GGGGTTCCTG GGTGGGCTGG CGAAGTCCTA CTCACAGTGA CCAACCATGA TGATGGTCCC       120

GATAGAGGAG GAGAGGGAGG AGGAGGGAAA AGGAAGGGTG AGGGGCTCAG AGGGGAGAGC       180

TGGGAGGAGG GGAGACATAG GTGGGGGAAG GGGTAGGAGA AAGGGGAAGG GAGCAAGAGG       240

GTGAGGGGCA CCAGGCCCCA TAGACGTTTT GGCTCAGCGG CCACGAGGCT TCATCAGCTC       300

CCGCCCCAAA ACGGAAGCGA GGCCGTGGGG GCAGCGGCAG CATGGCGGGG CTTGTCTTGG       360

CGGCCATGGC CCCGCCCCCT GCCCGTCCGA TCAGCGCCCC GCCCCGTCCC CGCCCCGACC       420

CCGCCCCGGG CCCGCTCAGG CCCCGCCCCT GCCGCCGGAA TCCTGAAGCC CAAGGCTGCC       480

CGGGGGCGGT CCGGCGGCGC CGGCGATGGG GCATAAAACC ACTGGCCACC TGCCGGGCTG       540

CTCC                                                                   544
```

(2) INFORMATION FOR SEQ ID NO:18:

(i) SEQUENCE CHARACTERISTICS:
        (A) LENGTH: 190 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

```
GTGGGTGAGG GAGACCCCAG GGGGTCCGCG CACGGACCCG GGCTGTTGGG CGCTGGGCGC        60

CGGGAGGACC CGCGCGTTGC GGTGGGTGGG CGACCGCAGC GGAATCGGCG CCCGGGCCTG       120

GCGCCGCAGA ACACGAGGGA GGCCAGGCGC TTCGGGAGGG GCTGCTGCCC GCCTCCCCAC       180

CACCCTCACC                                                              190
```

(2) INFORMATION FOR SEQ ID NO:19:

(i) SEQUENCE CHARACTERISTICS:
        (A) LENGTH: 159 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:19:

```
AGCCTCATGT GCGAAGGGCT TTCCCACCAC CTCCTATCCC AAGCTCCCGC CGAGGAGCCC        60

CTTCCCTGGC CGGGCTCGGG CAGCTGTTCC GGAGCCTTGT GGTGGGGCGT GGGGCCCTCA       120

TCACTCTCCT CACAAGCGTA CTTGTCCCTT CCCCTGCAG                              159
```

(2) INFORMATION FOR SEQ ID NO:20:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

```
GTGAGGCTGT GTCCACGTGA TGGTGGACGG GCCGGCTGAC GCTGGGCATG GGACGGGTCT        60

CAAGTGGACG GGATGGGGAG GCTGCTGACT GACCCCCAAA CATTGTTCCG GAAGCACGCA       120

ACTCATAGTC GGGGTAAGTG CTACTCCCAA AAAAGTTTGC GT                          162
```

(2) INFORMATION FOR SEQ ID NO:21:

(i) SEQUENCE CHARACTERISTICS:
        (A) LENGTH: 191 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

```
CATGTCCTGC AGTGGGCAGG CAGCGGGAGG GACAGACTTG GCGAAGGGGC CGAGCTCAGC        60

TTTGGCTGTG GGGCCGGAGG TGTGCACAGA CGTCCAGGGC CCCTGGTTCC CAGGCAGGCA       120

TTGCAGGCGA GTAGAAGGGA AACGTCCCAT GCAGCGGGGC GGGGCGTCTG ACCCACTGGC       180

TTCCCCCACA G                                                            191
```

(2) INFORMATION FOR SEQ ID NO:22:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

```
GTGAGGCTGC CCTGTGGCCC ACGCCGCCTC GCACCCTGAC CTCGTCCCCT GTCTCTCCTC        60

CCGCCTGCCC CTTGTGCAGA GAGCAGTCCC TGAGGTGGTC GGAGCGTGGG GACTCACGCC       120

TGGTGGGTGG CTTTCGGCCC TGTGCTGTCT CCACCACCCC CA                          162
```

(2) INFORMATION FOR SEQ ID NO:23:

(i) SEQUENCE CHARACTERISTICS:
        (A) LENGTH: 161 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

```
GGTGGTTCTG GTGTCCCAGA TGCCCCACGT GGCCACTCCA GGGGCCTCCT GCACCCCAGC    60

ATTTCCCTTC ATGGGCTCTT TGCTGTGAGG CCCAGCTGGG GCCAAGGGAG GATGGGCCAG   120

CCACGTCCAG CCTCTGACAC TAGTGTCCCT TCGCCTTGCA G                      161
```

(2) INFORMATION FOR SEQ ID NO:24:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

```
GTACGTGTGG CCTGGTGAGA AGCCAAAGAT TCAGGCCTGT GTCCTGTCTT CCCCTCACAC    60

AGCCTGGACA CTGGTCACCA GCTTGCTTTG TAGCTGGCTG GGGATCTAGT GGCTGTGGGT   120

TGTAAGTGAC TGAGAACCTG ACTCAAACCG GCTTGAGTGA AA                     162
```

(2) INFORMATION FOR SEQ ID NO:25:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

```
CCTCTCGGTC CCCAGACACT GGGCATTTGG CAGTGAACCA GATGCTGGGG GCCCTGTCCT    60

TCTGGTGGAG GGGGAGGAGG GCTCAGCCCA GAATGTTCAG ACCAGGCCGG CTCAATGGCA   120

GGCCTAAGCC TTACGATGCT GTTCCCTGCT GTGTCTGTAG                        160
```

(2) INFORMATION FOR SEQ ID NO:26:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

```
GTGAGGGGCG AGAGGCGAGG GCCCCTGTCG CCAGGGAGAG GGGAGGGTGG GCCCGGCCAT    60

GGCTGCTCGG GAGTGGCAGG GACCAGAGAG CTCCTTCTTC CTTTGTCGTG AAGAGGGTGC   120

TGGGAGGATG AACACTCTTG AAGTTGGAGG AGGGATTTTA                        160
```

(2) INFORMATION FOR SEQ ID NO:27:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

```
TCTCTGTGTG TCTACATAGC CTGCCCTCTT CCCACCGTGC CAGTATTGGG AATTGAGTGG      60

CCGTGCGTGC ACCAGGGTGA GTTAGGTGTG CAGCACCTGA GAGGGCTTAT TAAGGGGCCT     120

TGGCCCTACT GAGGGGTCTA GTCTGGATGC TTCCCCCCAG                           160
```

(2) INFORMATION FOR SEQ ID NO:28:

(i) SEQUENCE CHARACTERISTICS:
  (A) LENGTH: 160 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:28:

```
GTAATCACTG GGACTCGGGG CCTCCTGGGT TTCCTGGGTA GCTCATGGCC AAATTCTGTG      60

GTGTTGGCTG TGCACTTGGA AAGCATTTTG ACTCATCGTG GATTTGACTC AGTAGCCCTT     120

GGCACCAGCT TGAATTCTCT TTGGTCACAC CACCAAAAGC                           160
```

(2) INFORMATION FOR SEQ ID NO:29:

(i) SEQUENCE CHARACTERISTICS:
  (A) LENGTH: 161 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:29:

```
GGAGGTCGCT GCAGCTCCGC GGGTGAGAGA TGGGGGCGGT TTGGACCCGG GAGGTGGTAG      60

CGCCCGTGGG GAGAAGTGGC TGGATCTGGG CAGCCTTTGG CAGGGCCTGG CTCTGGCCGC     120

CGGGTCTGGG TGTCCCCTCT CATCCTGTCT GTCCCCTGCA G                         161
```

(2) INFORMATION FOR SEQ ID NO:30:

(i) SEQUENCE CHARACTERISTICS:
  (A) LENGTH: 153 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:30:

```
GTACGTGCCG TCCCCTGTTC TGGGATNGCC GGAGGGTGTT AGGTNTNGGG CACCTNANGG      60

TTTATCTGCC CAATGCTGTC TGCTTAATCT CTGGCCTCTG TACTCTTGAT AACCCATTAA     120

GCCAAAAATA TGATGCCTCT GGGACGATAT CTG                                  153
```

(2) INFORMATION FOR SEQ ID NO:31:

(i) SEQUENCE CHARACTERISTICS:
  (A) LENGTH: 162 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:31:

```
TGGGGCTTTT TACAGAATGG AGGAAGGGAT CCTCTCTGTC GGGTATTATG GTCATCGCCA      60

CGGGGGTGCC GTGCAGACCA CAGCTCTGTG CAGACTTCCG GAGTGGCAGG ACGTGCCAAT     120
```

```
ATACTGTCGT TGTATGATGT CCCCTCCCTG CCCTTGTTGT AG                 162
```

(2) INFORMATION FOR SEQ ID NO:32:

(i) SEQUENCE CHARACTERISTICS:
        (A) LENGTH: 149 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

```
GTGAGCCCCT GCCATCCTCT GTGGGGGTG GGTGATTCCT GGTTGGAGCA CACCTGGCTG    60

CCTCCTCTCT CCCCAGGCAG AGAGCTGCTG TGGGCTGGGG TGGTGGGAAG CCTGGCTTCT  120

AGAATCTCGA GCCACCAAAG TTCCTTACT                                    149
```

(2) INFORMATION FOR SEQ ID NO:33:

(i) SEQUENCE CHARACTERISTICS:
        (A) LENGTH: 157 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

```
CCCCAGCCTG TGGCTTGTTT TAGGTAAGAT ACAAGCAAGC TCCACTGGGC AGTTAGCTGG    60

GACGCCCACC CTCTTGACTG GGACCAGGGA AAAGAAGGTT GACTGTGTCC CTGGAGCTTG  120

GGGGTGGCCA GTCTCCTCAC TGTGTTTGTT GCCGCAG                           157
```

(2) INFORMATION FOR SEQ ID NO:34:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

```
GTGAGTGGGG ACTGGGAACT GGGGCTGCAT TGCTCATTGA GAGATTANGT GCTCAGTGCT    60

CCAGTGTTCC CAGACTCCCC TGACATACCC CAGGAAACAG GGCATGGGGA AGGGAGAGGG  120

TCCTATTGGG GGTGGAATCC AGTCCCTGCT GATCTTCTC                         159
```

(2) INFORMATION FOR SEQ ID NO:35:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

```
ATGGCTCCTA AAGTGTTTCA GCTCATTGTT TATATTTGGT GGTGAGGGTT TAGTGTGTGC    60

AAAATTATAC TAAACCTGTT TAGATGTTGT ATTCAAGCAG AATTAGATCA AGTTTGGGTG  120

TAAGACTTTG TTCCAACACC TATGTCTTGC TTATTTCCAG                        160
```

(2) INFORMATION FOR SEQ ID NO:36:

(i) SEQUENCE CHARACTERISTICS:
    (A) LENGTH: 158 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:36:

```
GTAAGGGTGC GTTGGGCACA GCGTCGGGGG CTTTTGTTAA TAGCCAATGT GGGCATTTGA      60
GGCAGGAGGC GGGGGGAGCA CCTTGTAGAA AGGGAGAGGG CTGAGCCAGG GTAACCGGAC     120
TGTTACATGG ACCAGCGTAT CATACACTTC ACCCTGTC                             158
```

(2) INFORMATION FOR SEQ ID NO:37:

(i) SEQUENCE CHARACTERISTICS:
        (A) LENGTH: 164 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

```
CCTGGAGGGA GGAGGTCCCT GGCAGGCTCC AACACATGCT TTAGCCGGGA AGCTTGAGGT      60
GGGGAAAAGC TGAGGCGGGC ACAGAGGAAG GTGTTGGGTG GCATCTGCGC TGTAGCCCGC     120
AGCCTGCGGC CCCAGCTCAT GTGTTTGTCA TTCTGTCTCC TCAG                      164
```

(2) INFORMATION FOR SEQ ID NO:38:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

```
GTAGGTGCTG GCCAGAGGGC AGCCCGGGCT GACAGCCATT CGCTTGCCTG CTGGGGGAAA      60
GGGGCCTCAG ATCGGACCCT CTGGCCAACC GCAGCCTGGA GCCCACCTCC AGCAGCAGTC     120
CTGCGTCTCT GCCGGAGTGG GAGCGGTCAC TGCTGGGGG                            159
```

(2) INFORMATION FOR SEQ ID NO:39:

(i) SEQUENCE CHARACTERISTICS:
        (A) LENGTH: 158 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

```
CCCCACATCT CAGCCACCTG CAATCGTTGA GGGTTGTTGG ACTCTAAACT TATGTGCCTT      60
TCCTGTTTCC TCTTTGCCTT TTGCAAATTG AAGAACCGTG TAAAACCATT TTTATGTGGC     120
TTCAACGTCA ACTATAAATT AGCTTGGTTA TCTTCTAG                             158
```

(2) INFORMATION FOR SEQ ID NO:40:

(i) SEQUENCE CHARACTERISTICS:
        (A) LENGTH: 163 base pairs
        (B) TYPE: nucleic acid (C) STRANDEDNESS: single
    (D) TOPOLOGY: linear (ii) MOLECULE TYPE: DNA (genomic)

(xi) SEQUENCE DESCRIPTION: SEQ ID NO:40:

GTGGGTACCA GGTAATGCCG TGCGCCTCCC CGCCCCCTCC CATATCAAGT AGAATGCTGG    60

CGGCTTAAAA CATTTGGGGT CCTGCTCATT CCTTCAGCCT CAACTTCACC TGGAGTGTCT   120

ACAGACTGAA GATGCATATT TGTGTATTTT GCTTTTGGAG AAA                    163

(2) INFORMATION FOR SEQ ID NO:41:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:41:

CCCCTGCCGC CGGAATCCTG AAG                                           23

(2) INFORMATION FOR SEQ ID NO:42:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:42:

CGCTTTGGCG GAGCAGCCCA TGTC                                          24

(2) INFORMATION FOR SEQ ID NO:43:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:43:

TGGGGCCCTC ATCACTCTCC TCAC                                          24

(2) INFORMATION FOR SEQ ID NO:44:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:44:

GCAGCCTCCC CATCCCGTCC ACT                                           23

(2) INFORMATION FOR SEQ ID NO:45:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "primer"

(xi) SEQUENCE DESCRIPTION: SEQ ID NO:45:

ATTGCAGGCG AGTAGAAG                                                18

(2) INFORMATION FOR SEQ ID NO:46:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:46:

CAGGCGGGAG GAGAGACA                                                18

(2) INFORMATION FOR SEQ ID NO:47:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:47:

TGGGCTCTTT GCTGTGAGGC                                              20

(2) INFORMATION FOR SEQ ID NO:48:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:48:

CCAGGCTGTG TGAGGGGAAG                                              20

(2) INFORMATION FOR SEQ ID NO:49:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:49:

GCCCAGAATG TTCAGACCAG                                              20

(2) INFORMATION FOR SEQ ID NO:50:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "primer"

(xi) SEQUENCE DESCRIPTION: SEQ ID NO:50:

GCACCCTCTT CACGACAAAG                                                        20

(2) INFORMATION FOR SEQ ID NO:51:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:51:

CACCTGAGAG GGCTTATTA                                                         19

(2) INFORMATION FOR SEQ ID NO:52:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:52:

CAAAATGCTT TCCAAGTGC                                                         19

(2) INFORMATION FOR SEQ ID NO:53:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:53:

GCCGCCGGGT CTGGGTGTCC                                                        20

(2) INFORMATION FOR SEQ ID NO:54:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:54:

CAGAGGCCAG AGATTAAGCA GAC                                                    23

(2) INFORMATION FOR SEQ ID NO:55:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "primer"

(xi) SEQUENCE DESCRIPTION: SEQ ID NO:55:

TTGTATGATG TCCCCTCCCT                                         20

(2) INFORMATION FOR SEQ ID NO:56:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:56:

TTCCCACCAC CCCAGCCCAC                                         20

(2) INFORMATION FOR SEQ ID NO:57:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:57:

GGTTGACTGT GTCCCTGGAG                                         20

(2) INFORMATION FOR SEQ ID NO:58:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:58:

GGGAACACTG GAGCACTGAG C                                       21

(2) INFORMATION FOR SEQ ID NO:59:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:59:

GGTGGTGAGG GTTTAGTGTG                                         20

(2) INFORMATION FOR SEQ ID NO:60:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:60:

CTCCCCCCGC CTCCTGCCTC                                                    20

(2) INFORMATION FOR SEQ ID NO:61:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:61:

AAGGTGTTGG GTGGCATCTG                                                    20

(2) INFORMATION FOR SEQ ID NO:62:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:62:

GGCTCCAGGC TGCGGTTGGC                                                    20

(2) INFORMATION FOR SEQ ID NO:63:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:63:

TTGAAGAACC GTGTAAAAC                                                     19

(2) INFORMATION FOR SEQ ID NO:64:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:64:

TTGAGGCTGA AGGAATGA                                                      18

(2) INFORMATION FOR SEQ ID NO:65:

(i) SEQUENCE CHARACTERISTICS:
    (A) LENGTH: 430 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:65:

```
TGGGGCTTTT TACAGAATGG AGGAAGGGAT CCTCTCTGTC GGGTATTATG GTCATCGCCA      60

CGGGGGTGCC GTGCAGACCA CAGCTCTGTG CAGACTTCCG GAGTGGCAGG ACGTGCCAAT     120

ATACTGTCGT TGTATGATGT CCCCTCCCTG CCCTTGTTGT AGGTGCCCCC TTGTTTCTCT     180

CCCATCCTCA CTTCATCAAC GCTGACCCGG TTCTGGCAGA AGCGGTGACT GGCCTGCACC     240

CTAACCAGGA GGCACACTCC TTGTTCGTGG ACATCCACCC GGTGAGCCCC TGCCATCCTC     300

TGTGGGGGGT GGGTGATTCC TGGTTGGAGC ACACCTGGCT GCCTCCTCTC TCCCCAGGCA     360

GAGAGCTGCT GTGGGCTGGG GTGGTGGGAA GCCTGGCTTC TAGAATCTCG AGCCACCAAA     420

GTTCCTTACT                                                            430
```

(2) INFORMATION FOR SEQ ID NO:66:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:66:

```
GTGAGGGGCG AGAGGCGAGG GCCCCTGTCG CCAGGGAGAG GGGAGGGTGG GCCTGGCCAT      60

GGCTGCTCGG GAGTGGCAGG GACCAGAGAG CTCCTTCTTC CTTTGTCGTG AAGAGGGTGC     120

TGGGAGGATG AACACTCTTG AAGTTGGAGG AGGGATTTTA                            160
```

(2) INFORMATION FOR SEQ ID NO:67:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:67:

```
AACCGGGTCA GCGTTGAGGA                                                  20
```

(2) INFORMATION FOR SEQ ID NO:68:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:68:

```
TGCCAGAACC GGGTCAGCGT TGAGGAAGTG A                                     31
```

(2) INFORMATION FOR SEQ ID NO:69:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:69:

TCCTCAACGC TGACCCGGTT                    20

(2) INFORMATION FOR SEQ ID NO:70:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:70:

TCACTTCCTC AACGCTGACC CGGTTCTGGC A        31

(2) INFORMATION FOR SEQ ID NO:71:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:71:

AACCGGGTCG GCGTTGATGA                    20

(2) INFORMATION FOR SEQ ID NO:72:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:72:

TGCCAGAACC GGGTCGGCGT TGATGAAGTG A        31

(2) INFORMATION FOR SEQ ID NO:73:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:73:

TCATCAACGC CGACCCGGTT                    20

(2) INFORMATION FOR SEQ ID NO:74:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:74:

TCACTTCATC AACGCCGACC CGGTTCTGGC A                                31

(2) INFORMATION FOR SEQ ID NO:75:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:75:

AGCCATGGCC GGGCCCACCC T                                          21

(2) INFORMATION FOR SEQ ID NO:76:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:76:

CGAGCAGCCA TGGCCGGGCC CACCCTCCCC T                                31

(2) INFORMATION FOR SEQ ID NO:77:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:77:

AGGGTGGGCC CGGCCATGGC T                                          21

(2) INFORMATION FOR SEQ ID NO:78:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:78:

AGGGGAGGGT GGGCCCGGCC ATGGCTGCTC G                                31

(2) INFORMATION FOR SEQ ID NO:79:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "probe"

(xi) SEQUENCE DESCRIPTION: SEQ ID NO:79:

AGCCATGGCC AGGCCCACCC T                                            21

(2) INFORMATION FOR SEQ ID NO:80:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "probe"

(xi) SEQUENCE DESCRIPTION: SEQ ID NO:80:

CGAGCAGCCA TGGCCAGGCC CACCCTCCCC T                                 31

(2) INFORMATION FOR SEQ ID NO:81:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "probe"

(xi) SEQUENCE DESCRIPTION: SEQ ID NO:81:

AGGGTGGGCC TGGCCATGGC T                                            21

(2) INFORMATION FOR SEQ ID NO:82:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "probe"

(xi) SEQUENCE DESCRIPTION: SEQ ID NO:82:

AGGGGAGGGT GGGCCTGGCC ATGGCTGCTC G                                 31

(2) INFORMATION FOR SEQ ID NO:83:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "promoter"

(xi) SEQUENCE DESCRIPTION: SEQ ID NO:83:

TCCTGGGTGG GCTGGCGAAG TC                                           22

(2) INFORMATION FOR SEQ ID NO:84:

```
        (i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "promoter"

(xi) SEQUENCE DESCRIPTION: SEQ ID NO:84:

GTTTTGGGGC GGGAGCTGAT GAAG                                              24

(2) INFORMATION FOR SEQ ID NO:85:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "primer"

(xi) SEQUENCE DESCRIPTION: SEQ ID NO:85:

TGTAAAACGA CGGCCAGT                                                     18

(2) INFORMATION FOR SEQ ID NO:86:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "primer"

(xi) SEQUENCE DESCRIPTION: SEQ ID NO:86:

CAGGAAACAG CTATGACC                                                     18
```

INTRONIC AND POLYMORPHIC SR-BI NUCLEIC ACIDS AND USES THEREFOR

1. BACKGROUND OF THE INVENTION

Coronary heart disease is a major health risk throughout the industrialized world. Atherosclerosis, the most prevalent of cardiovascular diseases, is the principal cause of heart attack, stroke, and gangrene of the extremities, and thereby the principle cause of death in the United States. Although historically much emphasis has been placed on total plasma cholesterol levels as a risk factor for coronary heart disease, it has been clearly established that low levels of high density lipoprotein cholesterol (HDL-C) is an independent risk factor for this disease. Family and twin studies have shown that there are genetic components that affect HDL levels. However, mutations in the main protein components of HDL (ApoA1 and ApoAII) and in the enzymes that are known to be involved in HDL metabolism (e.g., CETP, HL, LPL and LCAT) do not explain all of the genetic factors affecting HDL levels in the general population (J. L. Breslow, in *The Metabolic and Molecular Bases of Inherited Disease,* C. R. Scriver, A. L. Beaudet, W. Sly, D. Valle, Eds. (McGraw-Hill, New York, 1995), pp 2031–2052; and S. M. Grundy, (1995) *J. Am. Med Assoc.* 256: 2849). This finding in combination with the fact that the mechanisms of HDL metabolism are poorly understood, suggests that there are other as yet unknown factors that contribute to the genetic variability of HDL levels.

One candidate factor is the SR-BI receptor, which has been shown to bind HDL and LDL cholesterol and mediate uptake into cells (Acton, S. et al., (1996) *Science* 271:518–520). SR-BI is likely to contribute to genetic lipoprotein variability, thereby playing a role in the development of atherosclerosis.

In addition, cholesterol gallstone formation could be caused by a defective SR-BI receptor, since the SR-BI receptor is likely to be involved in transferring HDL-cholesterol from extrahepatic tissues to the liver (reverse cholesterol transport) e.g. for incorporation into bile (J. L. Breslow, in *The Metabolic and Molecular Bases of Inherited Disease,* C. R. Scriver, A. L. Beaudet, W. Sly, D. Valle, Eds. (McGraw-Hill, New York, 1995), pp 2031–2052; S. M. Grundy, (1995) *J. Am. Med Assoc.* 256: 2849; G. Assman, A. von Eckardstein, H. B. Brewer Jr. in *The Metabolic and Molecular Bases of Inherited Disease,* C. R. Scriver, A. L. Beaudet, W. Sly, D. Valle, Eds. (McGraw-Hill, New York, 1995), pp 2053–2072; W. J. Johnson et al., (1991) *Biochem. Biophys. Acta* 1085:273; M. N. Pieters et al., (1994) Ibid 1225:125; and C. J. Fielding and P. E. Fielding, (1995) *J. Lipid Res* 36:211).

Further, a defective SR-BI receptor or abnormal levels of SR-BI receptor could influence the fertility of a subject, since SR-BI appears to be involved in HDL-cholesteryl ester delivery to steroidogenic tissues (ovary, adrenal glands and testis) for hormone synthesis (Acton, S. et al., (1996) *Science* 271:518–520; Landschulz, et al., (1996) *J. Clin. Invest.* 98:984–95; J. M. Anderson and J. M. Dietschy (1981) *J. Biol. Chem.* 256: 7362; M. S. Brown et al., (1979) *Recent Prog Horm. Res.* 35:215; J. T. Gwynne and J. F. Strauss III, (1982) *Endocr. Rev.* 3:299; B. D. Murphy et al., (1985) *Endocrinology* 116: 1587).

The SR-BI receptor (Scavenger Receptor-BI) is a scavenger receptor that mediates endocytosis of unmodified and modified lipoproteins, e.g., LDL, acetylated LDL, oxidized LDL (Acton et al. (1994) *J. Biol. Chem.* 269:21003), HDL ((Acton, S. et al., (1996) *Science* 271:518–520), anionic phospholipids (Rigotti et al. (1995) *J. Biol. Chem.* 270:16221), negatively charged liposomes and apoptotic cells (Fukasawa et al. (1996) *Exp. Cell Res.* 222:246). The human SR-BI receptor (also termed "CLA-1") exists in two differentially spliced forms (Calvo and Vega (1993) *J. Biol. Chem.* 268:18929). The predominant form of human SR-BI is a protein of 509 amino acids. The shorter form of the SR-BI receptor has 409 amino acids, and is lacking the 100 amino acids located 42 amino acids downstream of the initiation codon (Calvo and Vega, supra). The nucleotide sequence of a cDNA encoding human SR-BI is disclosed in Calvo and Vega, supra) and the nucleotide sequence of a cDNA encoding hamster SR-BI is disclosed in Acton et al. (1994) *J. Biol. Chem.* 269:21003 and in PCT Application WO 96/00288.

2. SUMMARY OF THE INVENTION

The present invention is based at least in part on the discovery of the genomic structure of the human SR-BI gene and on the identification of polymorphic regions within the gene, which are believed to be associated with specific diseases or disorders. The human SR-BI gene contains 12 coding exons and one non coding exon (exon 13). The structure of the gene and the position of the introns relative to the nucleotide sequence of the exons are shown in FIGS. 1, 2, and 3.

Several polymorphic regions, which are believed to be associated with specific diseases or disorders, have been found in the human SR-BI gene by analyzing the DNA of a specific population of individuals. This population was chosen for the study since they have a known HDL level (either low, normal, or high HDL level). The individuals were Spanish individuals of known age, and of known body mass index, and triglyceride levels. One polymorphism is a nucleotide polymorphism at nucleotide 41 of exon 8: about 35% of the individuals analyzed are homozygous for an allele having a cytidine at this position; about 17% of the individuals analyzed are homozygous for an allele having a thymidine at this position; and about 48% of the individuals analyzed are heterozygous, comprising one allele of each. This nucleotide substitution change does not result in an amino acid change. A second nucleotide polymorphism was found in about 24% of the population and consists of a substitution of the cytidine at position 54 of intron 5 with a thymidine.

Specific allelic variants of these polymorphic regions, as well as other polymorphic regions in the SR-BI gene are believed to be associated with specific diseases or disorders, e.g., diseases or disorders characterized by an aberrant SR-BI activity. Genetic analysis of populations of individuals having an aberrant SR-BI activity will reveal the disease or disorder that is associated with a specific allelic variant of a polymorphic region of an SR-BI gene, e.g., diseases or disorders associated with an aberrant SR-BI activity. Specific allelic variants of SR-BI polymorphic regions can be associated with an abnormal or inappropriate lipid levels, gallstone formation, abnormal body mass index (e.g., obesity or cachexia), or cardiovascular diseases, e.g., atherosclerosis.

In one embodiment, the invention provides isolated nucleic acids comprising an intronic sequence from an SR-BI gene. In a preferred embodiment, the SR-BI gene is a human gene. In another preferred embodiment, the nucleic acid of the invention has a nucleotide sequence set forth in FIG. 2 or in any of the intronic sequences in SEQ ID Nos. 1–84, complements thereof, or homologs thereof. In yet another embodiment, the intronic sequence of the nucleic acid is capable of hybridizing under an appropriate stringency to a nucleic acid having an intronic nucleotide sequence set forth in any of SEQ ID Nos. 1–84 or complements thereof.

Other preferred nucleic acids of the invention comprise at least an allelic variant of a polymorphic region. A preferred allele has a polymorphic region that is located in an exon and has, e.g., a nucleotide sequence set forth in SEQ ID NO. 65. The isolated nucleic acid preferably comprises from about 15 to about 30 nucleotides and can comprise, e.g., a nucleotide sequence selected from the group consisting of SEQ ID NO. 41 to SEQ ID NO. 64. The isolated nucleic acid can be double stranded or single stranded and can further comprise a label.

The nucleic acids of the invention can be used, e.g., in prognostic, diagnostic, and therapeutic methods. For example, the nucleic acids of the invention can be used as probes or primers to determine whether a subject has or is at risk of developing a disease or disorder associated with a specific allelic variant of an SR-BI polymorphism, e.g., a disease or disorder associated with an aberrant SR-BI activity.

The invention further describes vectors comprised of the claimed nucleic acids; host cells transfected with said vectors whether prokaryotic or eukaryotic; and transgenic non-human animals which contain a heterologous form of a functional or non-functional SR-BI allele described herein. Such a transgenic animal can serve as an animal model for studying, e.g., the effect of specific allelic variations, including mutations of an SR-BI gene or for use in drug screening or recombinant protein production.

In another embodiment, the invention provides a kit for amplifying and/or for determining the molecular structure of at least a portion of an SR-BI gene, comprising a probe or primer capable of hybridizing to an SR-BI gene and instructions for use. In one embodiment, the probe or primer is capable of hybridizing to an SR-BI intron. In another embodiment, the probe or primer is capable of hybridizing to an allelic variant of a polymorphic region. In a preferred embodiment, the polymorphic region is located in an exon, such as exon 8. In a preferred embodiment, determining the molecular structure of a region of an SR-BI gene comprises determining the identity of the allelic variant of the polymorphic region. Determining the molecular structure of at least a portion of an SR-BI gene can comprise determining the identity of at least one nucleotide or determining the nucleotide composition, e.g., the nucleotide sequence.

A kit of the invention can be used, e.g., for determining whether a subject has or is at risk of developing a disease associated with a specific allelic variant of a polymorphic region of an SR-BI gene. In a preferred embodiment, the invention provides a kit for determining whether a subject has or is at risk of developing a disease or condition associated with abnormal lipid metabolism, inappropriate lipid levels, a cardiovascular disease such as atherosclerosis, gallstone formation, or an abnormal body mass index. The disease or condition can be associated with an aberrant SR-BI activity, which can result, e.g., from a mutation in the SR-BI gene. The kit of the invention can also be used in selecting the appropriate drug to administer to a subject to treat a disease or condition, such as a disease or condition set forth above. In fact, pharmacogenetic studies have shown that the genetic background of individuals play a role in determining the response of an individual to a specific drug. Thus, determining the allelic variants of SR-BI polymorphic regions of an individual can be useful in predicting how an individual will respond to a specific drug, e.g, a drug for treating a disease or disorder associated with an aberrant SR-BI activity and/or a cardiovascular disease or a disease associated with an aberrant lipid level.

The invention further provides methods for determining the molecular structure of at least a portion of an SR-BI gene. In a preferred embodiment, the method comprises contacting a sample nucleic acid comprising an SR-BI gene sequence with a probe or primer having a sequence which is complementary to an SR-BI gene sequence and comparing the molecular structure of the sample nucleic acid with the molecular structure of a control (known) SR-BI gene (e.g., an SR-BI gene from a human not afflicted with a cardiovascular disease or a disease associated with an aberrant SR-BI activity). The method of the invention can be used for example in determining the molecular structure of at least a portion of an exon, an intron, or the promoter. In a preferred embodiment, the method comprises determining the identity of at least one nucleotide. In another preferred embodiment, the method comprises determining the nucleotide content of at least a portion of an SR-BI gene, such as by sequence analysis. In yet another embodiment, determining the molecular structure of at least a portion of an SR-BI gene is carried out by single-stranded conformation polymorphism. In yet another embodiment, the method is an oligonucleotide ligation assay. Other methods within the scope of the invention for determining the molecular structure of at least a portion of an SR-BI gene include hybridization of allele-specific oligonucleotides, sequence specific amplification, and primer specific extension.

In at least some of the methods of the invention, the probe or primer is allele specific. Preferred probes or primers are single stranded nucleic acids, which optionally are labeled.

The methods of the invention can be used for determining the identity of the allelic variant of a polymorphic region of a human SR-BI gene present in a subject. For example, the method of the invention can be used for determining whether a subject has, or is at risk of developing, a disease or condition associated with a specific allelic variant of a polymorphic region in the human SR-BI gene. In one embodiment, the disease or condition is characterized by an aberrant SR-BI activity, such as an aberrant SR-BI protein level, which can result from an aberrant expression of an SR-BI gene. The disease or condition can be an abnormal lipid metabolism, inappropriate lipid levels, atherosclerosis, gallstone formation or an abnormal body mass index. Accordingly, the invention provides methods for diagnosing cardiovascular diseases, diseases associated with an abnormal lipid level, as well as diseases or disorders characterized by an aberrant SR-BI activity.

The methods of the invention can also be used in selecting the appropriate drug to administer to a subject to treat a disease or condition, such as an abnormal lipid metabolism, inappropriate lipid levels, a cardiovascular disease such as atherosclerosis, gallstone formation, or an abnormal body mass index. In fact, specific allelic variants of SR-BI polymorphic regions may be associated with a specific response of an individual having such an allele to a specific drug. For example, a specific SR-BI allele may encode an SR-BI protein having a modified affinity for certain types of molecules, e.g, lipids. Accordingly, the action of a drug necessitating interaction with an SR-BI protein will be different in individuals carrying such an SR-BI allele.

In a further embodiment, the invention provides a method for treating a subject having a disease or condition associated with a specific allelic variant of a polymorphic region of an SR-BI gene. In one embodiment, the method comprises (a) determining the identity of the allelic variant; and (b) administering to the subject a compound that compensates for the effect of the specific allelic variant. In a preferred embodiment, the specific allelic variant is a mutation. The mutation can be located, e.g., in a promoter region, an intron, or an exon of the gene. In one embodiment, the compound modulates (i.e., agonizes or antagonizes) SR-BI protein levels. In a preferred embodiment, the compound is selected from the group consisting of a nucleic acid, a protein, a peptidomimetic, or a small molecule. The compound can be, an for example, SR-BI protein.

The invention also provides probes and primers comprising substantially purified oligonucleotides, which correspond to a region of nucleotide sequence which hybridizes to at least 6 consecutive nucleotides of the sequence set forth as SEQ ID Nos: 1, 2, or 3 or to the complement of the sequences set forth as SEQ ID Nos: 1, 2, or 3; or naturally occurring mutants thereof In preferred embodiments, the probe/primer further includes a label group attached thereto, which is capable of being detected.

Other features and advantages of the invention will be apparent from the following detailed description and claims.

3. BRIEF DESCRIPTION OF THE FIGURES

FIG. 1 is a schematic depiction of the chromosomal structure of the human SR-BI gene indicating the introns (1 through 12) and exons (I–XIII). Black boxes represent coding exons (exons I–XII) and the white box represents the non-coding exon (exon XIII).

FIGS. 2A–2G represent the nucleotide sequence of the exons (underlined sequence) of the human SR-BI gene, portions of the introns which are adjacent to the exons, and 3' promoter sequence (SEQ ID Nos. 5–40). The putative 5' end of the cDNA, as predicted by GRAIL is indicated in italics. The TATA-like box is indicated in italics and is boxed. Bold sequences correspond to the nucleotide sequence or the complement of the nucleotide sequence of preferred primers for amplifying each of the exons or a promoter region. The nucleotide polymorphisms in exon 8 and intron 5 are boxed.

FIGS. 3A–3B show the nucleotide sequence of the full length human SR-BI cDNA (SEQ ID NO. 1) and the position of introns 1–12 relative to the nucleotide sequence of the exons. The nucleotide polymorphism in exon 8 is boxed.

4. DETAILED DESCRIPTION OF THE INVENTION

4.1. General

The present invention is based at least in part on the discovery of the genomic structure of the human SR-BI gene and on the identification of polymorphic regions within the gene. At least some of these polymorphic regions may correlate with specific diseases or conditions.

As shown in FIG. 1, the human SR-BI gene is at least 50 kilobase pairs long and has 12 coding exons, one non-coding exon (exon 13), and 12 introns. The exons are numbered 1 to 13 from 5' to 3' and the introns are labeled 1 through 12 from 5' to 3'. Exon 1 corresponds to the first exon located downstream of the promoter and contains the initiation codon. Intron 1 is located immediately downstream of exon I (see FIG. 1). The position of the introns relative to the nucleotide sequence of the full length cDNA encoding SR-BI is shown in FIG. 2. The nucleotide sequence of the human SR-BI cDNA, shown in FIG. 3 and in SEQ ID NO. 1 encodes a protein of 509 amino acids. SEQ ID NO. 1 contains the nucleotide sequence of the cDNA disclosed in Calvo and Vega (1993) J. Biol. Chem. 268:18929, and contains in addition a complete 5' end. The amino acid sequence of the protein set forth in SEQ ID NO. 2 is identical to the Cla-I protein disclosed in Calvo and Vega (1993) J. Biol. Chem. 268:18929. As set forth in Calvo and Vega, supra, differential splicing of the human SR-BI gene also results in a short mRNA lacking 300 nucleotides located 126 nucleotides downstream of the initiation codon, i.e., lacking exons 2 and 3 set forth in FIG. 3, which encodes a protein of 409 amino acids. The shorter protein is referred to herein as "splice variant". The nucleotide sequence of a full length cDNA encoding the splice variant is set forth in SEQ ID NO. 3 and the amino acid sequence of the SR-BI splice variant protein encoded by this nucleotide sequence is set forth in SEQ ID NO. 4. The splice variant is rare relative to the 509 amino acid SR-BI protein.

FIG. 2 shows the nucleotide sequence of the 3' end of the SR-BI promoter. Additional promoter sequence is disclosed in U.S. patent application Ser. No. 08/812,204 by Acton, incorporated herein by reference.

Set forth below in Table I are the locations and sizes of the exons in the human SR-BI gene relative to the nucleotide sequence of a full length cDNA encoding human SR-BI protein (SEQ ID NO. 1), in which nucleotide 1 corresponds to the first nucleotide in the isolated transcript. Table I also indicates the portions of the human SR-BI protein encoded by each of these exons. Amino acid 1 is the initiating methionine. Also indicated is the length of the intron located downstream of each of the exons.

TABLE I

| | Nucleotide position | Amino acid position | Size of intron |
|---|---|---|---|
| Exon 1 | 1–244 | 1–42 | intron 1: >2827 |
| Exon 2 | 245–402 | 43–95 | intron 2: 2429 |
| Exon 3 | 403–544 | 95–142 | intron 3: 567 |
| Exon 4 | 545–748 | 143–210 | intron 4: 2229 |
| Exon 5 | 749–844 | 211–242 | intron 5: 1580 |
| Exon 6 | 845–960 | 243–281 | intron 6: >10532 |
| Exon 7 | 961–1127 | 281–337 | intron 7: >3985 |
| Exon 8 | 1228–1246 | 337–376 | intron 8: >11321 |
| Exon 9 | 1247–1320 | 377–401 | intron 9: 7562 |
| Exon 10 | 1321–1372 | 401–418 | intron 10: 902 |
| Exon 11 | 1373–1519 | 419–467 | intron 11: 3547 |
| Exon 12 | 1520–1648 | 468–509 | intron 12: >4578 |
| Exon 13 | 1649–2630 | | |

FIG. 2 shows the nucleotide sequence of portions of the introns which are adjacent to the exons. The nucleotide sequence of each of the exons and adjacent portions of introns shown in FIG. 2 are set forth in SEQ ID Nos. 5 to 16. The portions of each of the introns shown in FIG. 2 are set forth in SEQ ID Nos. 18 to 40. For convenience, the identity of the sequences referred to as SEQ ID Nos. 1 to 40 are set forth below in Table II:

TABLE II

| | |
|---|---|
| SEQ ID NO. 1 | full length cDNA encoding human SR-BI; |
| SEQ ID NO. 2 | full length amino acid sequence of human SR-BI protein; |
| SEQ ID NO. 3 | full length cDNA encoding splice variant of human SR-BI (Calvo and Vega, supra); |

TABLE II-continued

| | |
|---|---|
| SEQ ID NO. 4 | full length amino acid sequence of splice variant of human SR-BI protein (Calvo and Vega, supra); |
| SEQ ID NO. 5 | 3' end of promoter, exon 1, and 5' end of intron 1; |
| SEQ ID NO. 6 | 3' end of intron 1, exon 2, and 5' end of intron 2; |
| SEQ ID NO. 7 | 3' end of intron 2, exon 3, and 5' end of intron 3; |
| SEQ ID NO. 8 | 3' end of intron 3, exon 4, and 5' end of intron 4; |
| SEQ ID NO. 9 | 3' end of intron 4, exon 5, and 5' end of intron 5; |
| SEQ ID NO. 10 | 3' end of intron 5, exon 6, and 5' end of intron 6; |
| SEQ ID NO. 11 | 3' end of intron 6, exon 7, and 5' end of intron 7; |
| SEQ ID NO. 12 | 3' end of intron 7, exon 8, and 5' end of intron 8; |
| SEQ ID NO. 13 | 3' end of intron 8, exon 9, and 5' end of intron 9; |
| SEQ ID NO. 14 | 3' end of intron 9, exon 10, and 5' end of intron 10; |
| SEQ ID NO. 15 | 3' end of intron 10, exon 11, and 5' end of intron 11; |
| SEQ ID NO. 16 | 3' end of intron 11, exon 12, and 5' end of intron 12; |
| SEQ ID NO. 17 | 3' end of promoter; |
| SEQ ID NO. 18 | 5' end of intron 1; |
| SEQ ID NO. 19 | 3' end of intron 1; |
| SEQ ID NO. 20 | 5' end of intron 2; |
| SEQ ID NO. 21 | 3' end of intron 2; |
| SEQ ID NO. 22 | 5' end of intron 3; |
| SEQ ID NO. 23 | 3' end of intron 3; |
| SEQ ID NO. 24 | 5' end of intron 4; |
| SEQ ID NO. 25 | 3' end of intron 4; |
| SEQ ID NO. 26 | 5' end of intron 5; |
| SEQ ID NO. 27 | 3' end of intron 5; |
| SEQ ID NO. 28 | 5' end of intron 6; |
| SEQ ID NO. 29 | 3' end of intron 6; |
| SEQ ID NO. 30 | 5' end of intron 7; |
| SEQ ID NO. 31 | 3' end of intron 7; |
| SEQ ID NO. 32 | 5' end of intron 8; |
| SEQ ID NO. 33 | 3' end of intron 8; |
| SEQ ID NO. 34 | 5' end of intron 9; |
| SEQ ID NO. 35 | 3' end of intron 9; |
| SEQ ID NO. 36 | 5' end of intron 10; |
| SEQ ID NO. 37 | 3' end of intron 10; |
| SEQ ID NO. 38 | 5' end of intron 11; |
| SEQ ID NO. 39 | 3' end of intron 11; and |
| SEQ ID NO. 40 | 5' end of intron 12. |

An analysis of the human SR-BI gene in a population of individuals chosen because these individuals had a known age, known HDL levels, known body mass index, and known triglycerides level revealed the existence of several polymorphisms in the SR-BI gene in this population. These polymorphisms were identified by performing single stranded conformation polymorphism (SSCP) analysis of genomic DNA from families as described in Example 3, using PCR primers complementary to intronic sequences surrounding each of the exons. The nucleotide sequence of these PCR primers (having SEQ ID Nos. 41–64) is shown in Table III (in the Examples).

The results indicated the presence of at least two polymorphic regions in the human SR-BI gene in the population studied. One polymorphic region in the human SR-BI gene is located in the eighth exon. More specifically, the polymorphism corresponds to the replacement of the cytidine at position 41 of the exon with a thymidine. The nucleotide sequence of exon 8 of this allele is set forth in SEQ ID NO. 65 (SEQ ID NO. 65 is identical to SEQ ID NO. 12, except for nucleotide 41 of the exon sequence which is a thymidine). About 3% of the individuals of a Spanish population were found to be homozygous for the allele having a thymidine at position 41 (i.e., SR-BI sequence originally disclosed); about 17% of the individuals were found to be homozygous for the allele having a thymidine at position 41 of exon 8; and about 48% of the individuals were found to be heterozygous, i.e., having one allele having a cytidine at position 41 and one allele having a thymidine at position 41.

A second polymorphic region in the human SR-BI gene is located in the fifth intron. More specifically, the polymorphism corresponds to the replacement of the cytidine at position 54 of the intron (position 1 being defined as the first nucleotide in the intron) with a thymidine. This nucleotide substitution destroys the ApaI restriction site which is present when the nucleotide at position 54 is a cytidine. The nucleotide sequence of the 5' end of intron 5 of this allele is set forth in SEQ ID NO. 66 (SEQ ID NO. 66 is identical to SEQ ID NO. 26, except for nucleotide 54 which is a thymidine).

Further analysis of the human SR-BI gene is likely to reveal the existence of yet other polymorphic regions. Such analysis can be performed using the methods described herein and genomic DNA from random subjects or subjects of families associated with specific diseases. For example, the polymorphism studies described herein can also be applied to populations in which cholesterol gallstones are prevalent.

Accordingly, the invention provides nucleic acids, e.g., intronic sequences useful as probes or primers for determining the identity of an allelic variant of an SR-BI polymorphic region. The invention also provides methods for determining the identity of the alleles of a specific polymorphic region of an SR-BI gene. Such methods can be used, for example, to determine whether a subject has or is at risk of developing a disease or condition associated with one or more specific alleles of polymorphic regions of an SR-BI gene. In a preferred embodiment, the disease or condition is caused or contributed to by an aberrant SR-BI bioactivity. Other aspects of the invention are described below or will be apparent to one of skill in the art in light of the present disclosure.

4.2 Definitions

For convenience, the meaning of certain terms and phrases employed in the specification, examples, and appended claims are provided below.

The term "allele", which is used interchangeably herein with "allelic variant" refers to alternative forms of a gene or portions thereof Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions, and insertions of nucleotides. An allele of a gene can also be a form of a gene containing a mutation.

The term "allelic variant of a polymorphic region of an SR-BI gene" refers to a region of an SR-BI gene having one of several nucleotide sequences found in that region of the gene in other individuals.

"Biological activity" or "bioactivity" or "activity" or "biological function", which are used interchangeably, for the purposes herein when applied to SR-BI means an effector or antigenic function that is directly or indirectly performed by an SR-BI polypeptide (whether in its native or denatured conformation), or by any subsequence (fragment) thereof. Biological activities include binding to a ligand, e.g., a lipid or lipoprotein, such as LDL or modified forms thereof, or HDL or modified forms thereof Other molecules which can bind an SR-BI receptor include anionic molecules, such as anionic phospholipids, negatively charged liposomes, and apoptotic cells. Another biological activity of an SR-BI protein includes endocytosis of a ligand interacting with the receptor. A biological activity is also intended to include binding to a protein, such as binding to the cytoplasmic domain of SR-BI. Yet other biological activities include signal transduction from the receptor, modulation of expression of genes responsive to binding of a ligand to an SR-BI receptor, and other biological activities, whether presently known or inherent. An SR-BI bioactivity can be modulated by directly affecting an SR-BI protein. Alternatively, an SR-BI bioactivity can be modulated by modulating the level of an SR-BI protein, such as by modulating expression of an SR-BI gene. Antigenic functions include possession of an epitope or antigenic site that is capable of cross-reacting with antibodies raised against a naturally occurring or denatured SR-BI polypeptide or fragment thereof.

Biologically active SR-BI polypeptides include polypeptides having both an effector and antigenic function, or only one of such functions. SR-BI polypeptides include antagonist polypeptides and native SR-BI polypeptides, provided that such antagonists include an epitope of a native SR-BI polypeptide. An effector function of SR-BI polypeptide can be the ability to bind to a ligand, e.g., a lipid or modified form thereof.

As used herein the term "bioactive fragment of a SR-BI protein" refers to a fragment of a full-length SR-BI protein, wherein the fragment specifically mimics or antagonizes the activity of a wild-type SR-BI protein. The bioactive fragment preferably is a fragment capable of binding to a second molecule, such as a ligand.

The term "an aberrant activity" or "abnormal activity", as applied to an activity of a protein such as SR-BI, refers to an activity which differs from the activity of the wild-type or native protein or which differs from the activity of the protein in a healthy subject, e.g., a subject not afflicted with a disease associated with a specific allelic variant of an SR-BI polymorphism. An activity of a protein can be aberrant because it is stronger than the activity of its native counterpart. Alternatively, an activity can be aberrant because it is weaker or absent related to the activity of its native counterpart. An aberrant activity can also be a change in an activity. For example an aberrant protein can interact with a different protein relative to its native counterpart. A cell can have an aberrant SR-BI activity due to overexpression or underexpression of the gene encoding SR-BI. An aberrant SR-BI activity can result, e.g., from a mutation in the gene, which results, e.g., in lower or higher binding affinity of a lipid to the SR-BI protein encoded by the mutated gene. An aberrant SR-BI activity can also result from a lower or higher level of SR-BI receptor on cells, which can result, e.g., from a mutation in the 5' flanking region of the SR-BI gene or any other regulatory element of the SR-BI gene, such as a regulatory element located in an intron. Accordingly, an aberrant SR-BI activity can result from an abnormal SR-BI promoter activity.

The terms "abnormal SR-BI promoter activity", "aberrant SR-BI promoter activity", "abnormal SR-BI transcriptional activity" and "aberrant SR-BI transcriptional activity", which are used interchangeably herein, refer to the transcriptional activity of an SR-BI promoter which differs from the transcriptional activity of the same promoter in a healthy subject. An abnormal SR-BI activity can result from a higher or lower transcriptional activity than that in a healthy subject. An aberrant SR-BI promoter activity can result, e.g., from the presence of a genetic lesion in a regulatory element, such as in a regulatory element located in the promoter. An "aberrant SR-BI promoter activity" is also intended to refer to the transcriptional activity of an SR-BI promoter which is functional (capable of inducing transcription of a gene to which it is operably linked) in tissues or cells in which the "natural" or wild-type SR-BI promoter is not functional or which is non functional in tissues or cells in which the "natural" or wild-type SR-BI promoter is functional. Thus, a tissue distribution of SR-BI in a subject which differs from the tissue distribution of SR-BI in a "normal" or "healthy" subject, can be the result of an abnormal transcriptional activity from the SR-BI promoter region. Such an abnormal transcriptional activity can result, e.g., from one or more mutations in a promoter region, such as in a regulatory element thereof. An abnormal transcriptional activity can also result from a mutation in a transcription factor involved in the control of SR-BI gene expression.

The term "body mass index" or "BMI" refers to the ratio of weight (kg)/height (m$^2$) and can be used to define whether a subject is overweight. Typically, a subject is underweight if he has a BMI<20; normal if he has a BMI of 20–25, overweight if he has a BMI of 25–30, obese if he has a BMI of 30–40 and severely obese if he has a BMI>40.

As used herein, a subject has an "abnormal body mass" or "abnormal body mass index" or "aberrant body mass" or "aberrant body mass index" if his body mass index is outside the range defined for a healthy or normal subject, i.e., BMI of 20–25. A disorder of body mass include any disorder affecting the body mass of a subject such that his body mass is outside the normal range. For example, obesity is a disorder of body mass. Wasting is also a disorder of body mass. An abnormal body mass index can have a hormonal origin, e.g., in premenopausal women.

The term "cardiovascular disorder" refers to a disease or disorder of the cardiovascular system and includes ischemia, restenosis, congestive heart failure, and atherosclerosis.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, the term "gene" or "recombinant gene" refers to a nucleic acid molecule comprising an open reading frame and including at least one exon and (optionally) an intron sequence. The term "intron" refers to a DNA sequence present in a given gene which is spliced out during mRNA maturation.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present invention.

The term "a homolog of a nucleic acid" refers to a nucleic acid having a nucleotide sequence having a certain degree of homology with the nucleotide sequence of the nucleic acid or complement thereof A homolog of a double stranded nucleic acid having SEQ ID NO. x is intended to include nucleic acids having a nucleotide sequence which has a certain degree of homology with SEQ ID NO. x or with the complement thereof. Preferred homologs of nucleic acids are capable of hybridizing to the nucleic acid or complement thereof.

The term "interact" as used herein is meant to include detectable interactions between molecules, such as can be detected using, for example, a hybridization assay. The term interact is also meant to include "binding" interactions between molecules. Interactions may be, for example, protein-protein, protein-nucleic acid, protein-small molecule or small molecule-nucleic acid in nature.

The term "intronic sequence" or "intronic nucleotide sequence" refers to the nucleotide sequence of an intron or portion thereof.

The term "isolated" as used herein with respect to nucleic acids, such as DNA or RNA, refers to molecules separated from other DNAs or RNAs, respectively, that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "lipid" shall refer to a fat or fat-like substance that is insoluble in polar solvents such as water. The term "lipid" is intended to include true fats (e.g. esters of fatty acids and glycerol); lipids (phospholipids, cerebrosides, waxes); sterols (cholesterol, ergosterol) and lipoproteins (e.g. HDL, LDL and VLDL).

The term "locus" refers to a specific position in a chromosome. For example, a locus of an SR-BI gene refers to the chromosomal position of the SR-BI gene.

The term "modulation" as used herein refers to both upregulation, (i.e., activation or stimulation), for example by agonizing; and downregulation (i.e. inhibition or suppression), for example by antagonizing of a bioactivity (e.g. expression of a gene).

The term "molecular structure" of a gene or a portion thereof refers to the structure as defined by the nucleotide content (including deletions, substitutions, additions of one or more nucleotides), the nucleotide sequence, the state of methylation, and/or any other modification of the gene or portion thereof.

The term "mutated gene" refers to an allelic form of a gene, which is capable of altering the phenotype of a subject having the mutated gene relative to a subject which does not have the mutated gene. If a subject must be homozygous for this mutation to have an altered phenotype, the mutation is said to be recessive. If one copy of the mutated gene is sufficient to alter the genotype of the subject, the mutation is said to be dominant. If a subject has one copy of the mutated gene and has a phenotype that is intermediate between that of a homozygous and that of a heterozygous (for that gene) subject, the mutation is said to be co-dominant.

As used herein, the term "nucleic acid" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides. Deoxyribonucleotides include deoxyadenosine, deoxycytidine, deoxyguanosine, and deoxythymidine. For purposes of clarity, when referring herein to a nucleotide of a nucleic acid, which can be DNA or an RNA, the terms "adenosine", "cytidine", "guanosine", and "thymidine" are used. It is understood that if the nucleic acid is RNA, a nucleotide having a uracil base is uridine.

The term "nucleotide sequence complementary to the nucleotide sequence set forth in SEQ ID NO. x" refers to the nucleotide sequence of the complementary strand of a nucleic acid strand having SEQ ID NO. x. The term "complementary strand" is used herein interchangeably with the term "complement". The complement of a nucleic acid strand can be the complement of a coding strand or the complement of a non-coding strand. When referring to double stranded nucleic acids, the complement of a nucleic acid having SEQ ID NO. x refers to the complementary strand of the strand having SEQ ID NO. x or to any nucleic acid having the nucleotide sequence of the complementary strand of SEQ ID NO. x. When referring to a single stranded nucleic acid having the nucleotide sequence SEQ ID NO. x, the complement of this nucleic acid is a nucleic acid having a nucleotide sequence which is complementary to that of SEQ ID NO. x. The nucleotide sequences and complementary sequences thereof are always given in the 5' to 3' direction. The term "complement" and "reverse complement" are used interchangeably herein.

A "non-human animal" of the invention can include mammals such as rodents, non-human primates, sheep, goats, horses, dogs, cows, chickens, amphibians, reptiles, etc. Preferred non-human animals are selected from the rodent family including rat and mouse, most preferably mouse, though transgenic amphibians, such as members of the Xenopus genus, and transgenic chickens can also provide important tools for understanding and identifying agents which can affect, for example, embryogenesis and tissue formation. The term "chimeric animal" is used herein to refer to animals in which an exogenous sequence is found, or in which an exogenous sequence is expressed in some but not all cells of the animal. The term "tissue-specific chimeric animal" indicates that an exogenous sequence is present and/or expressed or disrupted in some tissues, but not others.

The term "operably linked" is intended to mean that the promoter is associated with the nucleic acid in such a manner as to facilitate transcription of the nucleic acid from the promoter.

The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles. A polymorphic region can also be several nucleotides long.

A "polymorphic gene" refers to a gene having at least one polymorphic region.

The terms "protein", "polypeptide" and "peptide" are used interchangeably herein when referring to a gene product.

The term "recombinant protein" refers to a polypeptide which is produced by recombinant DNA techniques, wherein generally, DNA encoding the polypeptide is inserted into a suitable expression vector which is in turn used to transform a host cell to produce the heterologous protein.

A "regulatory element", also termed herein "regulatory sequence" is intended to include elements which are capable of modulating transcription from a basic promoter and include elements such as enhancers and silencers. The term "enhancer", also referred to herein as "enhancer element", is intended to include regulatory elements capable of increasing, stimulating, or enhancing transcription from a basic promoter. The term "silencer", also referred to herein as "silencer element" is intended to include regulatory elements capable of decreasing, inhibiting, or repressing transcription from a basic promoter. Regulatory elements are typically present in 5' flanking regions of genes. However, regulatory elements have also been shown to be present in other regions of a gene, in particular in introns. Thus, it is possible that SR-BI genes have regulatory elements located in introns, exons, coding regions, and 3' flanking sequences. Such regulatory elements are also intended to be encompassed by the present invention and can be identified by any of the assays that can be used to identify regulatory elements in 5' flanking regions of genes.

The term "regulatory element" further encompasses "tissue specific" regulatory elements, i.e., regulatory elements which effect expression of the selected DNA sequence preferentially in specific cells (e.g., cells of a specific tissue). Gene expression occurs preferentially in a specific cell if expression in this cell type is significantly higher than expression in other cell types. The term "regulatory element" also encompasses non-tissue specific regulatory elements, i.e., regulatory elements which are active in most cell types. Furthermore, a regulatory element can be a constitutive regulatory element, i.e., a regulatory element which constitutively regulates transcription, as opposed to a regulatory element which is inducible, i.e., a regulatory element which is active primarily in response to a stimulus. A stimulus can be, e.g., a molecule, such as a hormone, cytokine, heavy metal, phorbol ester, cyclic AMP (cAMP), or retinoic acid.

Regulatory elements are typically bound by proteins, e.g., transcription factors. The term "transcription factor" is intended to include proteins or modified forms thereof, which interact preferentially with specific nucleic acid sequences, i.e., regulatory elements, and which in appropriate conditions stimulate or repress transcription. Some transcription factors are active when they are in the form of a monomer. Alternatively, other transcription factors are active in the form of a dimer consisting of two identical proteins or different proteins (heterodimer). Modified forms of transcription factors are intended to refer to transcription factors having a postranslational modification, such as the attachment of a phosphate group. The activity of a transcription factor is frequently modulated by a postranslational modification. For example, certain transcription factors are active only if they are phosphorylated on specific residues. Alternatively, transcription factors can be active in the absence of phosphorylated residues and become inactivated by phosphorylation. A list of known transcription factors and their DNA binding site can be found, e.g., in public databases, e.g., TFMATRIX Transcription Factor Binding Site Profile database.

As used herein, the term "specifically hybridizes" or "specifically detects" refers to the ability of a nucleic acid molecule of the invention to hybridize to at least approximately 6, 12, 20, 30, 40, 50, 60, 70, 80, 90, 100, 110, 120, 130 or 140 consecutive nucleotides of either strand of an SR-BI gene.

"SR-BI" or "SR-BI receptor" refers to a class B scavenger receptor that has been shown to bind HDL cholesterol and mediate uptake into cells (Acton, S. et al., *Science* 271:518–520). SR-BI has also been shown to bind with high affinity to modified proteins (e.g. acetylated LDL, oxidized LDL, maleylated bovine serum albumin) and native LDL (Acton, et al., (1994) *J. Biochem.* 269:21003–21009). Further, SR-BI has been shown to bind anionic phospholipids, such as phosphatidylserine and phosphatidylinositol, but not zwitterionic phospholipids, such as phosphatidylcholine, phosphatidylethanolamine and sphingomyelin. Competition studies suggest that anionic phospholipids bind to SR-BI at a site close to or identical with the sites of native and modified LDL binding and that the interaction may involve polyvalent binding via multiple anionic phospholipid molecules (Rigotti, A., S. Acton and M. Krieger (1995) *J. Biochem* 270:16221–16224). SR-BI has also been shown to bind to negatively charged liposomes and apoptotic cells. The human SR-BI protein is described in Calvo et al. (1993) J. Biol. Chem. 268:18929 and hamster SR-BI is described in International Patent Application Number WO 96/00288 entitled "Class B1 and C1 Scavenger Receptors" by Acton, S. et al.

As used herein, the term "transfection" means the introduction of a nucleic acid, e.g., an expression vector, into a recipient cell by nucleic acid-mediated gene transfer. The term "transduction" is generally used herein when the transfection with a nucleic acid is by viral delivery of the nucleic acid. "Transformation", as used herein, refers to a process in which a cell's genotype is changed as a result of the cellular uptake of exogenous DNA or RNA, and, for example, the transformed cell expresses a recombinant form of a polypeptide or, in the case of anti-sense expression from the transferred gene, the expression of a naturally-occurring form of the recombinant protein is disrupted.

As used herein, the term "transgene" refers to a nucleic acid sequence which has been introduced into a cell. Daughter cells deriving from a cell in which a transgene has been introduced are also said to contain the transgene (unless it has been deleted). A transgene can encode, e.g., a polypeptide, or an antisense transcript, partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). Alternatively, a transgene can also be present in an episome. A transgene can include one or more transcriptional regulatory sequence and any other nucleic acid, (e.g. intron), that may be necessary for optimal expression of a selected nucleic acid.

A "transgenic animal" refers to any animal, preferably a non-human animal, e.g. a mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of a protein, e.g. either agonistic or antagonistic forms. However, transgenic animals in which the recombinant gene is silent are also contemplated, as for example, the FLP or CRE recombinase dependent constructs described below. Moreover, "transgenic animal" also includes those recombinant animals in which gene disruption of one or more genes is caused by human intervention, including both recombination and antisense techniques.

The term "treating" as used herein is intended to encompass curing as well as ameliorating at least one symptom of the condition or disease.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

Nucleic Acids of the Present Invention

As described below, one aspect of the invention pertains to isolated nucleic acids comprising an intronic sequence of an SR-BI gene. In a preferred embodiment, the invention provides an intronic sequence of the genomic DNA sequence encoding an SR-BI protein, comprising an intronic sequence shown in FIG. 2 or set forth in any of SEQ ID NOS. 1–84 or complements thereof or homologs thereof Other preferred nucleic acids of the invention include specific SR-BI alleles, which differ from the allelic variant having the nucleotide sequence set forth in SEQ ID NO. 1 or SEQ ID NO. 3, or at least a portion thereof having a polymorphic region. Nucleic acids of the invention can function as probes or primers, e.g., in methods for determining the identity of an allelic variant of an SR-BI polymorphic region. The nucleic acids of the invention can also be used to determine whether a subject is at risk of developing a disease associated with a specific allelic variant of an SR-BI polymorphic region, e.g, a disease or disorder associated with an aberrant SR-BI activity. The nucleic acids of the invention can further be used to prepare SR-BI polypeptides encoded by specific alleles, such as mutant alleles. Such polypeptides can be used in gene therapy. Polypeptides encoded by specific SR-BI alleles, such as mutant SR-BI polypeptides, can also be used for preparing reagents, e.g., antibodies, for detecting SR-BI proteins encoded by these alleles. Accordingly, such reagents can be used to detect mutatn SR-BI proteins.

Nucleic acids of the invention comprise an intronic sequence of an SR-BI gene. The term "SR-BI intronic sequence" refers to a nucleotide sequence of an intron of an SR-BI gene. An intronic sequence can be directly adjacent to an exon or located further away from the exons. Preferred nucleic acids of the invention include an intronic sequence of an SR-BI gene which is adjacent to an exon and comprises at least about 3 consecutive nucleotides, at least about 6 consecutive nucleotides, at least about 9 consecutive nucleotides, at least about 12 consecutive nucleotides, at least about 15 consecutive nucleotides, at least about 18 consecutive nucleotides, or at least about 20 consecutive nucleotides. Isolated nucleic acids which comprise an SR-BI intronic sequence which is immediately adjacent to an exon and comprises at least about 25 consecutive nucleotides, at least about 30 consecutive nucleotides, at least about 35 consecutive nucleotides, at least about 40 consecutive nucleotides, at least about 50 consecutive nucleotides, or at least about 100 consecutive nucleotides are also within the scope of the invention. Preferred isolated nucleic acids of the invention also include those having an SR-BI intronic sequence having a nucleotide sequence of at least about 10 nucleotides, at least about 15 nucleotides, at least about 20 nucleotides, at least about 25 nucleotides, at least about 30 nucleotides, at least about 35 nucleotides, at least about 40 nucleotides, at least about 50 nucleotides or at least about 100 nucleotides. Other preferred nucleic acids of the invention can comprise an SR-BI intronic sequence having less than about 10 nucleotides, provided that the nucleotide sequence is novel. Yet other preferred isolated nucleic acids of the invention include SR-BI intronic nucleic acid sequences of an SR-BI intron, having at least about 150 consecutive nucleotides, at least about 200 consecutive nucleotides, at least about 250 consecutive nucleotides, at least about 300 consecutive nucleotides, at least about 350 consecutive nucleotides, at least about 400 consecutive nucleotides, at least about 500 consecutive nucleotides or at least about 1000 consecutive nucleotides Preferred nucleic acids of the invention comprise an SR-BI intronic sequence having a nucleotide sequence shown in FIG. 2, and/or in any of SEQ ID Nos. 1–84, complement thereof, reverse complement thereof or homolog thereof. In a preferred embodiment, the invention provides an isolated nucleic acid comprising an SR-BI intronic which is at least about 70% 75%, 80%, 85%, 90%, 95%, or preferably at least about 98%, and most preferably at least about 99% identical to an intronic nucleotide sequence shown in FIG. 2 or set forth in any of SEQ ID NOS. 1–84 or a complement thereof. In fact, as described herein, several alleles of human SR-BI genes have been identified. The invention is intended to encompass all of these alleles and SR-BI alleles not yet identified, which can be identified, e.g, according to the methods described herein.

The invention also provides isolated nucleic acids comprising at least one polymorphic region of an SR-BI gene having a nucleotide sequence which differs from the nucleotide sequence set forth in SEQ ID NO. 1 or SEQ ID NO. 3. Preferred nucleic acids have a polymorphic region located in an exon of an SR-BI gene, such as exon 8. Accordingly, preferred nucleic acids of the invention comprise a thymidine at position 41 of exon 8 (as set forth in SEQ ID NO. 65). Other preferred nucleic acids have a polymorphic region in an intron. For example, the invention provides nucleic acids having a polymorphic nucleotide at position 54 of intron 5. In a preferred embodiment, the nucleic acid has a cytidine at position 54 of intron 5 (as set forth in SEQ ID Nos. 9 and 26). In another embodiment, the nucleic acid has a thymidine at position 54 of intron 5 (as set forth in SEQ ID NO. 66). The nucleic acids can be genomic DNA, cDNA, or RNA (in which case, the nucleic acid has a uridine at position 54 of intron 5).

Preferred nucleic acids of the invention are from vertebrate genes encoding SR-BI proteins. Particularly preferred vertebrate nucleic acids are mammalian nucleic acids. A particularly preferred nucleic acid of the invention is a human nucleic acid, such as a nucleic acid comprising an SR-BI intronic sequence shown in FIG. 2 or set forth in any of SEQ ID NOS. 1–84 or complement thereof or an allele comprising a nucleotide sequence set forth in SEQ ID NO. 65.

Another aspect of the invention provides a nucleic acid which hybridizes under appropriate stringency to an SR-BI intronic sequence having a nucleotide sequence shown in introns shown in FIG. 2 or in intronic sequences set forth in any of SEQ ID Nos. 1–84 or complement thereof Appropriate stringency conditions which promote DNA hybridization, for example, 6.0× sodium chloride/sodium citrate (SSC) at about 45° C., followed by a wash of 2.0× SSC at 50° C., are known to those skilled in the art or can be found in *Current Protocols in Molecular Biology,* John Wiley & Sons, N.Y. (1989), 6.3.1–6.3.6. For example, the salt concentration in the wash step can be selected from a low stringency of about 2.0× SSC at 50° C. to a high stringency of about 0.2× SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In a preferred embodiment, a nucleic acid of the present invention will bind to at least about 20, preferably at least about 25, more preferably at least about 30 and most preferably at least about 50 consecutive nucleotides of a sequence shown in FIG. 2 or set forth in any of SEQ ID Nos. 1–84 under moderately stringent conditions, for example at about 2.0× SSC and about 400C. Even more preferred nucleic acids of the invention are capable of hybridizing under stringent conditions to an intronic sequence of at least about 20, 30, 40, or at least about 50 nucleotides as shown in FIG. 2 or as set forth in an intronic sequence of any of SEQ ID Nos. 1–84.

Hybridization, as described above, can be used to isolate nucleic acids comprising an SR-BI intron or portion thereof from various animal species. A comparison of these nucleic acids should be indicative of intronic sequences which may have a regulatory or other function, since these regions are expected to be conserved among various species. Hybridization can also be used to isolate SR-BI alleles.

The nucleic acid of the invention can be single stranded DNA (e.g., an oligonucleotide), double stranded DNA (e.g., double stranded oligonucleotide) or RNA. Preferred nucleic acids of the invention can be used as probes or primers. Primers of the invention refer to nucleic acids which hybridize to a nucleic acid sequence which is adjacent to the region of interest or which covers the region of interest and is extended. A primer can be used alone in a detection method, or a primer can be used together with at least one other primer or probe in a detection method. Primers can also be used to amplify at least a portion of a nucleic acid. Probes of the invention refer to nucleic acids which hybridize to the region of interest and which are not further extended. For example, a probe is a nucleic acid which hybridizes to a polymorphic region of an SR-BI gene, and which by hybridization or absence of hybridization to the DNA of a subject will be indicative of the identity of the allelic variant of the polymorphic region of the SR-BI gene.

Numerous procedures for determining the nucleotide sequence of a nucleic acid, or for determining the presence of mutations in nucleic acids include a nucleic acid amplification step, which can be carried out by, e.g., polymerase chain reaction (PCR). Accordingly, in one embodiment, the invention provides primers for amplifying portions of an SR-BI gene, such as portions of exons and/or portions of introns. In a preferred embodiment, the exons and/or sequences adjacent to the exons of the human SR-BI gene will be amplified to, e.g., detect which allelic variant of a polymorphic region is present in the SR-BI gene of a subject. Preferred primers comprise a nucleotide sequence complementary to an SR-BI intronic sequence or a specific allelic variant of an SR-BI polymorphic region and of sufficient length to selectively hybridize with an SR-BI gene. In a preferred embodiment, the primer, e.g., a substantially purified oligonucleotide, comprises a region having a nucleotide sequence which hybridizes under stringent conditions to about 6, 8, 10, or 12, preferably 25, 30, 40, 50, or 75 consecutive nucleotides of an SR-BI gene. In an even more preferred embodiment, the primer is capable of hybridizing to an SR-BI intron and has a nucleotide sequence of an intronic sequence shown in FIG. 2 or set forth in any of SEQ ID Nos. 1–84, complements thereof, allelic variants thereof, or complements of allelic variants thereof. For example, primers comprising a nucleotide sequence of at least about 15 consecutive nucleotides, at least about 20 nucleotides or having from about 15 to about 25 nucleotides shown in FIG. 2 or set forth in any of SEQ ID NOS. 1–84 or complement thereof are provided by the invention. Primers having a sequence of more than about 25 nucleotides are also within the scope of the invention. Preferred primers of the invention are primers that can be used in PCR for amplifying each of the exons of an SR-BI gene. Even more preferred primers of the invention have the nucleotide sequence set forth in any of SEQ ID Nos. 41–64 (see Table III).

Primers can be complementary to nucleotide sequences located close to each other or further apart, depending on the use of the amplified DNA. For example, primers can be chosen such that they amplify DNA fragments of at least about 10 nucleotides or as much as several kilobases. Preferably, the primers of the invention will hybridize selectively to nucleotide sequences located about 150 to about 350 nucleotides apart.

For amplifying at least a portion of a nucleic acid, a forward primer (i.e., 5' primer) and a reverse primer (i.e., 3' primer) will preferably be used. Forward and reverse primers hybridize to complementary stands of a double stranded nucleic acid, such that upon extension from each primer, a double stranded nucleic acid is amplified. A forward primer can be a primer having a nucleotide sequence or a portion of the nucleotide sequence shown in FIG. 2 or in SEQ ID Nos. 1–40 and 65. A reverse primer can be a primer having a nucleotide sequence or a portion of the nucleotide sequence that is complementary to a nucleotide sequence shown in FIG. 2 or in SEQ ID Nos. 1–40 and 65. Preferred forward primers comprise a nucleotide sequence set forth in SEQ ID Nos. 41, 43, 45, 47, 49, 51, 53, 55, 57, 59, 61, 63, and 85 (shown in Table III). Preferred reverse primers comprise a nucleotide sequence set forth in SEQ ID Nos. 42, 44, 46, 48, 50, 52, 54, 56, 58, 60, 62, 64, and 86. Preferred pairs of primers for amplifying each of the exons of human SR-BI are set forth in Table III.

Yet other preferred primers of the invention are nucleic acids which are capable of selectively hybridizing to an allelic variant of a polymorphic region of an SR-BI gene. Thus, such primers can be specific for an SR-BI gene sequence, so long as they have a nucleotide sequence which is capable of hybridizing to an SR-BI gene. Preferred primers are capable of specifically hybridizing to an allelic variant in which nucleotide 41 of exon 8 of human SR-BI is a thymidine, e.g., a nucleic acid having SEQ ID NO. 65. Other preferred primers are capable of specifically hybridizing to an allelic variant in which nucleotide 54 of intron 5 is a thymidine, e.g., a nucleic acid having SEQ ID NO. 66. Such primers can be used, e.g., in sequence specific oligonucleotide priming as described further herein.

The SR-BI nucleic acids of the invention can also be used as probes, e.g. in therapeutic and diagnostic assays. For instance, the present invention provides a probe comprising a substantially purified oligonucleotide, which oligonucleotide comprises a region having a nucleotide sequence that hybridizes under stringent conditions to at least approximately 6, 8, 10 or 12, preferably about 25, 30, 40, 50 or 75 consecutive nucleotides of an SR-BI gene. In one embodiment, the probes preferably hybridize to an intron of an SR-BI gene, having an intronic nucleotide sequence shown in FIG. 2 or set forth in any of SEQ ID Nos. 1–84, allelic variants thereof, complements thereof or complements of allelic variants thereof. In another embodiment, the probes are capable of hybridizing to a nucleotide sequence encompassing an intron/exon border of an SR-BI gene.

Other preferred probes of the invention are capable of hybridizing specifically to a region of an SR-BI gene which is polymorphic. In an even more preferred embodiment of the invention, the probes are capable of hybridizing specifically to one allelic variant of an SR-BI gene having a nucleotide sequence which differs from the nucleotide sequence set forth in SEQ ID NO. 1 or 3. Such probes can then be used to specifically detect which allelic variant of a polymorphic region of an SR-BI gene is present in a subject. The polymorphic region can be located in the promoter, exon, or intron sequences of an SR-BI gene. For example, preferred probes of the invention are capable of hybridizing specifically to a region overlapping nucleotide 41 of exon 8 of the human SR-BI gene. In one embodiment, the probe overlapping nucleotide 41 of exon 8 is capable of hybridizing specifically to a nucleotide sequence wherein nucleotide 41 is a thymidine (as shown in SEQ ID NO. 65). Examples of such probes include a probe having the nucleotide sequence 5' AACCGGGTCAGCGTTGAGGA 3' (SEQ ID No. 67); 5' TGCCAGAACCGGGTCAGC GTTGAGGAAGTGA 3' (SEQ ID NO. 68); and probes having the complement of these nucleotide sequences, i.e., 5' TCCTCAACGCTGACCCGGTT 3' (SEQ ID NO. 69); 5' TCACTTCCTCAACGCTGACCCGGTTCTGGCA 3' (SEQ ID NO. 70). The bold nucleotides represents the location of the nucleotide polymorphism. In another embodiment, the probe overlapping nucleotide 41 of exon 8 is capable of specifically hybridizing to a nucleotide sequence wherein nucleotide 41 is a cytidine (as shown in FIG. 2 and set forth in SEQ ID NO. 12). Examples of such probes include a probe having the nucleotide sequence 5' AACCGGGTCGGCGTTGATGA 3' (SEQ ID NO. 71); TGCCAGAACCGGGTCGGCGT TGATGAAGTGA 3' (SEQ ID NO. 72) and probes having the complement of these nucleotide sequences, i.e., 5' TCATCAACGCCGAC-CCGGTT 3' (SEQ ID NO. 73); 5' TCACTTCATCAACGC-CGACCCGGTTCTGGCA 3' (SEQ ID NO. 74).

Yet other preferred probes of the invention are capable of hybridizing specifically to a region overlapping nucleotide 54 of intron 5 of the human SR-BI gene. In one embodiment, the probe overlapping nucleotide 54 of intron 5 is capable of hybridizing specifically to a nucleotide sequence wherein nucleotide 54 is a cytidine (as shown in FIG. 2 and set forth in SEQ ID NOS. 9 and 26). Examples of such probes include a probe having the nucleotide sequence 5' AGCCATGGC-CGGGCCCACCCT 3' (SEQ ID NO. 75); 5' CGAGCAGC-CATG GCCGGGCCCACCCTCCCCT 3' (SEQ ID NO. 76); and probes having the complement of these nucleotide sequences, i.e., 5' AGGGTGGGCCCGGCCATGGCT 3' (SEQ ID NO. 77); 5' AGGGGAGGGTGGGCCCGGC-CATGGCTGCTCG 3' (SEQ ID NO. 78). In another embodiment, the probe overlapping nucleotide 54 of intron 5 is capable of specifically hybridizing to a nucleotide sequence wherein nucleotide 54 is a thymidine (as shown in SEQ ID NO. 66). Examples of such probes include a probe having the nucleotide sequence 5' AGCCATGGCCAGGC-CCACCCT 3' (SEQ ID NO. 79); 5' CGAGCAGCCATG-GCCAG GCCCACCCTCCCCT 3' (SEQ ID NO. 80); and probes having the complement of these nucleotide sequences, i.e., 5' AGGGTGGGCCTGGCCATGGCT 3' (SEQ ID NO. 81); 5' AGGGGAGGGTGGGCCTGGC-CATGGCTGCTCG 3' (SEQ ID NO. 82).

Preferred probes of the invention have a number of nucleotides sufficient to allow specific hybridization to the target nucleotide sequence. Where the target nucleotide sequence is present in a large fragment of DNA, such as a genomic DNA fragment of several tens or hundreds of kilobases, the size of the probe may have to be longer to provide sufficiently specific hybridization, as compared to a probe which is used to detect a target sequence which is present in a shorter fragment of DNA. For example, in some diagnostic methods, a portion of an SR-BI gene may first be amplified and thus isolated from the rest of the chromosomal DNA and then hybridized to a probe. In such a situation, a shorter probe will likely provide sufficient specificity of hybridization. For example, a probe having a nucleotide sequence of about 10 nucleotides may be sufficient.

In preferred embodiments, the probe or primer further comprises a label attached thereto, which, e.g., is capable of being detected, e.g. the label group is selected from amongst radioisotopes, fluorescent compounds, enzymes, and enzyme co-factors.

In a preferred embodiment of the invention, the isolated nucleic acid, which is used, e.g., as a probe or a primer, is modified, such as to become more stable. Exemplary nucleic acid molecules which are modified include phosphoramidate, phosphothioate and methylphosphonate analogs of DNA (see also U.S. Pat. Nos. 5,176,996; 5,264, 564; and 5,256,775).

The nucleic acids of the invention can also be modified at the base moiety, sugar moiety, or phosphate backbone, for example, to improve stability of the molecule. The nucleic acids, e.g., probes or primers, may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988), hybridization-triggered cleavage agents. (See, e.g., Krol et al., 1988, *BioTechniques* 6:958–976) or intercalating agents. (See, e.g., Zon, 1988, Pharm. Res. 5:539–549). To this end, the nucleic acid of the invention may be conjugated to another molecule, e.g., a peptide, hybridization triggered cross-linking agent, transport agent, hybridization-triggered cleavage agent, etc.

The isolated nucleic acid comprising an SR-BI intronic sequence may comprise at least one modified base moiety which is selected from the group including but not limited to 5-fluorouracil, 5-bromouracil, 5-chlorouracil, 5-iodouracil, hypoxanthine, xantine, 4-acetylcytidine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytidine, 5-methylcytidine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytidine, 5-methyl-2-thiouracil, 2-thiouracil, 4-thiouracil, 5-methyluracil, uracil-5- oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The isolated nucleic acid may also comprise at least one modified sugar moiety selected from the group including but not limited to arabinose, 2-fluoroarabinose, xylulose, and hexose.

In yet another embodiment, the nucleic acid comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the nucleic acid is an α-anomeric oligonucleotide. An α-anomeric oligonucleotide forms specific double-stranded hybrids with complementary RNA in which, contrary to the usual β-units, the strands run parallel to each other (Gautier et al., 1987, *Nucl. Acids Res.* 15:6625–6641). The oligonucleotide is a 2'-0-methylribonucleotide (Inoue et al., 1987, *Nucl. Acids Res.* 15:6131–6148), or a chimeric RNA-DNA analogue (Inoue et al., 1987, *FEBS Lett.* 215:327–330).

Any nucleic acid fragment of the invention can be prepared according to methods well known in the art and described, e.g., in Sambrook, J. Fritsch, E. F., and Maniatis, T. (1989) *Molecular Cloning: A Laboratory Manual,* Cold Spring Harbor Laboratory Press, Cold Spring Harbor, N.Y. For example, discrete fragments of the DNA can be prepared and cloned using restriction enzymes. Alternatively, discrete fragments can be prepared using the Polymerase Chain Reaction (PCR) using primers having an appropriate sequence.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

The invention also provides vectors and plasmids containing the nucleic acids of the invention. For example, in one embodiment, the invention provides a vector comprising at least a portion of an SR-BI gene comprising a polymorphic region and/or intronic sequence. Thus, the invention provides vectors for expressing at least a portion of the newly identified allelic variants of the human SR-BI gene, as well as other allelic variants, having a nucleotide sequence which is different from the nucleotide sequence disclosed in Calvo and Vega, supra. The allelic variants can be expressed in eukaryotic cells, e.g., cells of a subject, or in prokaryotic cells.

In one embodiment, the vector comprising at least a portion of an SR-BI allele is introduced into a host cell, such that a protein encoded by the allele is synthesized. The SR-BI protein produced can be used, e.g., for the production of antibodies, which can be used, e.g., in methods for detecting mutant forms of SR-BI. Alternatively, the vector can be used for gene therapy, and be, e.g., introduced into a subject to produce SR-BI protein. Host cells comprising a vector having at least a portion of an SR-BI gene are also within the scope of the invention.

Kits

As set forth herein, the invention provides methods, e.g., diagnostic and therapeutic methods, e.g., for determining the type of allelic variant of a polymorphic region present in an SR-BI gene, such as a human SR-BI gene. In preferred embodiments, the methods use probes or primers comprising nucleotide sequences which are complementary to an SR-BI intronic sequence or to a polymorphic region of an SR-BI gene. Accordingly, the invention provides kits for performing these methods.

In a preferred embodiment, the invention provides a kit for determining whether a subject has or is at risk of developing a disease or condition associated with a specific allelic variant of an SR-BI polymorphic region. In an even more preferred embodiment, the disease or disorder is characterized by an abnormal SR-BI activity. In an even more preferred embodiment, the invention provides a kit for determining whether a subject has or is at risk of developing a cardiovascular disease, e.g., ischemia, restenosis, congestive heart failure, atherosclerosis, aberrant lipid levels, gallstone formation, or an abnormal body mass index, e.g, obesity or cachexia.

Preferred kits comprise at least one probe or primer which is capable of specifically hybridizing to an SR-BI intronic sequence or polymorphic region and instructions for use. The kits preferably comprise at least one of the above describe nucleic acids, e.g., including nucleic acids hybridizing to an exon/intron border. Preferred kits for amplifying at least a portion of an SR-BI gene, e.g., an exon, comprise two primers, at least one of which is capable of hybridizing to an SR-BI intronic sequence. Even more preferred kits comprise a pair of primers selected from the group consisting of SEQ ID NO.41 and SEQ ID NO.42, SEQ ID NO. 43 and SEQ ID NO.44, SEQ ID NO. 45 and SEQ ID NO.46, SEQ ID NO. 47 and SEQ ID NO. 48, SEQ ID NO. 49 and SEQ ID NO. 50, SEQ ID NO. 51 and SEQ ID NO. 52, SEQ ID NO. 53 and SEQ ID NO.54, SEQ ID NO.55 and SEQ ID NO.56, SEQ ID NO. 57 and SEQ ID NO.58, SEQ ID NO. 59 and SEQ ID NO.60, SEQ ID NO. 61 and SEQ ID NO.62, SEQ ID NO.63 and SEQ ID NO.64, and SEQ ID NO. 85 and SEQ ID NO.86.

The kits of the invention can also comprise one or more control nucleic acid or reference nucleic acid, such as nucleic acids comprising an SR-BI intronic sequence. For example, a kit can comprise primers for amplifying a polymorphic region of an SR-BI gene and a control DNA corresponding to such an amplified DNA and having the nucleotide sequence of a specific allelic variant. Thus, direct comparison can be performed between the DNA amplified from a subject and the DNA having the nucleotide sequence of a specific allelic variant. In one embodiment, the control nucleic comprises at least a portion of an SR-BI gene of an individual which does not have a cardiovascular disease, aberrant lipid levels, gallstones, or a disease or disorder associated with an aberrant SR-BI activity.

Yet other kits of the invention comprise at least one reagent necessary to perform the assay. For example, the kit can comprise an enzyme. Alternatively the kit can comprise a buffer or any other necessary reagent.

Diagnostic and Prognostic Assays

The present invention provides methods for determining the molecular structure of an SR-BI gene, such as a human SR-BI gene, or a portion thereof. In one embodiment, determining the molecular structure of at least a portion of an SR-BI gene comprises determining the identity of the allelic variant of at least one polymorphic region of an SR-BI gene. A polymorphic region of an SR-BI gene can be located in an exon, an intron, at an intron/exon border, or in the promoter of the SR-BI gene.

The invention provides methods for determining whether a subject has, or is at risk of developing, a disease or condition associated with a specific allelic variant of a polymorphic region of an SR-BI gene. Such diseases can be associated with an aberrant SR-BI activity, e.g., abnormal binding to a form of a lipid, or an aberrant SR-BI protein level. An aberrant SR-BI protein level can result from an aberrant transcription or post transcriptional regulation. Thus, allelic differences in specific regions of an SR-BI gene can result in differences of SR-BI protein due to differences in regulation of expression. In particular, some of the identified polymorphisms in the human SR-BI gene may be associated with differences in the level of transcription, RNA maturation, splicing, or translation of the SR-BI gene or transcription product.

In addition, since SR-BI is a receptor that is capable of binding to various lipid related molecules, it is likely that specific alleles of the SR-BI gene are associated with other diseases or conditions involving an inappropriate lipid transfer or metabolism, e.g., atherosclerosis or a biliary disorder, such as gallstone formation. Accordingly, the invention provides diagnostic and prognostic assays for determining whether a subject is at risk of developing a disease characterized by an abnormal lipid level, e.g, atherosclerosis or gall stone formation.

In preferred embodiments, the methods of the invention can be characterized as comprising detecting, in a sample of cells from the subject, the presence or absence of a specific allelic variant of one or more polymorphic regions of an SR-BI gene. The allelic differences can be: (i) a difference in the identity of at least one nucleotide or (ii) a difference in the number of nucleotides, which difference can be a single nucleotide or several nucleotides. The invention also provides methods for detecting differences in SR-BI genes such as chromosomal rearrangements, e.g., chromosomal dislocation. The invention can also be used in prenatal diagnostics.

A preferred detection method is allele specific hybridization using probes overlapping the polymorphic site and having about 5, 10, 20, 25, or 30 nucleotides around the polymorphic region. Examples of probes for detecting specific allelic variants of the polymorphic region located in exon 8 are probes comprising a nucleotide sequence set forth in any of SEQ ID NO. 67–74. Examples of probes for detecting specific allelic variants of the polymorphic region located in intron 5 are probes comprising a nucleotide sequence set forth in any of SEQ ID NO. 75–82. In a preferred embodiment of the invention, several probes capable of hybridizing specifically to allelic variants are attached to a solid phase support, e.g., a "chip". Oligonucleotides can be bound to a solid support by a variety of processes, including lithography. For example a chip can hold up to 250,000 oligonucleotides (GeneChip, Affymetrix). Mutation detection analysis using these chips comprising oligonucleotides, also termed "DNA probe arrays" is described e.g., in Cronin et al. (1996) Human Mutation 7:244. In one embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes can be identified in a simple hybridization experiment. For example, the identity of the allelic variant of the nucleotide polymorphism of nucleotide 41 of exon 8 and of nucleotide 54 of intron 5 can be determined in a single hybridization experiment.

In other detection methods, it is necessary to first amplify at least a portion of an SR-BI gene prior to identifying the allelic variant. Amplification can be performed, e.g., by PCR and/or LCR, according to methods known in the art. In one embodiment, genomic DNA of a cell is exposed to two PCR primers and amplification for a number of cycles sufficient to produce the required amount of amplified DNA. In preferred embodiments, the primers are located between 150 and 350 base pairs apart. Preferred primers, such as primers for amplifying each of the exons of the human SR-BI gene, are listed in Table III in the Examples. Details regarding the PCR reaction are indicated in Table IV, also in the Examples.

Alternative amplification methods include: self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), Q-Beta Replicase (Lizardi, P. M. et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In one embodiment, any of a variety of sequencing reactions known in the art can be used to directly sequence at least a portion of an SR-BI gene and detect allelic variants, e.g., mutations, by comparing the sequence of the sample sequence with the corresponding wild-type (control) sequence. Exemplary sequencing reactions include those based on techniques developed by Maxam and Gilbert (*Proc. Natl Acad Sci USA* (1977) 74:560) or Sanger (Sanger et al (1977) *Proc. Nat. Acad. Sci* 74:5463). It is also contemplated that any of a variety of automated sequencing procedures may be utilized when performing the subject assays (*Biotechniques* (1995) 19:448), including sequencing by mass spectrometry (see, for example, U.S. Pat. No. 5,547,835 and international patent application Publication Number WO 94/16101, entitled *DNA Sequencing by Mass Spectrometry* by H. Köster; U.S. Pat. No. 5,547,835 and international patent application Publication Number WO 94/21822 entitled "DNA Sequencing by Mass Spectrometry Via Exonuclease Degradation" by H. Köster), and U.S. Pat. No. 5,605,798 and International Patent Application No. PCT/US96/03651 entitled *DNA Diagnostics Based on Mass Spectrometry* by H. Köster;. Cohen et al. (1996) *Adv Chromatogr* 36:127–162; and Griffin et al. (1993) *Appl Biochem Biotechnol* 38:147–159). It will be evident to one skilled in the art that, for certain embodiments, the occurrence of only one, two or three of the nucleic acid bases need be determined in the sequencing reaction. For instance, A-track or the like, e.g., where only one nucleotide is detected, can be carried out.

Yet other sequencing methods are disclosed, e.g., in U.S. Pat. No. 5,580,732 entitled "Method of DNA sequencing employing a mixed DNA-polymer chain probe" and U.S. Pat. No. 5,571,676 entitled "Method for mismatch-directed in vitro DNA sequencing".

In some cases, the presence of a specific allele of an SR-BI gene in DNA from a subject can be shown by restriction enzyme analysis. For example, a specific nucleotide polymorphism can result in a nucleotide sequence comprising a restriction site which is absent from the nucleotide sequence of another allelic variant. In particular, the presence of a cytidine at position 54 of intron 5 creates an ApaI site, whereas the presence of a thymidine, at this position destroys the ApaI site.

In a further embodiment, protection from cleavage agents (such as a nuclease, hydroxylamine or osmium tetroxide and with piperidine) can be used to detect mismatched bases in RNA/RNA DNA/DNA, or RNA/DNA heteroduplexes (Myers, et al. (1985) *Science* 230:1242). In general, the technique of "mismatch cleavage" starts by providing heteroduplexes formed by hybridizing a control nucleic acid, which is optionally labeled, e.g., RNA or DNA, comprising a nucleotide sequence of an SR-BI allelic variant with a sample nucleic acid, e.g, RNA or DNA, obtained from a tissue sample. The double-stranded duplexes are treated with an agent which cleaves single-stranded regions of the duplex such as duplexes formed based on basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine whether the control and sample nucleic acids have an identical nucleotide sequence or in which nucleotides they are different. See, for example, Cotton et al (1988) *Proc. Natl Acad Sci USA* 85:4397; Saleeba et al (1992) Methods Enzymod. 217:286–295. In a preferred embodiment, the control or sample nucleic acid is labeled for detection.

In other embodiments, alterations in electrophoretic mobility is used to identify the type of SR-BI allelic variant. For example, single strand conformation polymorphism (SSCP) may be used to detect differences in electrophoretic mobility between mutant and wild type nucleic acids (Orita et al. (1989) *Proc Natl. Acad. Sci USA* 86:2766, see also Cotton (1993) *Mutat Res* 285:125–144; and Hayashi (1992) *Genet Anal Tech Appl* 9:73–79). Single-stranded DNA fragments of sample and control nucleic acids are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In another preferred embodiment, the subject method utilizes heteroduplex analysis to separate double stranded heteroduplex molecules on the basis of changes in electrophoretic mobility (Keen et al. (1991) Trends Genet 7:5).

In yet another embodiment, the identity of an allelic variant of a polymorphic region is obtained by analyzing the movement of a nucleic acid comprising the polymorphic region in polyacrylamide gels containing a gradient of denaturant is assayed using denaturing gradient gel electrophoresis (DGGE) (Myers et al (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:1275).

Examples of techniques for detecting differences of at least one nucleotide between 2 nucleic acids include, but are not limited to, selective oligonucleotide hybridization, selective amplification, or selective primer extension. For example, oligonucleotide probes may be prepared in which the known polymorphic nucleotide is placed centrally (allele-specific probes) and then hybridized to target DNA under conditions which permit hybridization only if a perfect match is found (Saiki et al. (1986) *Nature* 324:163); Saiki et al (1989) *Proc. Natl Acad. Sci USA* 86:6230; and Wallace et al. (1979) Nucl. Acids Res. 6:3543). Such allele specific oligonucleotide hybridization techniques may be used for the simultaneous detection of several nucleotide changes in different polylmorphic regions of SR-BI. For example, oligonucleotides having nucleotide sequences of specific allelic variants are attached to a hybridizing membrane and this membrane is then hybridized with labeled sample nucleic acid. Analysis of the hybridization signal will then reveal the identity of the nucleotides of the sample nucleic acid.

Alternatively, allele specific amplification technology which depends on selective PCR amplification may be used in conjunction with the instant invention. Oligonucleotides used as primers for specific amplification may carry the allelic variant of interest in the center of the molecule (so that amplification depends on differential hybridization) (Gibbs et al (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238; Newton et al. (1989) Nucl. Acids Res. 17:2503). This technique is also termed "PROBE" for Probe Oligo Base Extension. In addition it may be desirable to introduce a novel restriction site in the region of the mutation to create cleavage-based detection (Gasparini et al (1992) *Mol. Cell Probes* 6:1).

In another embodiment, identification of the allelic variant is carried out using an oligonucleotide ligation assay (OLA), as described, e.g., in U.S. Pat. No. 4,998,617 and in Landegren, U. et al., Science 241:1077–1080 (1988). The OLA protocol uses two oligonucleotides which are designed to be capable of hybridizing to abutting sequences of a single strand of a target. One of the oligonucleotides is linked to a separation marker, e.g, biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al., Proc. Natl. Acad. Sci. (U.S.A.) 87:8923–8927 (1990). In this method, PCR is used to achieve the exponential amplification of target DNA, which is then detected using OLA.

Several techniques based on this OLA method have been developed and can be used to detect specific allelic variants of a polymorphic region of an SR-BI gene. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al. ((1996)Nucleic Acids Res 24: 3728), OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

The invention further provides methods for detecting single nucleotide polymorphisms in an SR-BI gene. Because single nucleotide polymorphisms constitute sites of variation flanked by regions of invariant sequence, their analysis requires no more than the determination of the identity of the single nucleotide present at the site of variation and it is unnecessary to determine a complete gene sequence for each patient. Several methods have been developed to facilitate the analysis of such single nucleotide polymorphisms.

In one embodiment, the single base polymorphism can be detected by using a specialized exonuclease-resistant nucleotide, as disclosed, e.g., in Mundy, C. R (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site. Cohen, D. et al. (French Patent 2,650,840; PCT Appln. No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA™ is described by Goelet, P. et al. (PCT Appln. No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. is preferably a heterogeneous phase assay, in which the primer or the target molecule is immobilized to a solid phase.

Recently, several primer-guided nucleotide incorporation procedures for assaying polymorphic sites in DNA have been described (Komher, J. S. et al., Nucl. Acids. Res. 17:7779–7784 (1989); Sokolov, B. P., Nucl. Acids Res. 18:3671 (1990); Syvanen, A. -C., et al., Genomics 8:684–692 (1990); Kuppuswamy, M. N. et al., Proc. Natl. Acad. Sci. (U.S.A.) 88:1143–1147 (1991); Prezant, T. R. et al., Hum. Mutat. 1:159–164 (1992); Ugozzoli, L. et al., GATA 9:107–112 (1992); Nyren, P. et al., Anal. Biochem. 208:171–175 (1993)). These methods differ from GBA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A. -C., et al., Amer. J. Hum. Genet. 52:46–59 (1993)).

For determining the identity of the allelic variant of a polymorphic region located in the coding region of an SR-BI gene, yet other methods than those described above can be used. For example, identification of an allelic variant which encodes a mutated SR-BI protein can be performed by using an antibody specifically recognizing the mutant protein in, e.g., immunohistochemistry or immunoprecipitation. Antibodies to wild-type SR-BI protein are described, e.g, in Acton et al. (1999) Science 271:518 (anti-mouse SR-BI antibody cross-reactive with human SR-BI). Other antibodies to wild-type SR-BI or mutated forms of SR-BI proteins can be prepared according to methods known in the art. Alternatively, one can also measure an activity of an SR-BI protein, such as binding to a lipid or lipoprotein. Binding assays are known in the art and involve, e.g., obtaining cells from a subject, and performing binding experiments with a labeled lipid, to determine whether binding to the mutated form of the receptor differs from binding to the wild-type of the receptor.

If a polymorphic region is located in an exon, either in a coding or non-coding portion of the gene, the identity of the allelic variant can be determined by determining the molecular structure of the mRNA, pre-mRNA, or cDNA. The molecular structure can be determined using any of the above described methods for determining the molecular structure of the genomic DNA, e.g., sequencing and SSCP.

The methods described herein may be performed, for example, by utilizing pre-packaged diagnostic kits, such as those described above, comprising at least one probe or primer nucleic acid described herein, which may be conveniently used, e.g., to determine whether a subject has or is at risk of developing a disease associated with a specific SR-BI allelic variant.

Sample nucleic acid for using in the above-described diagnostic and prognostic methods can be obtained from any cell type or tissue of a subject. For example, a subject's bodily fluid (e.g. blood) can be obtained by known techniques (e.g. venipuncture). Alternatively, nucleic acid tests can be performed on dry samples (e.g. hair or skin). Fetal nucleic acid samples can be obtained from maternal blood as described in International Patent Application No. WO91/07660 to Bianchi. Alternatively, amniocytes or chorionic villi may be obtained for performing prenatal testing.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, NY).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

Methods of Treatment of Diseases or Disorders

The invention further provides methods of treating subjects having a disease or disorder associated with a specific allelic variant of a polymorphic region of an SR-BI gene. In one embodiment, the method comprises (a) determining the identity of the allelic variant; and (b) administering to the subject a compound that compensates for the effect of the specific allelic variant. The polymorphic region can be localized at any location of the gene, e.g., in the promoter (e.g., in a regulatory element of the promoter), in an exon, (e.g., coding region of an exon), in an intron, or at an exon/intron border. Thus, depending on the site of the polymorphism in the SR-BI gene, a subject having a specific variant of the polymorphic region which is associated with a specific disease or condition, can be treated with compounds which specifically compensate for the allelic variant.

For example, the allelic variant can be a mutant allele, i.e., an allele which when present in one, or preferably two copies, in a subject results in a change in the phenotype of the subject. A mutation can be a substitution, deletion, and/or addition of at least one nucleotide relative to the wild-type allele. Depending on where the mutation is located in the SR-BI gene, the subject can be treated to specifically compensate for the mutation. For example, if the mutation is present in the coding region of the gene and results in an inactive or less active SR-BI protein, the subject can be treated, e.g., by administration to the subject of a nucleic acid encoding a wild-type SR-BI protein, such that the expression of the wild-type SR-BI protein compensates for the endogenous mutated form of the SR-BI protein. Nucleic acids encoding wild-type human SR-BI protein are set forth in SEQ ID Nos. 1 and 3 and are described, e.g., in Calvo and Vega (1993) J. Biol. Chem. 268:18929.

Furthermore, depending on the site of the mutation in the SR-BI protein and the specific effect on its activity, specific treatments can be designed to compensate for that effect. The SR-BI protein is a cell surface receptor which binds specific forms of lipids, e.g., modified lipid or lipoproteins, e.g., HDL. Thus, an SR-BI protein has an extracellular domain which binds specific molecules, e.g., lipids, a transmembrane domain, and an intracellular domain, which is likely to transmit an intracellular signal. The structure of SR-BI proteins is further described, e.g., in Calvo and Vega, supra; Acton et al. (1994) J. Biol. Chem. 269:21003; Acton et al. (1995) Science 271:518; Rigotti et al. (1995) J. Biol. Chem. 270:16221; Fukasawa et al. (1996) Exp. Cell. Res. 222:246; Wang et al. (1996) J. Biol. Chem. 271:21001; and published PCT Application having publication number WO 96/00288 by Acton et al. Thus, if the mutation results in an SR-BI protein which is less capable of binding certain types of modified lipids, resulting in an accumulation of such lipids in the subject, a treatment can be designed which removes such modified lipids from the subject. In one embodiment, a compound which binds this form of lipid and is capable of targeting the lipid to a site where it is eliminated, is administered to the subject. Alternatively, the expression of another cell surface receptor which binds this type of lipid can be increased. In fact, both SR-BI and the class B scavenger receptor CD36 are capable of interacting with anionic phospholipids (Rigotti et al., supra). Thus, if a subject has a mutant SR-BI protein which is defective in its binding to anionic phospholipids, the subject can be treated by administration of a compound which increases CD36 protein levels in the cells.

In situations in which the mutant SR-BI protein binds certain forms of lipids with higher affinity, and if this is causing or contributing to a disease, a subject having such a mutated SR-BI protein can be treated, e.g., by administration of compounds which inhibit or decrease the interaction between the specific form of the lipid and SR-BI. For example, soluble forms of SR-BI proteins or binding fragments thereof, can be administered to the subject. Alternatively, small molecules can be administered to the subject for interfering in the interaction between SR-BI and a lipid.

A mutant SR-BI protein can also be an SR-BI protein having a mutation in the cytoplasmic domain of the protein which results in an aberrant signal transduction from the receptor. Subjects having such a mutation can be treated, e.g., by administration of compounds which induce the same or similar signal transduction or compounds which act downstream of the receptor.

The effect of a mutation in an SR-BI protein can be determined according to methods known in the art. For example, if the mutation is located in the extracellular portion of the protein, one can perform binding assays with specific forms of lipids, e.g., HDL, and determine whether the binding affinity of such lipid with the mutated SR-BI protein is different from the binding affinity of the lipid with the wild-type protein. Such assays can be performed using a soluble form of an SR-BI protein or a membrane bound form of the protein. If the mutation in the SR-BI protein is located in the cytoplasmic domain of the protein, signal transduction experiments can be performed to determine whether the signal transduced from the mutated receptor differs from the signal transduced from the wild-type receptor. Alternatively, one can also investigate whether binding to a protein which interacts with the cytoplasmic domain of the receptor is affected by the mutation. Such determination can be made by, e.g., by immunoprecipitation.

Yet in another embodiment, the invention provides methods for treating a subject having a mutated SR-BI gene, in which the mutation is located in a regulatory region of the gene. Such a regulatory region can be localized in the promoter of the gene, in the 5' or 3' untranslated region of an exon, or in an intron. A mutation in a regulatory region can result in increased production of SR-BI protein, decreased production of SR-BI protein, or production of SR-BI having an aberrant tissue distribution. The effect of a mutation in a regulatory region upon the SR-BI protein can be determined, e.g., by measuring the SR-BI protein level or mRNA level in cells having an SR-BI gene having this mutation and which, normally (i.e., in the absence of the mutation) produce SR-BI protein. The effect of a mutation can also be determined in vitro. For example, if the mutation is in the promoter, a reporter construct can be constructed which comprises the mutated promoter linked to a reporter gene, the construct transfected into cells, and comparison of the level of expression of the reporter gene under the control of the mutated promoter and under the control of a wild-type promoter. Such experiments can also be carried out in mice transgenic for the mutated promoter. If the mutation is located in an intron, the effect of the mutation can be determined, e.g., by producing transgenic animals in which the mutated SR-BI gene has been introduced and in which the wild-type gene may have been knocked out. Comparison of the level of expression of SR-BI in the mice transgenic for the mutant human SR-BI gene with mice transgenic for a wild-type human SR-BI gene will reveal whether the mutation results in increased, decreased synthesis of the SR-BI protein and/or aberrant tissue distribution of SR-BI protein. Such analysis could also be performed in cultured cells, in which the human mutant SR-BI gene is introduced and, e.g., replaces the endogenous wild-type SR-BI gene in the cell. Thus, depending on the effect of the mutation in a regulatory region of an SR-BI gene, a specific treatment can be administered to a subject having such a mutation. Accordingly, if the mutation results in decreased production of an SR-BI protein, the subject can be treated by administration of a compound which increases synthesis, such as by increasing SR-BI gene expression, and wherein the compound acts at a regulatory element different from the one which is mutated. Alternatively, if the mutation results in increased SR-BI protein levels, the subject can be treated by administration of a compound which reduces SR-BI protein production, e.g., by reducing SR-BI gene expression or a compound which inhibits or reduces the activity of SR-BI.

Furthermore, it is likely that subjects having different allelic variants of an SR-BI polymorphic region will respond differently to therapeutic drugs to treat diseases or conditions, such as those associated with an abnormal lipid level. Cholesterol-lowering drugs include lovastatin (MEVACOR; Merck & Co.), simvastatin (ZOCOR; Merck & Co.), dextrothyroxine (CHOLOXIN; Knoll Pharmaceutical Co.), pamaqueside (Pfizer), cholestryramine (QUESTRAN; Bristol-Myers Squibb), colestipol (COLESTID; Pharmacia & Upjohn), acipomox (Pharmacia & Upjohn), fenofibrate (LIPIDIL), gemfibrozil (LOPID; Warner-Lambert), cerivastatin (LIPOBAY; Bayer), fluvastatin (LESCOL; Novartis), atorvastatin (LIPITOR, Warner-Lambert), etofylline clofibrate (DUOLIP; Merckle (Germany)), probucol (LORELCO; Hoechst Marion Roussel), omacor (Pronova (Norway), etofibrate (Merz (Germany), clofibrate (ATROMID-S; Wyeth-Ayerst (AHP)), and niacin (numerous manufacturers). Drugs for treating obesity and/or gallstones include dexfenfluramine (REDUX, Interneuron Pharmaceuticals), megestrol acetate (MEGACE, Bristol-Myers Squibb), Phenylpropanolamine (ACUTRIM; Ciba; and DEXUTRIM; Thompson), fluoxetine (PROZAC, Lilly), dextroamphetamine (DEXEDRINE, SmithKline Beecham), fenfluramine and phentermine, chenodiol (CHENIX, Solvay), orlistat (XENICAL, Roche), anandamide (Yissum (Israel)), PCM-4 (Omega Pharmaceutical), mono-octanoin (MOCTAN, Stokely-van Camp), sibutramine (MERIDIA, Knoll), testosterone (TESTODERM, Alza), oxandrolone (OXANDRIN, Bio-Technology General), ceruletide diethylamine (TYMTRAN, Pharmacia & Upjohn), testosterone and dihydrotestosterone (ANDROGEL and ANDROGEL-DHT, unimed), somatropin (SEROSTIM, Ares-Serono and BIO-TROPIN, Biotechnology General), and thalidomide (SYNOVIR, Celgene).

A correlation between drug responses and specific alleles of SR-BI can be shown, for example, by clinical studies wherein the response to specific drugs of subjects having different allelic variants of a polymorphic region of an SR-BI gene is compared. Such studies can also be performed using animal models, such as mice having various alleles of human SR-BI genes and in which, e.g., the endogenous SR-BI has been inactivated such as by a knock-out mutation. Test drugs are then administered to the mice having different human SR-BI alleles and the response of the different mice to a specific compound is compared. Accordingly, the invention provides assays for identifying the drug which will be best suited for treating a specific disease or condition in a subject. For example, it will be possible to select drugs which will be devoid of toxicity, or have the lowest level of toxicity possible for treating a subject having a disease or condition.

Other Uses for the Nucleic Acids of the Invention

The identification of different alleles of SR-BI can also be used for purposes of identifying an individual among other individuals from the same species. For example, DNA sequences can be used as a fingerprint for detection of different individuals within the same species (Thompson, J. S. and Thompson, eds., Genetics in Medicine, W B Saunders Co., Philadelphia, Pa. (1991)). This is useful, e.g., in forensic studies.

The present invention is further illustrated by the following examples which should not be construed as limiting in any way. The contents of all cited references (including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

5. EXAMPLES

The invention now being generally described, it will be more readily understood by reference to the following examples which are included merely for purposes of illustration of certain aspects and embodiments of the present invention, and are not intended to limit the invention.

Example 1

Isolation and sequence analysis of genomic DNA encoding the human SR-BI protein

A probe consisting of a 474 base pair fragment of the human SR-BI cDNA was used to isolate bacterial artificial chromosomes (BACs) containing genomic DNA encoding the human SR-BI protein from a human BAC library (Research Genetics Inc. (Huntsville, Ala.) Cat. #96041)). Two BACs were isolated by hybridizing the probe to this library. These BACs were then sized by pulse-field electrophoresis and the inserts were found to be approximately 80 and 70 kilobases long for BAC 179m10 and BAC 256i19, respectively. All further discussion will focus on BAC 179m10.

BAC 179m10 was digested with restriction enzymes and analyzed by Southern blot hybridization with portions of human SR-BI cDNA, and shown to contain a large portion of the SR-BI sequence. This BAC was then sheared by nebulizing the DNA into fragments of approximately 1–3 kb which were inserted into the pminisk vector and the resulting insert sizes ranged from 1–3 kb. Initially, clones which hybridized to the coding sequence of the full-length human SR-BI cDNA were sequenced, leading to the identification of most of the exons of the gene. Further random sequencing of the BAC sheared library led to the identification of the remaining coding exons and the adjacent intron flanking sequences.

Sequence analysis of the genomic DNA indicated that the human SR-BI gene is at least 50 kb and contains 12 coding exons and one non-coding exon (exon 13, which contains the entire 3' untranslated region). The genomic structure of human SR-BI is shown in FIG. 1. The nucleotide sequence of the exons and portions of the introns which are adjacent to the exons is shown in FIG. 2. The coding region of the human SR-BI gene consists of 12 exons (see Table I in the Detailed Description). The location of introns relative to the nucleotide sequence of a cDNA encoding human SR-BI is shown in FIG. 2 and FIG. 3 and indicated in Table II of the Detailed Description. The portions of the protein encoded by each of the exons is also shown in FIG. 3 and in Table II.

A number of the introns are extremely large (>10 kb) (see Table I in the Detailed Description). The intron/exon boundaries were remarkably similar to those found in the human CD36 gene, which is a member of the same protein family as SR-BI (Tang et al. (1994) J. Biol. Chem. 269:6011).

Example 2

Identification of primer pairs to isolate intronic, exonic, and promoter sequences for detection of polymorphisms and mutations Multiple pairs of primers were synthesized in order to amplify each of the exons or portions thereof and adjacent intronic regions. Genomic DNA from a human subject was subjected to PCR in 25 µl reactions (1× PCR Amplitaq polymerase buffer, 0.1 mM dNTPs, 0.8 µM 5' primer, 0.8 µM 3' primer, 0.75 units of Amplitaq polymerase, 50 ng genomic DNA) using each of the above described pairs of primers under the following cycle conditions: 94° C. for 2 min, 35×[94° C. for 40 sec, annealing temp for 30 sec, 72° C. for 1 min], 72° C. for 5 min, 4° C. hold. The resulting PCR products were analyzed on a 2% agarose gel. The identity of the PCR product was confirmed by digestion with a restriction enzyme and subsequent agarose electrophoresis. Twelve pairs of oligomers were chosen to serve as PCR primers to amplify regions containing each of the 12 coding exons of the human SR-BI gene and one pair of primers was chosen to serve as PCR primers to amplify a promoter region. The nucleotide sequence of these primers in indicated in Table III and nucleotide sequences to which these primers bind are shown in FIG. 2. The optimum PCR annealing temperature for each primer pair as well as the expected sizes of the PCR products and diagnostic restriction sites is set forth below in Table IV. Table IV also indicates the size of DNA fragments obtained when digesting the amplified fragment with the restriction enzyme indicated in the table. A PCR reaction using primers having SEQ ID NO. 41 and 42 for amplifying exon 1 is preferably carried out in the presence of 10% DMSO.

TABLE III

| exon | primer name | SEQ ID NO. | Nucleotide Sequence (5' -> 3') |
|---|---|---|---|
| 1 | 5e16srb1 | 41 | CCCCTGCCGCCGGAATCCTGAAG |
|   | 3e16srb1 | 42 | CGCTTTGGCGGAGCAGCCCATGTC |
| 2 | 5e22srb1 | 43 | TGGGGCCCTCATCACTCTCCTCAC |
|   | 3e22srb1 | 44 | GCAGCCTCCCCATCCCGTCCACT |
| 3 | 5e30srb1 | 45 | ATTGCAGGCGAGTAGAAG |
|   | 3e30srb1 | 46 | CAGGCGGGAGGAGAGACA |
| 4 | 5e41srb1 | 47 | TGGGCTCTTTGCTGTGAGGC |
|   | 3e41srb1 | 48 | CCAGGCTGTGTGAGGGGAAG |
| 5 | 5e50srb1 | 49 | GCCCAGAATGTTCAGACCAG |
|   | 3e50srb1 | 50 | GCACCCTCTTCACGACAAAG |
| 6 | 5e60srb1 | 51 | CACCTGAGAGGGCTTATTA |
|   | 3e60srb1 | 52 | CAAAATGCTTTCCAAGTGC |
| 7 | 5e71srb1 | 53 | GCCGCCGGGTCTGGGTGTCC |
|   | 3e71stb1 | 54 | CAGAGGCCAGAGATTAAGCAGAC |
| 8 | 5e81srb1 | 55 | TTGTATGATGTCCCCTCCCT |
|   | 3e81srb1 | 56 | TTCCCACCACCCCAGCCCAC |
| 9 | 5e91srb1 | 57 | GGTTGACTGTGTCCCTGGAG |
|   | 3e91srb1 | 58 | GGGAACACTGGAGCACTGAGC |
| 10 | 5e104srb1 | 59 | GGTGGTGAGGGTTTAGTGTG |
|   | 3e104srb1 | 60 | CTCCCCCGCCTCCTGCCTC |
| 11 | 5e112srb1 | 61 | AAGGTGTTGGGTGGCATCTG |
|   | 3e112srb1 | 62 | GGCTCCAGGCTGCGGTTGGC |
| 12 | 5e100srb1 | 63 | TTGAAGAACCGTGTAAAAC |
|   | 3e100srb1 | 64 | TTGAGGCTGAAGGAATGA |
| Prom. | 5p13srb1 | 83 | TCCTGGGTGGGCTGGCGAAGTC |
|   | 5p13srb1 | 84 | GTTTTGGGGCGGGAGCTGATGAAG |

TABLE IV

| Exon | primer pairs | Temp. | Product length | Enzyme check |
|---|---|---|---|---|
| 1 | SEQ ID NO. 41 SEQ ID NO. 42 | 65° C. | 162 bp | BamHI (144, 118) |
| 2 | SEQ ID NO. 43 SEQ ID NO. 44 | 64° C. | 294 bp | ApaI (189, 98, 7) |
| 3 | SEQ ID NO. 45 SEQ ID NO. 46 | 57° C. | 281 bp | XhoI (153, 128) |
| 4 | SEQ ID NO. 47 SEQ ID NO. 48 | 59° C. | 360 bp | SpeI (292, 68) |
| 5 | SEQ ID NO. 49 SEQ ID NO. 50 | 57° C. | 291 bp | BamHI (157, 134) |
| 6 | SEQ ID NO. 51 SEQ ID NO. 52 | 52° C. | 273 bp | DraII (179, 72, 22) |
| 7 | SEQ ID NO. 53 SEQ ID NO. 54 | 59° C. | 290 bp | EcoRI (184, 106) |
| 8 | SEQ ID NO. 55 SEQ ID NO. 56 | 58° C. | 261 bp | HaeIII (158,103) |
| 9 | SEQ ID NO. 57 SEQ ID NO. 58 | 57° C. | 206 bp | PstI (107,99) |
| 10 | SEQ ID NO. 59 SEQ ID NO. 60 | 56° C. | 253 bp | AvaII (148,105) |
| 11 | SEQ ID NO. 61 SEQ ID NO. 62 | 60° C. | 327 bp | NcoI (242, 85) |
| 12 | SEQ ID NO. 63 SEQ ID NO. 64 | 51° C. | 303 bp | PstI (184,119) |
| prom. | SEQ ID NO. 83 SEQ ID NO. 84 | 63° C. | 247 bp | BstXI (200, 47) |

Example 3

Detection of polymorphic regions in the human SR-BI gene by SSCP

Genomic DNA from a population of human subjects (142 Spanish individuals), chosen because they have a known HDL level (high, normal, or low), known body mass index, known level of triglycerides, and known age, was subjected to PCR in 25 µl reactions (1× PCR Amplitaq polymerase buffer, 0.1 mM dNTPs, 0.8 µM 5' primer, 0.8 µM 3' primer, 0.75 units of Amplitaq polymerase, 50 ng genomic DNA) using each of the above described pairs of primers under the following cycle conditions: 94° C. for 2 min, 35×[94° C. for 40 sec, annealing temp for 30 sec, 72° C. for 1 min], 72° C.

5 min, 4° C. hold. The optimum PCR annealing temperatures for each set of primers are given in Table IV. The expected sizes of the PCR products, as well as diagnostic restriction sites, are also indicated in Table IV.

The amplified genomic DNA fragments were then analyzed by SSCP (Orita et al. (1989) *PNAS USA* 86:2766, see also Cotton (1993) *Mutat Res* 285:125–144; and Hayashi (1992) *Genet Anal Tech Appl* 9:73–79). From each 25 µl PCR reaction, 3 µl was taken and added to 7 µl of loading buffer. The mixture was heated to 94° C. for 5 min and then immediately cooled in a slurry of ice-water. 3–4 µl were then loaded on a 10% polyacrylamide gel containing 10% glycerol and then subjected to electrophoresis either overnight at 4 Watts at room temperature, or 6 hours at 20 Watts at 4° C. The secondary structure of single-stranded nucleic acids varies according to sequence, thus allowing the detection of small differences in nucleic acid sequence between similar nucleic acids. At the end of the electrophoretic period, the DNA was analyzed by gently overlaying a mixture of dyes onto the gel (1× the manufacturer's recommended concentration of SYBR Green I and SYBR Green II in 0.5× TBE buffer (Molecular Probes)) for 5 min, followed by rinsing in distilled water and detection in a Fluoroimager 575 (Molecular Dynamics).

Example 4
Identification of polymorphic regions in the human SR-BI gene by direct sequencing of PCR products Upon detection of a polymorphism in an amplified SR-BI genomic region by SSCP, this region was reamplified using the aforementioned primers which were modified to contain additional sequence which could be used to directly sequence the PCR product (M13 forward sequence for 5' primer and +M13 reverse sequence for 3' primer) on the 5' end of the primers as listed in Table III. In particular, the forward primers (5' end primers) contained the nucleotide sequence "TGTAAAACGACGGCCAGT" (SEQ ID NO. 85) located 5' of the nucleotide sequences shown in Table m and the reverse primer (3' end primer) contained the nucleotide sequence "CAGGAAACAGCTATGACC" (SEQID NO. 86) located 5' of the nucleotide sequence shown in Table III. The genomic DNA from the subjects was subjected to PCR in 50 µl reactions (1× PCR Amplitaq polymerase buffer, 0.1 mM dNTPs, 0.8 µM 5' primer, 0.8 µM 3' primer, 0.75 units of Amplitaq polymerase, 50 ng genomic DNA) using each of the above described pairs of primers under the following cycle conditions: 94° C. for 2 min, 35×[94° C. for 40 sec, annealing temp for 30 sec, 72° C. for 1 min], 72° C. 5 min, 4° C. hold. The optimum PCR annealing temperatures for each of the primer pairs are given in Table IV. The newly amplified products were then purified by agarose gel electrophoresis and subjected to sequencing using M13 forward and reverse primers.

The results indicate that the polymorphism in the region of exon 8 found by SSCP, described in Example 3, was determined to constitute a change in base position 41 of exon 8. In fact, about 35% of these individuals were homozygous for an allele having a cytidine at position 41 of exon 8; about 17% of these individuals were homozygous for an allele having a thymidine at this position; and about 48% of these individuals were heterozygous, having one allele of each type.

The analysis of genomic human DNA samples from 142 Spanish individuals revealed the presence of a polymorphism in the human SR-BI gene in about 24% of individuals which is located at position 54 of intron 5. This polymorphism corresponds to a substitution of the cytidine at position 54 from the end of exon 5 (position 1 being the first nucleotide of the intron) with a thymidine.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid comprising an intronic sequence of an SR-BI gene as shown in FIG. 2 or any of SEQ ID Nos. 5–16 and 18–40.

2. An isolated nucleic acid of claim 1 comprising an intron/exon border.

3. An isolated nucleic acid, which is capable of hybridizing under a stringency of 0.2× sodium chloride sodium citrate (SSC) at 50° C., followed by a wash of 2.0× SSC at 50° C. to an intronic sequence of the nucleic acid of claim 1.

4. An isolated nucleic acid of claim 1, further comprising at least a portion of an exon.

5. An isolated nucleic acid of claim 1, comprising from about 15 to about 30 nucleotides.

6. An isolated nucleic acid of claim 1, comprising at least about 31 nucleotides.

7. An isolated nucleic acid of claim 5, comprising a nucleotide sequence selected from the group consisting of SEQ ID NO. 41 to SEQ ID NO. 64, SEQ ID NO. 83, and SEQ ID NO.84.

8. An isolated nucleic acid of claim 1, which is single stranded.

9. An isolated nucleic acid of claim 1, which further comprises a label.

10. An isolated nucleic acid, comprising an allelic variant of a polymorphic region of an SR-BI gene, which allelic variant differs from the allelic variant set forth in SEQ ID NO. 1 or 3.

11. An isolated nucleic acid of claim 10, wherein the polymorphic region is located in an exon.

12. An isolated nucleic acid of claim 11, wherein the exon is exon 8.

13. An isolated nucleic acid of claim 12, wherein the allelic variant comprises a nucleotide sequence set forth in SEQ ID NO. 65.

14. An isolated nucleic acid of claim 10, wherein the polymorphic region is located in an intron.

15. An isolated nucleic acid of claim 14, wherein the intron is intron 5.

16. An isolated nucleic acid of claim 15, wherein the allelic variant comprises a nucleotide sequence set forth in SEQ ID NO. 66.

17. An isolated intronic nucleic acid sequence of a genomic DNA sequence comprising an SR-BI gene, wherein the intronic nucleic acid sequence comprises a nucleotide sequence of any of SEQ ID NO. 18–40.

18. A kit for amplifying and/or for determining the molecular structure of, at least a portion of an SR-BI gene, comprising a probe or primer which is capable of hybridizing to an SR-BI intronic sequence as shown in FIG. 2 or any of SEQ ID Nos. 5–16 and 18–40 and instructions for use.

19. A kit of claim 18, wherein the probe or primer is capable of hybridizing to a nucleic acid comprising an intron/exon border of an SR-BI gene as shown in FIG. 2 or any of SEQ ID Nos. 5–16 and 18–40.

20. A kit of claim 18, wherein the probe or primer is capable of hybridizing to an allelic variant of a polymorphic region of an SR-BI gene, and wherein the allelic variant differs from the allelic variant set forth in SEQ ID NO. 1 or 3.

21. A kit of claim 20, wherein the polymorphic region is located in an exon.

22. A kit of claim 21, wherein the exon is exon 8.

23. A kit of claim 22, wherein the allelic variant of a polymorphic region has a nucleotide sequence set forth in SEQ ID NO. 65.

24. A kit of claim 20, wherein the polymorphic region is located in an intron.

25. A kit of claim 24, wherein the intron is intron 5.

26. A kit of claim 25, wherein the allelic variant of a polymorphic region has a nucleotide sequence set forth in SEQ ID NO. 66.

27. A kit of claim 18, further comprising a second probe or primer.

28. A kit of claim 18, wherein the probe or primer has a nucleotide sequence from about 15 to about 30 nucleotides.

29. A kit of claim 28, wherein the probe or primer comprises a nucleotide sequence selected from the group consisting of nucleic acids having a nucleotide sequence set forth in SEQ ID Nos. 41–64, SEQ ID Nos. 67–82, and SEQ ID Nos 83–84.

30. A kit of claim 29, wherein the kit has two primers selected from the group consisting of nucleic acids having a nucleotide sequence set forth in SEQ ID Nos. 41–64 and SEQ ID Nos. 83–84.

31. A kit of claim 18, wherein the probe or primer is a single stranded nucleic acid.

32. A kit of claim 18, wherein the probe or primer is labeled.

33. A method for determining the identity of an allele of a human SR-BI gene in a nucleic acid obtained from a subject, comprising contacting a sample nucleic acid comprising the allele with a probe or primer having a sequence which is complementary to a human SR-BI gene sequence, to thereby determine the identity of the allele, wherein the probe or primer is capable of hybridizing to an SR-BI intron as shown in FIG. 2 or any of SEQ ID Nos. 5–16 and 18–40.

34. A method of claim 33, wherein the probe or primer is capable of hybridizing to an allelic variant of a polymorphic region, and wherein the allelic variant differs from the allelic variant set forth in SEQ ID NO. 1 or 3.

35. A method of claim 33, wherein determining the the identity of the allele comprises determining the identity of at least one nucleotide of a polymorphic region.

36. A method of claim 33, wherein determining the identity of the allele consists of determining the nucleotide content of a polymorphic region.

37. A method of claim 36, wherein determining the nucleotide content comprises sequencing the nucleotide sequence.

38. A method of claim 33, wherein determining the identity of the allele comprises performing a restriction enzyme site analysis.

39. A method of claim 33, wherein determining the identity of the allele is carried out by single-stranded conformation polymorphism.

40. A method of claim 33, wherein determining the identity of the allele is carried out by allele specific hybridization.

41. A method of claim 33, wherein determining the identity of the allele is carried out by primer specific extension.

42. A method of claim 33, wherein determining the identity of the allele is carried out by an oligonucleotide ligation assay.

43. A method of claim 33, wherein the probe or primer has a nucleotide sequence from about 15 to about 30 nucleotides.

44. A method of claim 43, wherein the probe or primer is selected from the group consisting of nucleic acids having a nucleotide sequence set forth in SEQ ID Nos. 41–65.

45. A method of claim 44, wherein the method comprises hybridizing the sample nucleic acid with two primers selected from the group consisting of nucleic acids having a nucleotide sequence set forth in SEQ ID Nos. 41–64 and SEQ ID Nos. 83–84.

46. A method of claim 33, wherein the probe or primer is a single stranded nucleic acid.

47. A method of claim 33, wherein the probe or primer is labeled.

48. A method of claim 33, wherein the probe or primer is capable of hybridizing to an intron/exon border of an SR-BI gene.

49. A method for selecting the appropriate drug to administer to an individual having a disease or condition which is associated with a specific allele of an SR-=BI gene, comprising determining whether the specific allele is present in a nucleic acid sample of the individual and selecting the appropriate drug if the specific allele is present.

50. A method of claim 49, wherein the disease or condition is abnormal lipid metabolism, inappropriate lipid levels, a cardiovascular disease, atherosclerosis) gallstone formation, or an abnormal body mass index.

51. A method of claim 49, wherein the allele contains a thymidine at position 41 of exon 8 as shown in SEQ ID No. 65.

52. A method of claim 49, wherein the allele contains a thymidine at position 54 of intron 5 as shown in SEQ ID No. 66.

* * * * *

UNITED STATES PATENT AND TRADEMARK OFFICE
CERTIFICATE OF CORRECTION

PATENT NO. : 5,998,141
DATED : Dec. 7, 1999
INVENTOR(S) : Susan Laurene Acton

It is certified that error appears in the above-identified patent and that said Letters Patent is hereby corrected as shown below:

delete "3%" at column 7, line 57, and insert --35%--;

delete "(m²)" at column 10, line 13, and insert --(m)²--;

delete "400C" at column 17, line 33, and insert --40°C--;

delete "SR-=BI" in claim 49, and insert --SR-BI--; and delete the parenthesis after "atherosclerosis" in claim 50, and insert a comma.

Signed and Sealed this

Twenty-seventh Day of February, 2001

Attest:

NICHOLAS P. GODICI

*Attesting Officer*   *Acting Director of the United States Patent and Trademark Office*